(12) United States Patent
Look et al.

(10) Patent No.: US 11,744,600 B2
(45) Date of Patent: *Sep. 5, 2023

(54) ASPIRATION MONITORING SYSTEM AND METHOD

(71) Applicant: INCUVATE, LLC, Irvine, CA (US)

(72) Inventors: David M. Look, Newport Beach, CA (US); Bradley S. Culbert, Mission Viejo, CA (US)

(73) Assignee: Incuvate, LLC, Irvine, CA (US)

( * ) Notice: Subject to any disclaimer, the term of this patent is extended or adjusted under 35 U.S.C. 154(b) by 614 days.

This patent is subject to a terminal disclaimer.

(21) Appl. No.: 16/883,094

(22) Filed: May 26, 2020

(65) Prior Publication Data

US 2020/0281610 A1     Sep. 10, 2020

Related U.S. Application Data

(63) Continuation of application No. 15/245,124, filed on Aug. 23, 2016, now Pat. No. 10,702,292.
(Continued)

(51) Int. Cl.
*A61M 31/00*     (2006.01)
*A61M 1/00*      (2006.01)
(Continued)

(52) U.S. Cl.
CPC ............. *A61B 17/22* (2013.01); *A61M 1/732* (2021.05); *A61M 1/74* (2021.05);
(Continued)

(58) Field of Classification Search
CPC ........ A61M 31/00; A61M 25/00; A61M 1/00; A61M 27/00; A61M 1/772;
(Continued)

(56) References Cited

U.S. PATENT DOCUMENTS 1,114,268 A   10/1914  Kells
1,148,093 A    7/1915  Kells
(Continued)

FOREIGN PATENT DOCUMENTS

DE      3715418 A1    11/1987
EP       806213 A1    11/1997
(Continued)

OTHER PUBLICATIONS

English translation of JPH04-20349 (5 pages).
(Continued)

*Primary Examiner* — Sarah Al Hashimi
*Assistant Examiner* — Ilya Y Treyger
(74) *Attorney, Agent, or Firm* — BLAIR WALKER IP SERVICES, LLC

(57) ABSTRACT

A system for real time monitoring of catheter aspiration includes a pressure sensor configured for placement in fluid communication with a lumen which at least partially includes an aspiration lumen of a catheter, the aspiration lumen configured to couple to a vacuum source, a measurement device coupled to the pressure sensor and configured for measuring deviations in fluid pressure, and a communication device coupled to the measurement device and configured to generate a continuous signal which is proportional to measured fluid pressure.

20 Claims, 28 Drawing Sheets

Related U.S. Application Data

(60) Provisional application No. 62/318,388, filed on Apr. 5, 2016, provisional application No. 62/239,953, filed on Oct. 11, 2015, provisional application No. 62/239,795, filed on Oct. 9, 2015, provisional application No. 62/213,385, filed on Sep. 2, 2015, provisional application No. 62/211,637, filed on Aug. 28, 2015.

(51) Int. Cl.
*A61B 17/22* (2006.01)
*A61M 25/00* (2006.01)
*A61M 27/00* (2006.01)
*A61B 17/00* (2006.01)
*A61B 90/00* (2016.01)

(52) U.S. Cl.
CPC .............. *A61B 2017/00119* (2013.01); *A61B 2017/22079* (2013.01); *A61B 2090/064* (2016.02); *A61B 2217/005* (2013.01); *A61M 1/772* (2021.05); *A61M 2205/3303* (2013.01); *A61M 2205/3331* (2013.01); *A61M 2205/3334* (2013.01); *A61M 2205/581* (2013.01); *A61M 2205/582* (2013.01); *A61M 2205/583* (2013.01)

(58) Field of Classification Search
CPC .. A61M 2205/3303; A61M 2205/3331; A61M 2205/3334; A61M 2205/581; A61B 2090/064; A61B 2017/00119; A61B 2017/22079; A61B 2217/005
See application file for complete search history.

(56) References Cited

U.S. PATENT DOCUMENTS

| | | |
|---|---|---|
| 2,804,075 A | 8/1957 | Borden |
| 3,429,313 A | 2/1969 | Romanelli |
| 3,631,847 A | 1/1972 | Hobbs, II |
| 3,693,613 A | 9/1972 | Kelman |
| 3,707,967 A | 1/1973 | Kitrilakis et al. |
| 3,744,555 A | 7/1973 | Fletcher et al. |
| 3,916,892 A | 11/1975 | Latham, Jr. |
| 3,930,505 A | 1/1976 | Wallach |
| 3,955,573 A | 5/1976 | Hansen et al. |
| 4,299,221 A | 11/1981 | Phillips et al. |
| 4,465,470 A | 8/1984 | Keiman |
| 4,574,812 A | 3/1986 | Arkans |
| 4,606,347 A | 8/1986 | Fogarty et al. |
| 4,638,539 A | 1/1987 | Palmer |
| 4,651,738 A | 3/1987 | Demer et al. |
| 4,690,672 A | 9/1987 | Veltrup |
| 4,832,685 A | 5/1989 | Haines |
| 4,898,574 A | 2/1990 | Uchiyama et al. |
| 4,998,919 A | 3/1991 | Schnepp-Pesch |
| 5,057,098 A | 10/1991 | Zelman |
| 5,064,428 A | 11/1991 | Cope et al. |
| 5,073,164 A | 12/1991 | Hollister et al. |
| 5,125,893 A | 6/1992 | Dryden |
| 5,135,482 A | 8/1992 | Neracher |
| 5,197,795 A | 3/1993 | Mahurkar et al. |
| 5,234,407 A | 8/1993 | Teirstein et al. |
| 5,248,297 A | 9/1993 | Takase |
| 5,273,047 A | 12/1993 | Tripp et al. |
| 5,318,518 A | 6/1994 | Plechinger et al. |
| 5,322,504 A | 6/1994 | Doherty et al. |
| 5,324,263 A | 6/1994 | Kraus et al. |
| 5,342,293 A | 8/1994 | Zanger |
| 5,368,555 A | 11/1994 | Sussman et al. |
| 5,385,562 A | 1/1995 | Adams et al. |
| 5,395,315 A | 3/1995 | Griep |
| 5,403,276 A | 4/1995 | Schechter et al. |
| 5,419,772 A | 5/1995 | Teitz et al. |
| 5,486,183 A | 1/1996 | Middleman et al. |
| 5,490,837 A | 2/1996 | Blaeser et al. |
| 5,496,267 A | 3/1996 | Drasler et al. |
| 5,527,274 A | 6/1996 | Zakko |
| 5,536,242 A | 7/1996 | Willard et al. |
| 5,577,674 A | 11/1996 | Altonji et al. |
| 5,581,038 A | 12/1996 | Lampropoulos et al. |
| 5,606,968 A | 3/1997 | Mang |
| 5,624,394 A | 4/1997 | Barnitz et al. |
| 5,647,847 A | 7/1997 | Lafontaine et al. |
| 5,713,849 A | 2/1998 | Bosma et al. |
| 5,713,851 A | 2/1998 | Boudewijn et al. |
| 5,730,717 A | 3/1998 | Gelbfish |
| 5,785,685 A | 7/1998 | Kugler et al. |
| 5,795,322 A | 8/1998 | Boudewijn |
| 5,827,229 A | 10/1998 | Auth et al. |
| 5,843,022 A | 12/1998 | Willard et al. |
| 5,885,244 A | 3/1999 | Leone et al. |
| 5,910,252 A | 6/1999 | Truitt et al. |
| 5,916,192 A | 6/1999 | Nita et al. |
| 5,989,210 A | 11/1999 | Morris et al. |
| 6,019,728 A | 2/2000 | Iwata et al. |
| 6,022,336 A | 2/2000 | Zadno-Azizi et al. |
| 6,096,001 A | 8/2000 | Drasler et al. |
| 6,129,697 A | 10/2000 | Drasler et al. |
| 6,129,698 A | 10/2000 | Beck |
| 6,146,396 A | 11/2000 | Kónya et al. |
| 6,190,357 B1 | 2/2001 | Ferrari et al. |
| 6,196,989 B1 | 3/2001 | Padget et al. |
| 6,206,898 B1 | 3/2001 | Honeycutt et al. |
| 6,224,570 B1 | 5/2001 | Le et al. |
| 6,258,061 B1 | 7/2001 | Drasler et al. |
| 6,283,719 B1 | 9/2001 | Frantz et al. |
| 6,293,960 B1 | 9/2001 | Ken |
| 6,375,635 B1 | 4/2002 | Moutafis et al. |
| 6,471,683 B2 | 10/2002 | Drasler et al. |
| 6,481,439 B1 | 11/2002 | Lewis et al. |
| 6,544,209 B1 | 4/2003 | Drasler et al. |
| 6,572,578 B1 | 6/2003 | Blanchard |
| 6,579,270 B2 | 6/2003 | Sussman et al. |
| 6,599,271 B1 | 7/2003 | Easley |
| 6,616,679 B1 | 9/2003 | Khosravi et al. |
| 6,622,367 B1 | 9/2003 | Bolduc et al. |
| 6,635,070 B2 | 10/2003 | Leeflang et al. |
| 6,719,717 B1 | 4/2004 | Johnson et al. |
| 6,755,803 B1 | 6/2004 | Le et al. |
| 6,755,812 B2 | 6/2004 | Peterson et al. |
| 6,926,726 B2 | 8/2005 | Drasler et al. |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,232,452 B2 | 6/2007 | Adams et al. |
| 7,374,560 B2 | 5/2008 | Ressemann et al. |
| 7,481,222 B2 | 1/2009 | Reissmann |
| 7,503,904 B2 | 3/2009 | Choi |
| 7,580,743 B2 | 8/2009 | Bourlion et al. |
| 7,591,816 B2 | 9/2009 | Wang et al. |
| 7,621,886 B2 | 11/2009 | Burnett |
| 7,666,161 B2 | 2/2010 | Nash et al. |
| 7,699,804 B2 | 4/2010 | Barry et al. |
| 7,717,898 B2 | 5/2010 | Gately et al. |
| 7,736,355 B2 | 6/2010 | Itou et al. |
| 7,753,868 B2 | 7/2010 | Hoffa |
| 7,753,880 B2 | 7/2010 | Malackowski |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,846,175 B2 | 12/2010 | Bonnette et al. |
| 7,867,192 B2 | 1/2011 | Bowman et al. |
| 7,875,004 B2 | 1/2011 | Yodfat et al. |
| 7,879,022 B2 | 2/2011 | Bonnette et al. |
| 7,887,510 B2 | 2/2011 | Karpowicz et al. |
| 7,905,710 B2 | 3/2011 | Wang et al. |
| 7,914,482 B2 | 3/2011 | Urich et al. |
| 7,918,654 B2 | 4/2011 | Adahan |
| 7,918,822 B2 | 4/2011 | Kumar et al. |

(56) References Cited

U.S. PATENT DOCUMENTS

| | | |
|---|---|---|
| 7,918,835 B2 | 4/2011 | Callahan et al. |
| 7,935,077 B2 | 5/2011 | Thor et al. |
| 7,951,073 B2 | 5/2011 | Freed |
| 7,951,112 B2 | 5/2011 | Patzer |
| 7,959,603 B2 | 6/2011 | Wahr et al. |
| 7,981,129 B2 | 7/2011 | Nash et al. |
| 3,007,490 A1 | 8/2011 | Schaeffer et al. |
| 7,998,114 B2 | 8/2011 | Lombardi |
| 3,012,766 A1 | 9/2011 | Graham |
| 3,034,018 A1 | 10/2011 | Lutwyche |
| 8,043,313 B2 | 10/2011 | Krolik et al. |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 8,075,546 B2 | 12/2011 | Carlisle et al. |
| 8,123,778 B2 | 2/2012 | Brady et al. |
| 8,140,146 B2 | 3/2012 | Kim et al. |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,202,243 B2 | 6/2012 | Morgan |
| 8,209,060 B2 | 6/2012 | Ledford |
| 8,246,573 B2 | 8/2012 | Ali et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,317,739 B2 | 11/2012 | Kuebler |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,268 B2 | 12/2012 | Ring et al. |
| 8,337,175 B2 | 12/2012 | Dion et al. |
| 8,343,131 B2 | 1/2013 | Vinten-Johansen |
| 8,348,896 B2 | 1/2013 | Wagner |
| 8,353,858 B2 | 1/2013 | Kozak et al. |
| 8,353,860 B2 | 1/2013 | Boulais et al. |
| 8,372,038 B2 | 2/2013 | Urich et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,454,557 B1 | 6/2013 | Qi et al. |
| 8,465,456 B2 | 6/2013 | Stivland |
| 8,465,867 B2 | 6/2013 | Kim |
| 8,483,980 B2 | 7/2013 | Moberg et al. |
| 8,491,523 B2 | 7/2013 | Thor et al. |
| 8,506,537 B2 | 8/2013 | Torstensen et al. |
| 8,523,801 B2 | 9/2013 | Nash et al. |
| 8,545,514 B2 | 10/2013 | Ferrera |
| 8,562,555 B2 | 10/2013 | MacMahon et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier, Jr. et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,783,151 B1 | 7/2014 | Janardhan et al. |
| 8,803,030 B1 | 8/2014 | Janardhan et al. |
| 8,808,270 B2 | 8/2014 | Dann et al. |
| 8,852,219 B2 | 10/2014 | Wulfman et al. |
| 8,926,525 B2 | 1/2015 | Hulvershorn et al. |
| 8,970,384 B2 | 3/2015 | Yodfat et al. |
| 9,248,221 B2 | 2/2016 | Look et al. |
| 9,352,076 B2 | 5/2016 | Boynton et al. |
| 9,433,427 B2 | 9/2016 | Look et al. |
| 2001/0051811 A1 | 12/2001 | Bonnette et al. |
| 2002/0068895 A1 | 6/2002 | Beck |
| 2002/0088752 A1 | 7/2002 | Balschat et al. |
| 2002/0133114 A1 | 9/2002 | Itoh et al. |
| 2002/0138095 A1 | 9/2002 | Mazzocchi et al. |
| 2002/0165575 A1 | 11/2002 | Saleh |
| 2002/0173819 A1 | 11/2002 | Leeflang et al. |
| 2003/0032918 A1 | 2/2003 | Quinn |
| 2003/0069549 A1 | 4/2003 | MacMahon et al. |
| 2003/0088209 A1 | 5/2003 | Chiu et al. |
| 2003/0136181 A1 | 7/2003 | Balschat et al. |
| 2003/0139751 A1 | 7/2003 | Evans et al. |
| 2003/0144688 A1 | 7/2003 | Brady et al. |
| 2003/0216760 A1 | 11/2003 | Welch et al. |
| 2003/0220556 A1 | 11/2003 | Porat et al. |
| 2003/0236533 A1 | 12/2003 | Wilson et al. |
| 2004/0049225 A1 | 3/2004 | Denison |
| 2004/0087988 A1 | 5/2004 | Heitzmann et al. |
| 2004/0116873 A1 | 6/2004 | Fojtik |
| 2004/0147871 A1 | 7/2004 | Burnett |
| 2004/0153109 A1 | 8/2004 | Tiedtke et al. |
| 2004/0158136 A1 | 8/2004 | Gough et al. |
| 2004/0167463 A1 | 8/2004 | Zawacki |
| 2004/0193046 A1 | 9/2004 | Nash et al. |
| 2004/0199201 A1 | 10/2004 | Kellet et al. |
| 2004/0243157 A1 | 12/2004 | Connor et al. |
| 2005/0065426 A1 | 3/2005 | Porat et al. |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0238503 A1 | 10/2005 | Rush et al. |
| 2005/0240146 A1 | 10/2005 | Nash et al. |
| 2006/0009785 A1 | 1/2006 | Maitland et al. |
| 2006/0058836 A1 | 3/2006 | Bose et al. |
| 2006/0063973 A1 | 3/2006 | Makower et al. |
| 2006/0064123 A1 | 3/2006 | Bonnette et al. |
| 2006/0142630 A1 | 6/2006 | Meretei |
| 2007/0073233 A1 | 3/2007 | Thor et al. |
| 2007/0078438 A1 | 4/2007 | Okada |
| 2007/0197956 A1 | 8/2007 | Le et al. |
| 2007/0197963 A1 | 8/2007 | Griffiths et al. |
| 2007/0225739 A1 | 9/2007 | Pintor et al. |
| 2007/0249990 A1 | 10/2007 | Cosmescu |
| 2008/0009784 A1 | 1/2008 | Leedle et al. |
| 2008/0023005 A1 | 1/2008 | Tokunaga |
| 2008/0097339 A1 | 4/2008 | Ranchod et al. |
| 2008/0097563 A1 | 4/2008 | Petrie et al. |
| 2008/0195139 A1 | 8/2008 | Donald et al. |
| 2008/0249501 A1 | 10/2008 | Yamasaki |
| 2008/0255596 A1 | 10/2008 | Jenson et al. |
| 2008/0294181 A1 | 11/2008 | Wensel et al. |
| 2008/0306465 A1 | 12/2008 | Bailey et al. |
| 2008/0319376 A1 | 12/2008 | Wilcox et al. |
| 2009/0054825 A1 | 2/2009 | Melsheimer et al. |
| 2009/0105690 A1 | 4/2009 | Schaeffer et al. |
| 2009/0157057 A1 | 6/2009 | Ferren et al. |
| 2009/0205426 A1 | 8/2009 | Balschat et al. |
| 2009/0292212 A1 | 11/2009 | Ferren et al. |
| 2010/0030186 A1 | 2/2010 | Stivland |
| 2010/0094201 A1 | 4/2010 | Mallaby |
| 2010/0130906 A1 | 5/2010 | Balschat et al. |
| 2010/0204672 A1 | 8/2010 | Lockhart et al. |

(56) References Cited

U.S. PATENT DOCUMENTS

| | | |
|---|---|---|
| 2010/0217276 A1 | 8/2010 | Garrison et al. |
| 2010/0274191 A1 | 10/2010 | Ting |
| 2010/0280761 A1 | 11/2010 | Balschat et al. |
| 2010/0324576 A1 | 12/2010 | Pintor et al. |
| 2011/0106019 A1 | 5/2011 | Bagwell et al. |
| 2011/0160683 A1 | 6/2011 | Pinotti Barbosa et al. |
| 2011/0263976 A1 | 10/2011 | Hassan et al. |
| 2012/0022404 A1 | 1/2012 | Fojtik |
| 2012/0059340 A1 | 3/2012 | Larsson |
| 2012/0071907 A1 | 3/2012 | Pintor et al. |
| 2012/0123509 A1 | 5/2012 | Merrill et al. |
| 2012/0130415 A1 | 5/2012 | Tai et al. |
| 2012/0203168 A1 | 8/2012 | Fujimoto et al. |
| 2012/0259265 A1 | 10/2012 | Salehi et al. |
| 2012/0289910 A1 | 11/2012 | Shtul et al. |
| 2012/0291811 A1 | 11/2012 | Dabney et al. |
| 2013/0062265 A1 | 3/2013 | Balschat et al. |
| 2013/0069783 A1 | 3/2013 | Caso et al. |
| 2013/0150813 A1 | 6/2013 | Gordon et al. |
| 2013/0190701 A1 | 7/2013 | Kim |
| 2013/0267891 A1 | 10/2013 | Malhi et al. |
| 2013/0305839 A1 | 11/2013 | Muench et al. |
| 2013/0310845 A1 | 11/2013 | Thor et al. |
| 2014/0005699 A1 | 1/2014 | Bonnette et al. |
| 2014/0012226 A1 | 1/2014 | Hochman |
| 2014/0096599 A1 | 4/2014 | Münch et al. |
| 2014/0142594 A1 | 5/2014 | Fojtik |
| 2014/0147246 A1 | 5/2014 | Chappel et al. |
| 2014/0155931 A1 | 6/2014 | Bose et al. |
| 2014/0200483 A1 | 7/2014 | Fojtik |
| 2014/0276920 A1 | 9/2014 | Hendrick et al. |
| 2014/0298888 A1 | 10/2014 | Fritsche et al. |
| 2014/0309589 A1 | 10/2014 | Momose et al. |
| 2014/0323906 A1 | 10/2014 | Peallield et al. |
| 2014/0360248 A1 | 12/2014 | Fritsche et al. |
| 2015/0094673 A1 | 4/2015 | Pratt et al. |
| 2015/0094748 A1 | 4/2015 | Nash et al. |
| 2016/0113576 A1 | 4/2016 | Hulvershorn et al. |

FOREIGN PATENT DOCUMENTS

| | | |
|---|---|---|
| EP | 726466 B1 | 4/2002 |
| EP | 1488748 A1 | 12/2004 |
| JP | H026005 U | 1/1990 |
| JP | 03-297470 A | 4/1990 |
| JP | H0420349 | 1/1992 |
| JP | 06-142114 A | 5/1994 |
| JP | 2004049706 A | 2/2004 |
| JP | 2007-117273 A | 5/2007 |
| JP | 2012-115689 A | 6/2012 |
| JP | 2013-009919 A | 1/2013 |
| JP | 2015142849 A | 8/2015 |
| WO | WO199005493 A1 | 5/1990 |
| WO | WO1996001079 A1 | 1/1996 |
| WO | WO1996035469 A1 | 11/1996 |
| WO | WO199918850 A1 | 4/1999 |
| WO | WO2001037916 A1 | 5/2001 |
| WO | 02/19928 A2 | 3/2002 |
| WO | WO03/101309 | 12/2003 |
| WO | WO2004/037178 A2 | 5/2004 |
| WO | WO2004100772 A2 | 11/2004 |
| WO | WO2005/065750 | 7/2005 |
| WO | WO2007/002154 A2 | 1/2007 |
| WO | WO2007143633 A2 | 12/2007 |
| WO | WO2008097993 A2 | 8/2008 |
| WO | WO2011/022073 A1 | 2/2011 |
| WO | WO2011/046028 A1 | 4/2011 |
| WO | WO2014/007949 A1 | 1/2014 |

OTHER PUBLICATIONS

"Comparison of Dimensions and Aspiration Rate of the Pronto V3, Pronto LP, Export XT, Export AP, Fetch, Xtract, Diver C.E. and QuickCat Catheter", Vascular Solutions, Inc., downloaded from internet Oct. 22, 2014.

Frölich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.

Gousios, A., Sheam, M, "Effect of Intravenous Heparin on Human Blood Viscosity", Circulation, Dec. 1959, pp. 1063-1066, vol. 20, American Heart Association, Dallas, USA.

"Infusion Liquid Flow Sensors—Safe, Precise and Reliable", Sensirion, downloaded from internet Apr. 3, 2015.

Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.

Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.

Rodriquez, R., Condé-Green, A., "Quantification of Negative Pressures Generated by Syringes of Different Calibers Used for Liposuction", Plastic & Reconstructive Surgery, Aug. 2012, pp. 383e-384e, vol. 130, No. 2, Lippicott Williams & Wilkins, Philadelphia, USA.

Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

"Guidon", IMDS, downloaded from Internet Jun. 29, 2015, http://www.imds.nl/our_product/guidon/.

Meritrans, Merit Medical Systems, Inc., 400545002/B IS 120606, Date unknown (2 pages).

Merit Mentor Simulator/Tester Instructions for use, Merit Medical Systems, Inc. 460101002 ID 062696, Date Unknown (12 pages).

PCT International Search Report and Written Opinion for PCT/US2016/048786, Applicant: Incuvate, LLC, Forms PCT/ISA/220,210, and 237 dated Feb. 1, 2017 (10 pages).

Extended European Search Report dated Jul. 9, 2018, in EP App. No. 16842657.5 filed Aug. 25, 2016 (9 pages).

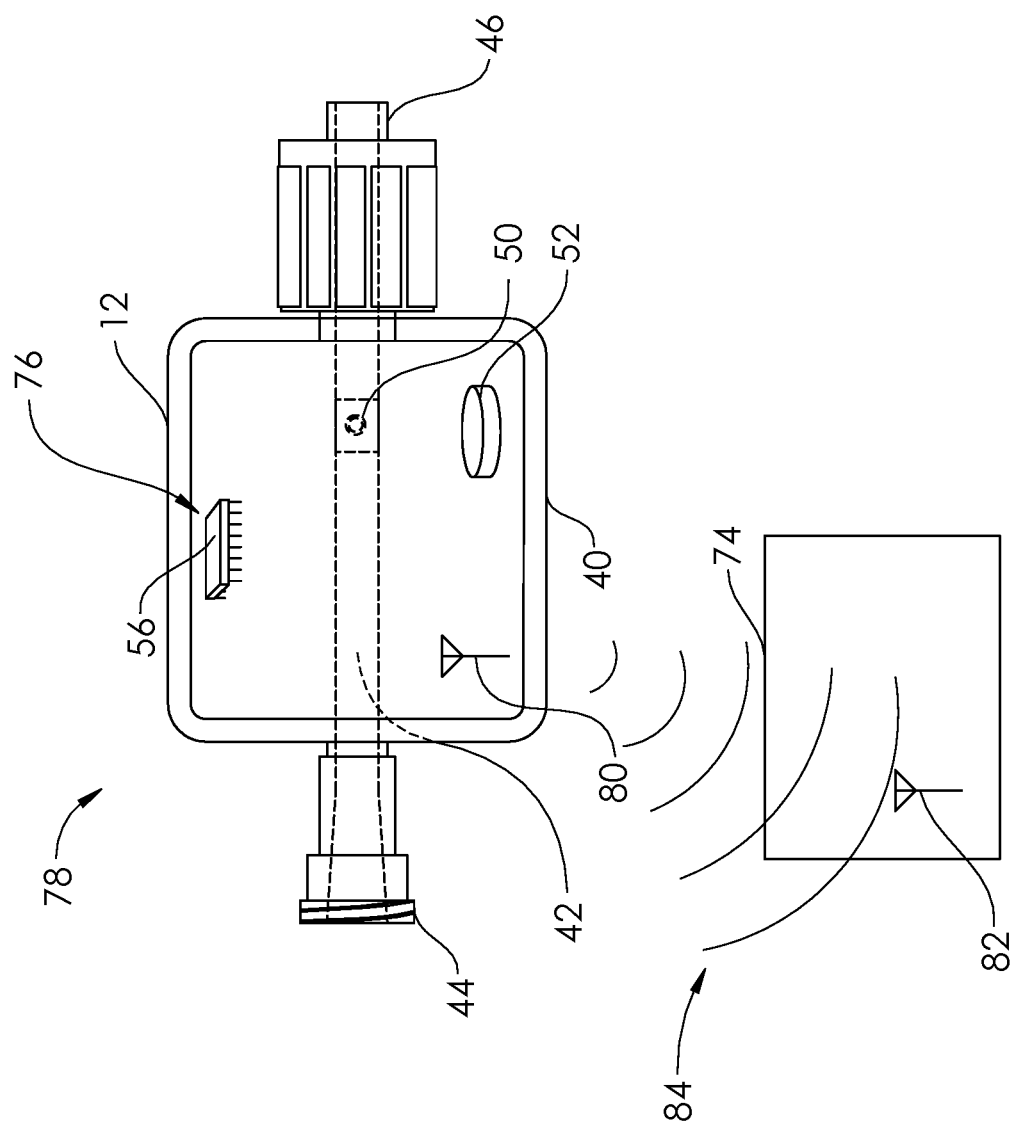

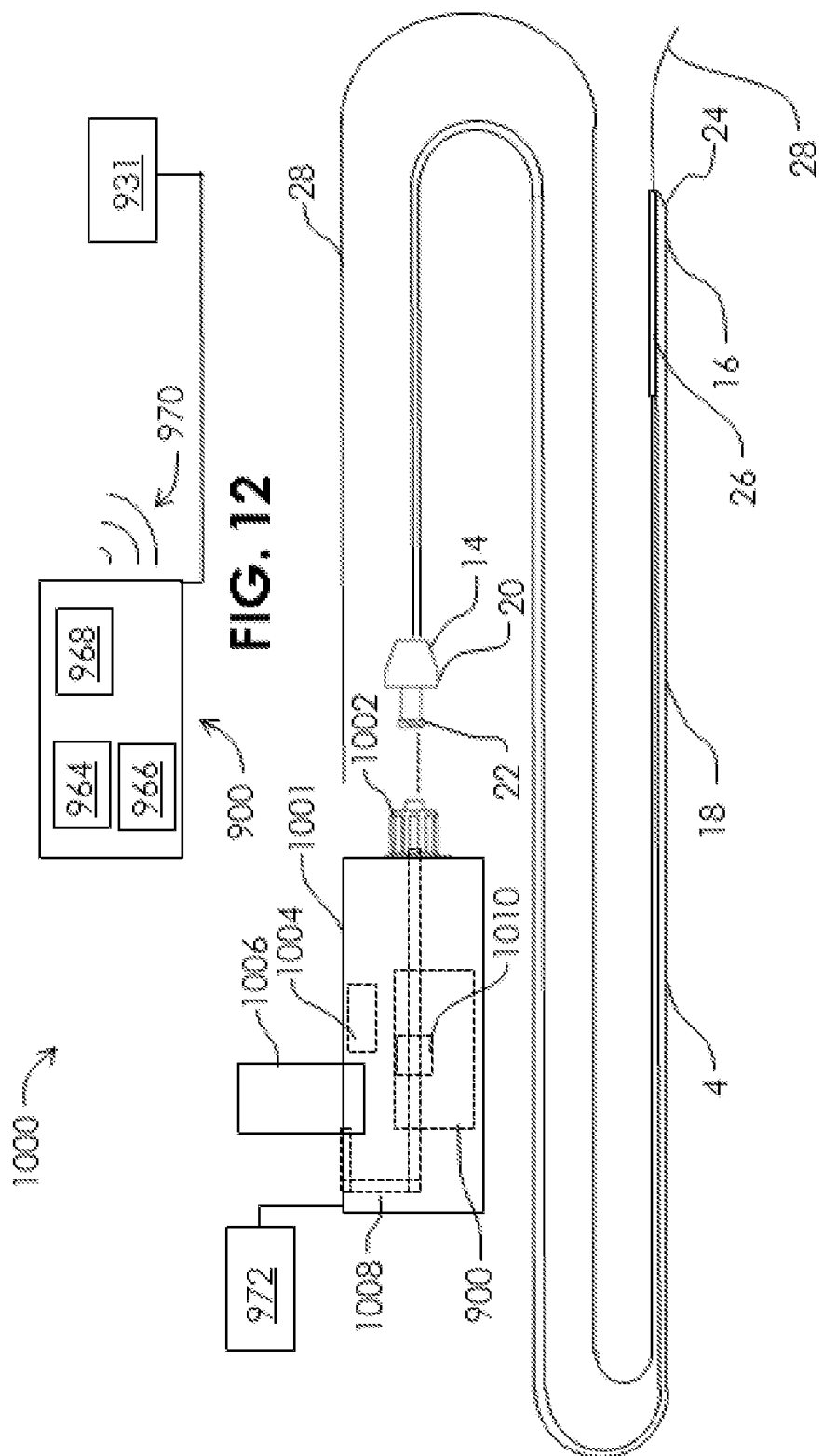

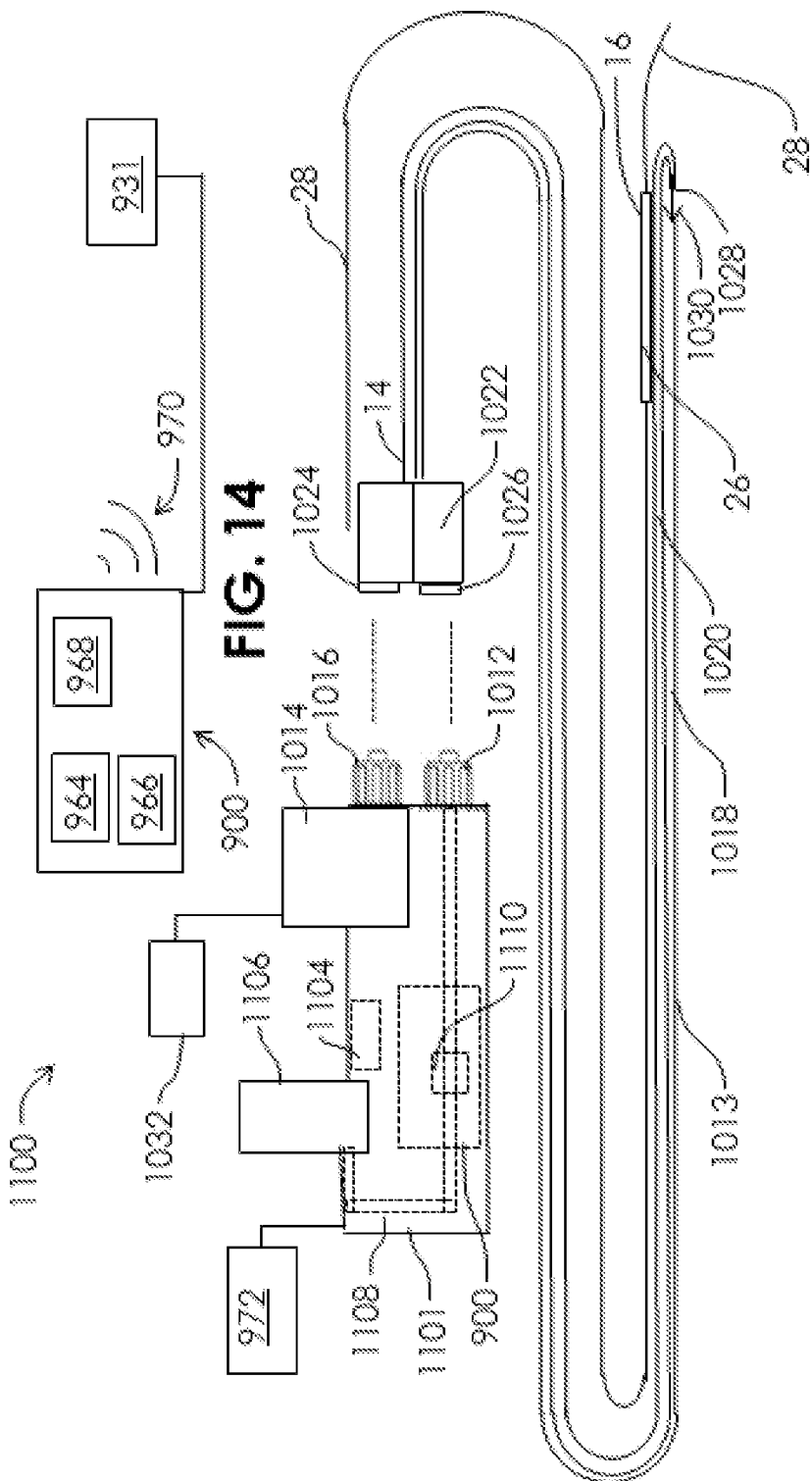

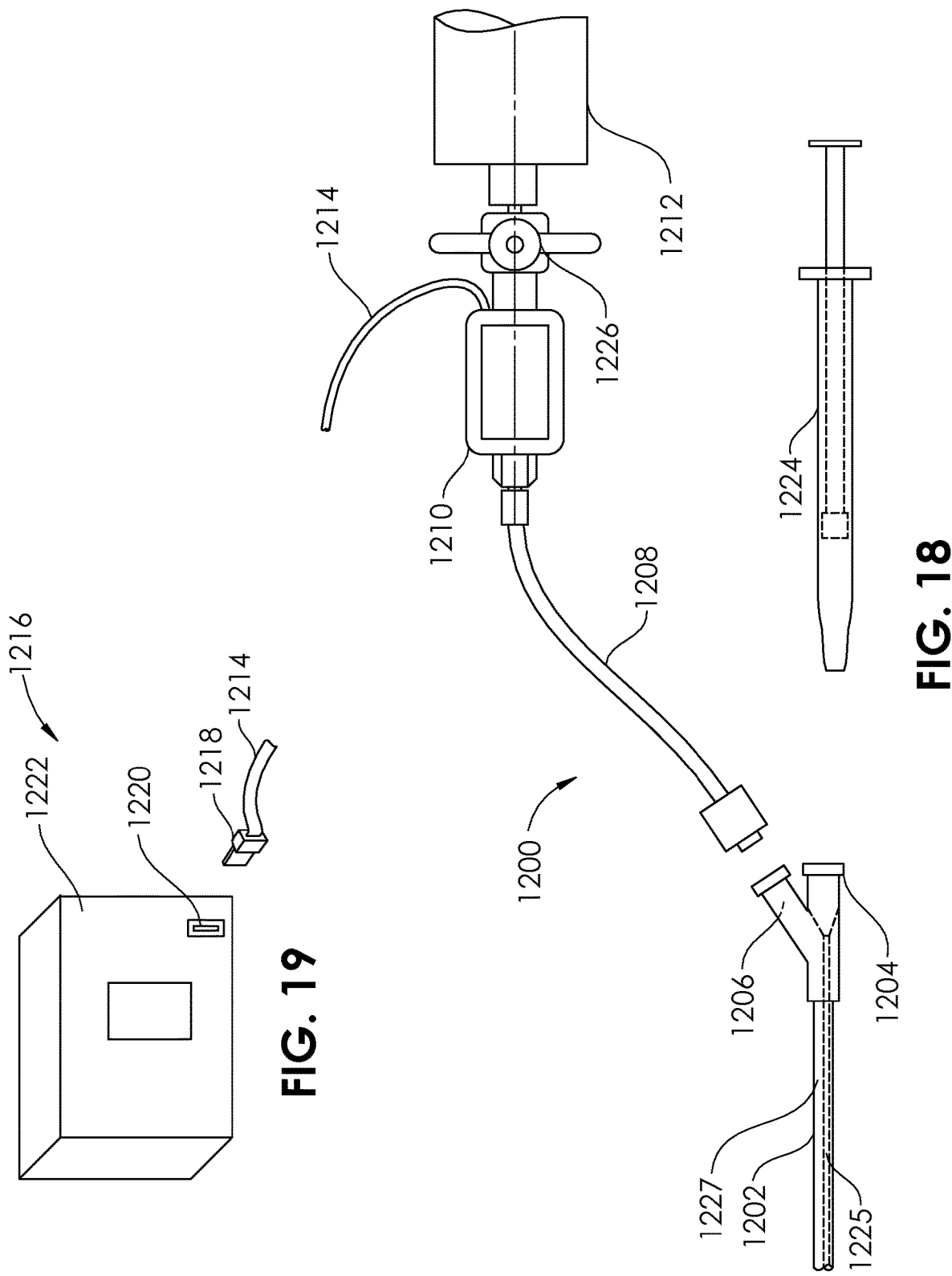

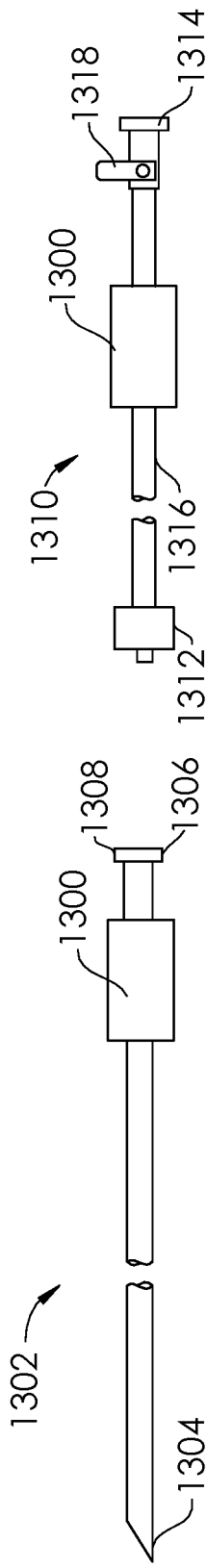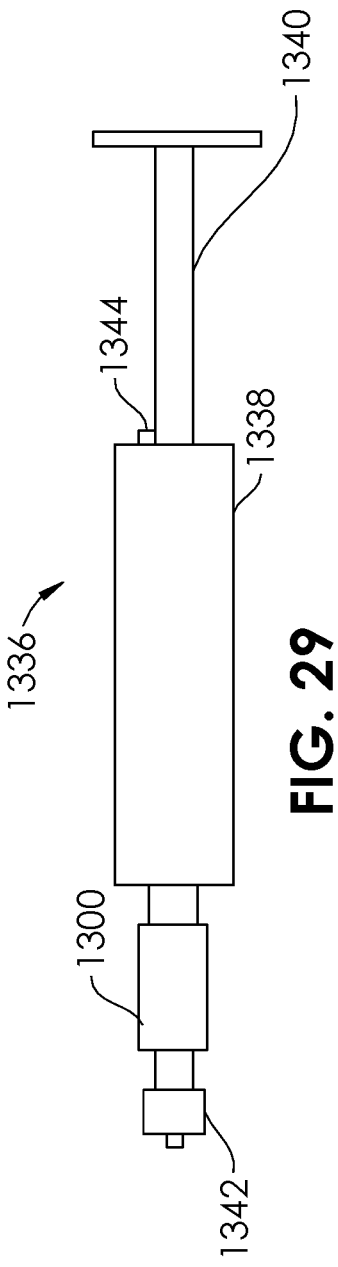

ASPIRATION MONITORING SYSTEM AND METHOD

INCORPORATION BY REFERENCE TO ANY PRIORITY APPLICATIONS

This application is a continuation of U.S. patent application Ser. No. 15/245,124, filed Aug. 23, 2016, now U.S. Pat. No. 10,702,292, which claims the benefit of priority to U.S. Provisional Application No. 62/211,637, filed on Aug. 28, 2015, U.S. Provisional Application No. 62/213,385, filed on Sep. 2, 2015, U.S. Provisional Application No. 62/239,795, filed on Oct. 9, 2015, U.S. Provisional Application No. 62/239,953, filed on Oct. 11, 2015, and U.S. Provisional Application No. 62/318,388, filed on Apr. 5, 2016, all of which are herein incorporated by reference in their entirety for all purposes. Priority is claimed pursuant to 35 U.S.C. § 120 and 35 U.S.C. § 119

BACKGROUND OF THE INVENTION

Field of the Invention

The field of the invention generally relates to an aspiration system for removing, by aspiration, undesired matter such as a thrombus from a fluid carrying cavity, duct, or lumen of the body, such as a blood vessel.

Description of the Related Art

A treatment method for removing undesired matter such as thrombus from a blood vessel of a patient involves use of an aspiration catheter having elongate shaft formed with an aspiration lumen extending therein. An aspiration catheter may also include a guidewire lumen for placement of a guidewire, which is used to guide the aspiration catheter to a target site in the body. By applying a vacuum (i.e. negative pressure) to a proximal end of the aspiration lumen, for example, with a syringe having a hub that is connected to the proximal end of the aspiration catheter, the matter can be aspirated into an aspiration port at the distal end of the aspiration catheter, into the aspiration lumen, and thus be removed from the patient.

SUMMARY OF THE INVENTION

In one embodiment, a system for real time monitoring of catheter aspiration includes a pressure sensor configured for placement in fluid communication with a lumen which at least partially includes an aspiration lumen of a catheter, the aspiration lumen configured to couple to a vacuum source, a measurement device coupled to the pressure sensor and configured for measuring deviations in fluid pressure, and a communication device coupled to the measurement device and configured to generate a continuous signal which is proportional to measured fluid pressure.

In another embodiment, a system for real time monitoring of catheter aspiration includes a pressure sensor configured for placement in fluid communication with an aspiration lumen of a catheter, the aspiration lumen configured to couple to a vacuum source, a measurement device coupled to the pressure sensor and configured for measuring variations in fluid pressure, and a communication device coupled to the measurement device and configured to generate a continuous signal which varies proportionally as a result of variation in fluid pressure.

BRIEF DESCRIPTION OF THE DRAWINGS

FIG. 3 is a view of an aspiration monitoring system according to a third embodiment of the present disclosure.

FIG. 11 is a plan view of a system for aspiration according to another embodiment of the present disclosure.

FIG. 12 is a detailed view of an aspiration monitoring system of the system for aspiration of FIG. 11.

FIG. 13 is a plan view of a system for aspiration according to another embodiment of the present disclosure.

FIG. 14 is a detailed view of an aspiration monitoring system of the system for aspiration of FIG. 13.

FIG. 18 is a plan view of a portion of a multi-purpose system according to an embodiment of the present disclosure.

FIG. 19 is a perspective view of a proximal portion of the multi-purpose system of FIG. 18.

FIG. 25 is a plan view of an aspiration catheter according to an embodiment of the present disclosure.

FIG. 26 is a plan view of a tubing set according to an embodiment of the present disclosure.

FIG. 27 is a plan view of a stopcock according to an embodiment of the present disclosure.

FIG. 28 is a plan view of a stopcock according to an embodiment of the present disclosure.

FIG. 29 is a plan view of a vacuum source according to an embodiment of the present disclosure.

DETAILED DESCRIPTION OF THE ILLUSTRATED EMBODIMENTS

Figure 1:
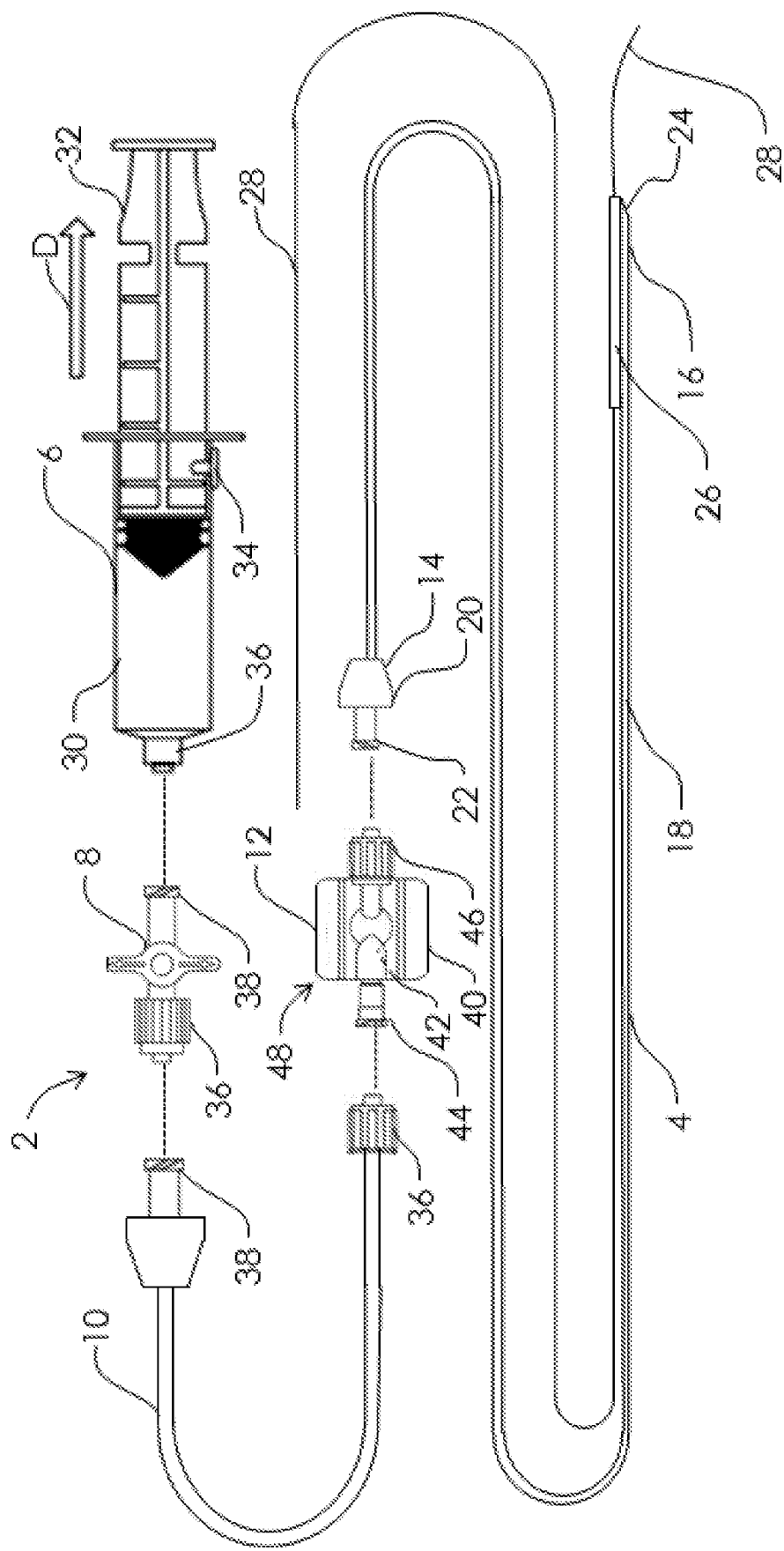
FIG. 1 is a plan view of a system for aspiration according to an embodiment of the present disclosure.

The present disclosure relates to aspiration catheter systems and monitoring, warning and communication systems for aspiration catheter systems. Clogging of aspiration catheters, for example by large pieces of thrombus, is a common concern for users. Techniques to avoid clogging/choking of material within the catheter often involve rapidly, aggressively advancing the aspiration catheter or gently plucking at edges of a thrombus to insure only small pieces or portions are introduced at a time, pieces which are small enough to not clog or occlude the aspiration lumen. When a device becomes clogged during use, the potential for inadvertent dislodgment of thrombus downstream increases; this is referred to as distal embolism. As aspiration procedures of this type are often used in highly technical emergent settings, early clog detection of the aspiration catheter for the user during aspiration can contribute to the success of the procedure and clinical outcome. Some sources have reported that up to 50% of aspiration catheters used get clogged during use.

The user may have difficulty determining whether there is a vacuum in the system or not. For example, the user may have difficulty determining whether the vacuum has been applied or not (e.g., the vacuum source has been turned on or off). Additionally, the user may have difficulty determining whether there has been a loss of vacuum in the system, for example because of the syringe (or other vacuum source) being full of fluid or because of a leak in the system. Blood is relatively opaque and can coat the wall of the syringe, thus making it difficult to determine when the syringe becomes full. This makes it difficult to determine whether sufficient vacuum is being applied to the aspiration catheter. The vacuum level may change to an unacceptable level even before the syringe becomes full. Extension tubing or other tubing may also cause a loss in vacuum in the system. Certain tubing kinks may be difficult for a user to see or identify. It is also difficult to determine whether there is an air leak in the system, which can be another cause for a loss of vacuum even before the syringe becomes full of the aspirated fluid.

During the aspiration of thrombus with an aspiration catheter, it is difficult to identify when thrombus is actively being aspirated, or when only blood is being aspirated. Typically, it is desired to not aspirate sizable quantities of normal blood from blood vessels, because of the importance of maintaining normal blood volume and blood pressure. However, when tracking the tip of an aspiration catheter in proximity to a thrombus, it is difficult to know whether the aspiration catheter has actively engaged a thrombus, whether it has aspirated at least a portion of the thrombus, or whether it is not engaged with the thrombus, and is only aspirating blood. Though some aspiration catheters, such as those used in the peripheral blood vessels or in an arteriovenous fistula, may be around 50 cm or even less, the tip of an aspiration catheter may in same cases be more than 90 cm from the hands of the user, or as much as 135 cm from the hands of the user, or in some cases as much as 150 cm, and the particular status of vacuum at the tip of the catheter is often not known by the user. A user may thus be essentially plunging a catheter blindly without significant, usable sensory feedback. The catheter may have an outer diameter up to or even greater than 6 French, and may be as high as 10 French or greater. The increased catheter outer diameter can cause some concern of potential trauma inside a blood vessel. The use of aspiration catheters can therefore be inefficient, and cause more blood removal than desired, causing a user to minimize the length of the therapy and in severe cases necessitating blood transfusion. An increased volume of normal blood being aspirated also means that the vacuum source (e.g. syringe) will fill in a shorter amount of time, thus requiring more frequent replacement of the vacuum source. Distal embolism may occur if the vacuum pressure is not sufficient, and yet the user is not aware.

In some cases, a syringe that is completely or mostly full or blood and/or thrombus may continue to be used, though in this state, there is not sufficient pressure to effectively aspirate thrombus or unwanted material, thus causing inefficient use of time, and lengthening the procedure. In some cases, the user may not realize the plunger of the syringe has mistakenly not been pulled back (to evacuate the syringe). In some cases, the syringe itself may be defective, and a proper vacuum may not be achieved, without the user being aware. In some cases, kinked tubing, lines, or catheters may go unnoticed, because of bad visibility in a procedural laboratory, or simply from the extent of concurrent activities being performed. In many cases, the user's eyes are oriented or focused on a monitor, for example a fluoroscopic monitor or other imaging monitor, or a monitor with patient vital data. Though the user may be able to view flow through transparent or partially transparent lumens (such as extension tubing), in dim lighting with intermittent viewing, it is difficult for the user's mind to process flow of an opaque liquid (such as blood/thrombus). Even in good lighting with a focused eye, the movement of fluid through extension tubing may not present an accurate picture of the aspiration status, as the visual flow effect may be delayed in relation to the applied vacuum. More than one medical device personnel may be sharing sensory information with each other to attempt to build a current status in each other's minds of the aspiration procedure. When a user relies on another's interpretation, especially when either are multitasking, a false sense of the status may occur. A syringe attached to the aspiration catheter may cause kinking, for example, if placed on an uneven surface. The distal opening in an aspiration lumen of an aspiration catheter may be prone to aspirating directly against the wall of a blood vessel, thus being temporarily stuck against the vessel wall, and stopping flow throughout the aspiration lumen. In some cases, a vacuum that is too large may be accidentally or inappropriately applied to the aspiration lumen of the aspiration catheter, limiting effectiveness (for example, if it causes the walls surrounding the aspiration lumen to collapse and thus, cut off the significantly decrease the flow through the aspiration lumen). The syringes which are sometimes used as a vacuum source to connect to an aspiration lumen of an aspiration catheter may malfunction, and not be fully actuated/evacuated. But, even when the syringe is functioning correctly, it will tend to fill up at difficult to predict moments, and thus commonly have periods with no applied vacuum. In the cases wherein a portion of clot/thrombus is being aspirated through the aspiration lumen, a significant pressure drop may occur at the current position of the thrombus, and thus, a sufficient vacuum may only exist from the proximal end of the aspiration lumen and distally up to the point of the thrombus. Thus, an insufficient vacuum may exist at the distal end of the aspiration lumen, e.g., at the distal end of the aspiration catheter. The same situation may occur if there is an actual clog at some intermediate point within the aspiration lumen. In either of these conditions, because of the insufficient vacuum at the distal end of the aspiration lumen, there may be a risk of thrombus or emboli being sent distally in the vasculature, which may cause occlusion, stroke, pulmonary embolism, or other disorders, depending upon the location of the intervention or procedure being performed. With current apparatus and techniques, these situations are very difficult to detect when they occur. It has been estimated that in as many as 50% of thrombus aspiration procedures, some sort of failure occurs.

An aspiration system 2 is illustrated in FIG. 1 and is configured to allow real time monitoring of catheter aspiration. The aspiration system 2 comprises an aspiration catheter 4, a vacuum source 6, a valve 8, extension tubing 10, and an aspiration monitoring system 48 including an in-line pressure transducer 12. The aspiration catheter 4 has a proximal end 14 and a distal end 16 and an aspiration lumen 18 extending from the proximal end 14 to the distal end 16. The aspiration lumen 18 may be sized for aspiration of thrombus, and in some embodiments may have an inner diameter of between about 0.38 millimeter (0.015 inches) and about 2.54 millimeters (0.100 inches). The aspiration catheter 4 includes a hub 20 at its proximal end which may include a female luer connector 22. The aspiration lumen 18 at the distal end 16 of the aspiration catheter 4 may include an angled orifice 24, which aids in the tracking through tortuous or occluded vasculature. In some embodiments, a guidewire lumen 26 is coupled to the distal end 16 of the aspiration catheter 4, and is configured to track over a guidewire 28. The vacuum source 6 may comprise a syringe, and may be sized between 5 ml and 100 ml, or between 20 ml and 60. The vacuum source 6 may comprise a VacLok® syringe, made by Merit Medical, South Jordan, Utah. The vacuum source 6 may include a barrel 30 and plunger 32, with a lock 34 which is configured to retain the plunger 32 in position in relation to the barrel 30, for example, when the plunger 32 is pulled back in direction D to create a negative pressure (vacuum) inside the barrel 30. In some embodiments, the vacuum source 6 may comprise any other type of evacuatable reservoir, or may comprise a vacuum pump. The vacuum source 6 is connected to the aspiration lumen 18 of the aspiration catheter 4 via the extension tubing 10 and the valve 8. In some embodiments, the vacuum source 6 may be connected directly to the aspiration lumen 18 of the aspiration catheter 4. Male luer connectors 36 and female luer connectors 38 are indicated in FIG. 1. The valve 8 may be a standard two-way stopcock, as illustrated.

Figure 2A:
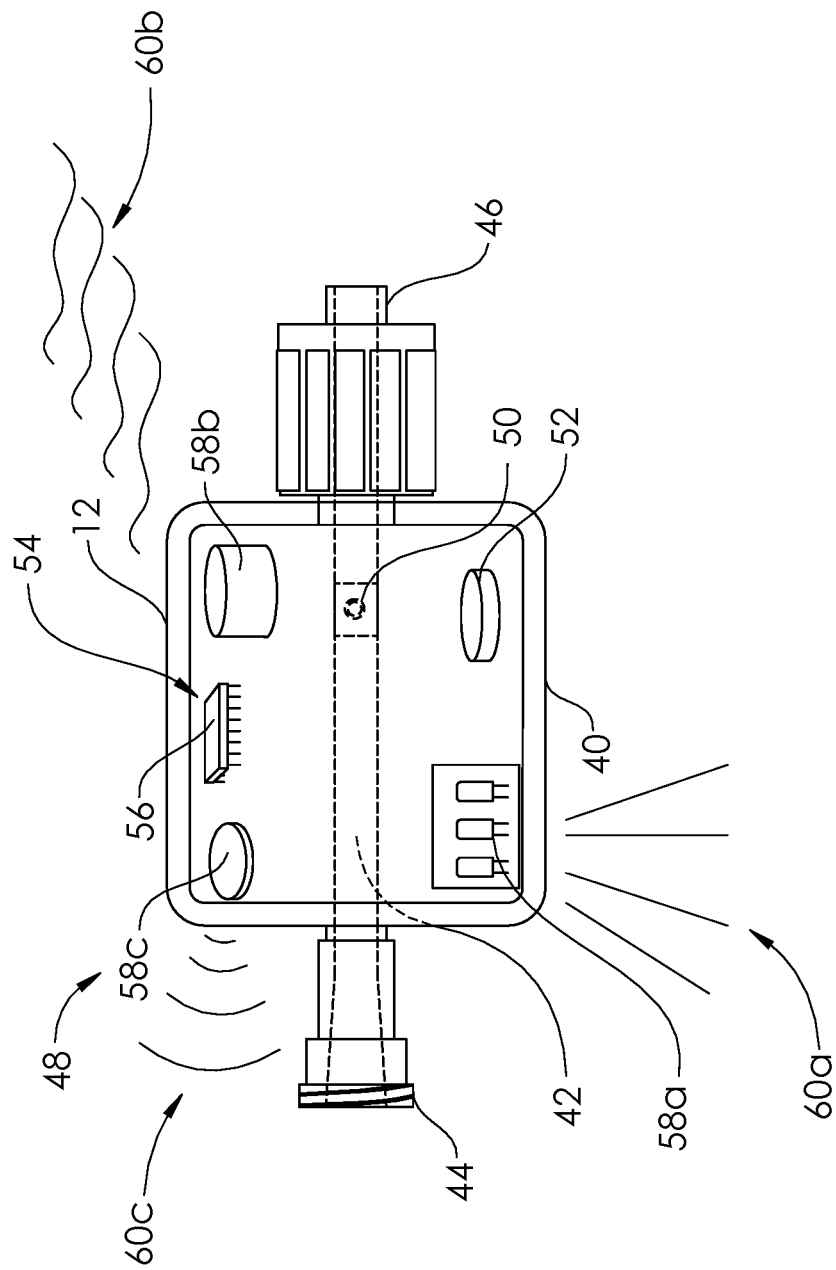
FIG. 2A is a view of an aspiration monitoring system according to a first embodiment of the present disclosure.

The pressure transducer 12 of the aspiration monitoring system 48 is configured to be fluidly coupled between the vacuum source 6 and the aspiration catheter 4. In FIG. 2A, the aspiration monitoring system 48 is illustrated as a self-contained device of a first embodiment. The pressure transducer 12 comprises a housing 40 having a cavity 42 extending between a first port 44 and a second port 46. In some embodiments, the first port 44 comprises a female luer and the second port 46 comprises a male luer. In some embodiments, the first port 44 comprises a female luer lock and the second port 46 comprises a male luer lock, each of which is attachable to and detachable from a corresponding luer lock of the opposite gender. The first port 44 is configured to be coupled to the vacuum source 6, either directly, or with the valve 8 and/or extension tubing 10 connected in between. The second port 46 is configured to be coupled to the aspiration lumen 18 of the aspiration catheter 4, for example, by coupling the second port 46 directly or indirectly to the hub 20 of the aspiration catheter 4. When the aspiration system 2 is used to aspirate body fluids and/or materials, for example blood and/or thrombus, the body fluids and/or materials are aspirated through the aspiration lumen 18 of the aspiration catheter from the angled orifice 24 at the distal end 16 to the female luer connector 22 at the proximal end 14, then pass through the second port 46 of the pressure transducer 12 first, through the cavity 42, and then through the first port 44. Depending on the amount of amount of vacuum (negative pressure) applied by the vacuum source 6, and the amount of flow resistance and resulting pressure drop along the aspiration system 2, the pressure within the cavity 42 will vary. For example, a more viscous fluid like blood, or a fluid having solid, semi-solid, or gel-like particles or portions, will cause more flow resistance through the relatively small aspiration lumen 18 of the aspiration catheter 4 than would water or normal saline solution. Thus the pressure within the cavity 42 of the pressure transducer 12 will decrease (the amount of vacuum will increase) as the flow resistance in the aspiration lumen 18 increases.

For definition purposes, when speaking of the amount of vacuum, a pressure of, for example, −15,000 pascal (−2.18 pounds per square inch, or psi) is a "larger vacuum" than −10,000 pascal (−1.45 psi). Additionally, −15,000 pascal is a "lower pressure" than −10,000 pascal. Furthermore, −15,000 pascal has a larger "absolute vacuum pressure" than does −10,000 pascal, because the absolute value of −15,000 is larger than the absolute value of −10,000. In FIG. 2A, a vacuum sensor 50 is disposed within the cavity 42 of the housing 40 and is in fluid communication with fluid that passes through the cavity 42. The vacuum sensor 50 may be a standard pressure sensor or transducer, including a pressure sensor designed primarily for measuring positive pressure. It may use any type of pressure sensing technology known in the art, including MEMS Technology. In some embodiments, the vacuum sensor 50 is configured for highest accuracy and/or precision within the range of pressures between about 0 pascal to about −101,325 pascal (−14.70 psi), or between about −45,000 pascal (−6.53 psi) and about −90,000 pascal (−13.05 psi), or between about −83,737 pascal (−12 psi) and about −96,527 pascal (−14 psi). In some embodiments, the power requirement for the vacuum sensor may range from 2.5 volts DC to 10 volts DC. In some embodiments, the vacuum sensor 50 may be an analog gauge with an output voltage. In the self-contained embodiment of the FIG. 2A, the vacuum sensor 50 is powered by one or more battery 52. Based on the power requirements of the vacuum sensor 50, and the power requirements of other components of the aspiration monitoring system 48 described herein, in some embodiments the one or more battery 52 may range between 1.5 volts and nine volts. Also contained within the housing is a measurement device 54, which in some embodiments may comprise a microprocessor. The measurement device 54 is coupled to the vacuum sensor 50 and receives signals from the vacuum sensor 50 indicative of real time measured pressure. In some embodiments, the measurement device 54 includes a memory module 56 in which information is stored that may be used by the measurement device 54, for example, in calculations. Information may include, for example, an array of one or more pressure values. In some embodiments, the array of one or more pressure values may be correlated with one or more different corresponding system models or catheter models. The vacuum sensor 50 may be used in some cases for detecting the presence or amount of vacuum alone, for the purpose of monitoring whether the vacuum source 6 (e.g., syringe) is significantly full, and thus needs to be changed. The vacuum sensor 50 may be used in some cases for detecting whether there is a vacuum in the system of not. For example, whether the vacuum has been applied or not (e.g., the vacuum source has been turned on or off).

One or more communication devices 58a, 58b, 58c are included within the aspiration monitoring system 48 and are coupled to the measurement device 54. Each of the one or more communication devices 58a-c are configured to generate a type of alert comprising an alert signal 60a-c, in response at least in part to activity and output of the measurement device 54. In some embodiments, the communication device 58a may include one or more LEDs (light emitting diodes) configured to generate a visible alert via a visible alert signal 60a, such as light that is continuously illuminated, or is illuminated in a blinking pattern. In some embodiments, the LEDs may be oriented on multiple sides of the communication device 58a, so that they may be easily seen from a variety of different locations. In some embodiments, lights other than LEDs may be used. Light pipes or other lighting conduits may also be incorporated in embodiments, to further place visual indicators at multiple locations and/or orientations. In some embodiments, the communication device 58b may include one or more vibration generators configured to generate a tactile alert via a tactile alert signal 60b, which may include, but is not limited to, vibration or heat. In some embodiments, the vibration device may be similar to a video game controller. In some embodiments, the vibration generator may comprise a piezoelectric device which is configured to vibrate when a voltage is applied. In some embodiments, the communication device 58c may include one or more sound generating devices configured to generate an audible alert via an audible alert signal 60c, such as a continuous noise, or a repeating noise. The communication device 58c in some embodiments may comprise a loudspeaker for generation of any variety of sounds, at any variety of frequencies (Hz) or sound pressures (dB) within the human audible range and/or human tolerance range. The communication device 58c may even be configured to generate sounds that are outside the human audible range in embodiments wherein the signal is intended to be felt as a vibration or other tactile sensation, instead of an audible sensation. In some embodiments, the sound generating device may comprise a buzzer which is configured to sound one or more audible pitches when a voltage is applied. In some embodiments a piezoelectric device, such as that described in relation to the communication device 58b may also serve as a sound generating device, included as communication device 58c. The alert signal 60a-c can at times serve as a "wake up" alarm for the user, in cases where the user has become too focused on other factors during the procedure.

A user of an aspiration system 2 may desire to be notified of several conditions which may occur during use of the aspiration system 2. These potential conditions include, but are not limited to clogging, a loss of vacuum due to filling of the vacuum source 6 and or a breach, break or puncture in the aspiration system 2, and the engagement or aspiration of non-fluid, solid or semi-solid material such as thrombus. The aspiration monitoring system 48 of FIG. 2A is configured to alert users of an aspiration system 2 about real time status of the aspiration system 2, including operational conditions, which include: whether vacuum is being applied or not; flow conditions, which include whether a thrombus is engaged, whether a thrombus is being actively aspirated, whether the system is leaking air, whether the system is clogged, whether the vacuum source 6 is full and/or needs to be changed; or other potential set up issues. The real time feedback provided frees a user or operator from the need of excessive personal monitoring of the vacuum source 6, extension tubing 10, or other portions of the aspiration system 2, for improper or undesired flow or operation conditions, and thus allows the user to focus more attention on the patient being treated. The user is kept aware of whether a clot is being aspirated or has been aspirated, or whether there is a clog. Additionally, the user is kept aware of whether there is too large an amount of blood being removed from the patient, or whether there are fault conditions like system leak or tubing kink. A tubing kink distal to the vacuum sensor 50 may be identified (for example by an increase in measured vacuum) and a tubing kink proximal to the vacuum sensor 50 may be identified (for example, by a loss or degradation of vacuum). In some cases, the user may attempt to operate the catheter with a vacuum source 6 that is already full (and thus has no significant vacuum). In some cases, a user may even forget to open the valve 8 to begin suction, but the aspiration monitoring system, 48 can also identify that the system is not yet functioning, and communicate a list of potential errors or specific errors (for the particular pressure waveform measured). By having the real-time awareness of the many factors related to the operating status, the procedure is made safer, the time of the procedure may be reduced, and blood loss may be reduced.

The pressure transducer 12 of the aspiration monitoring system 48 is configured to continuously measure and monitor the absolute pressure amplitude within the closed system of the aspiration system 2, and also is configured to measure and monitor the relative pressure over time to detect noteworthy flow changes within the flow circuit of the aspiration system 2. Some changes are discernible via absolute pressure measurement, while more subtle pressure deflections may be compared to a stored library in memory. Noteworthy conditions may be signaled to the user when appropriate. In some embodiments, the unfiltered signal may be amplified by an amplifier and filtered by a filter, for example, to increase the signal-to-noise ratio. Examples of the (background) noise 57 in an unfiltered signal can be seen in FIGS. 5A-5D (labeled in FIG. 5A). In some embodiments, one or more algorithms may be used, as described herein, to identify particular conditions of interest.

Figure 2B:
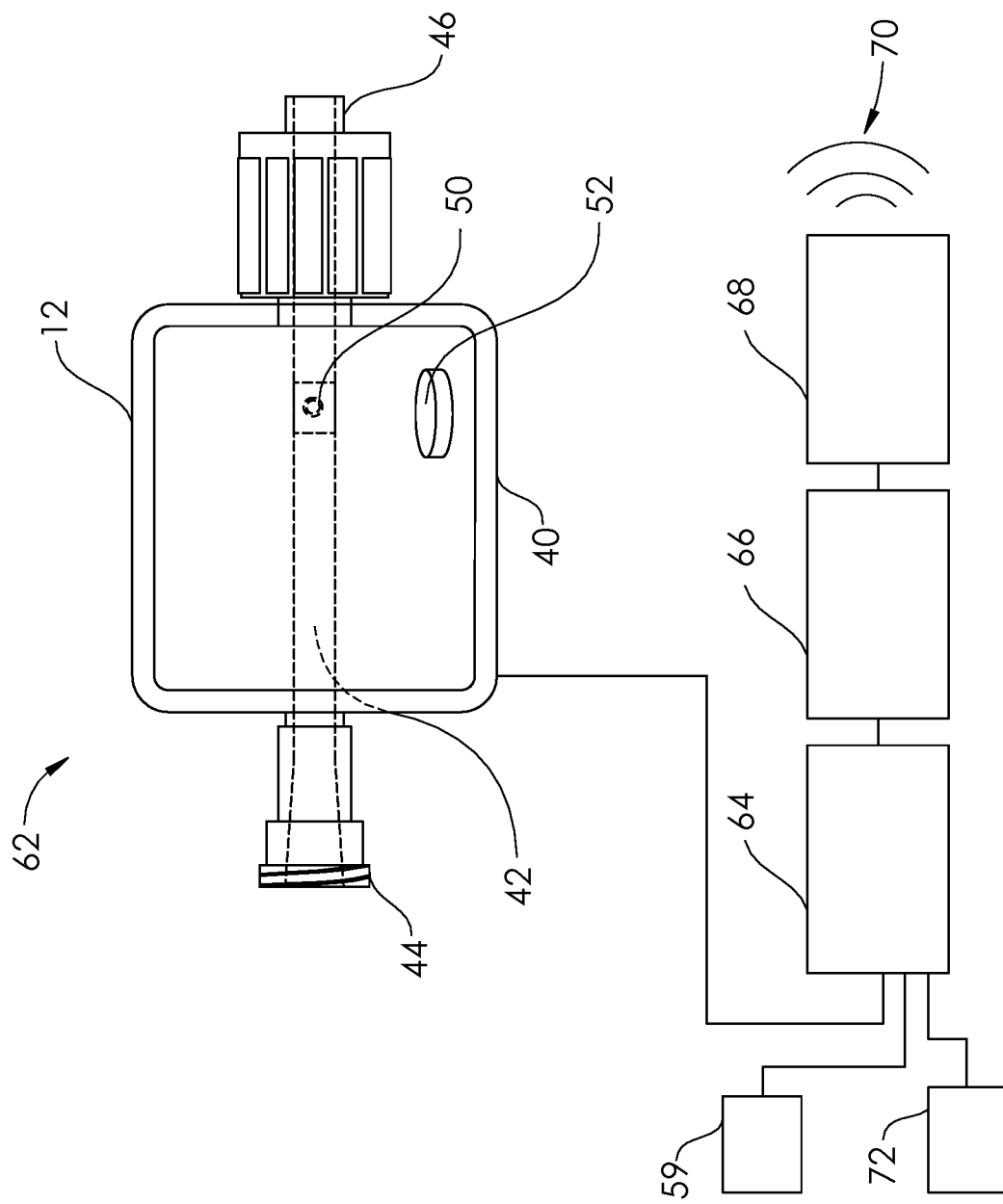
FIG. 2B is a view of an aspiration monitoring system according to a second embodiment of the present disclosure.

FIG. 2B illustrates a second embodiment of an aspiration monitoring system 62 having a pressure transducer 12 having a vacuum sensor 50 disposed within the cavity 42 of a housing 40. The vacuum sensor 50 may be powered by at least one battery 52. In some embodiments, the pressure transducer 12 may be reusable, and may be configured to allow charging of the battery 52, or of a capacitor (not shown) by direct charging methods, or by inductive power transfer methods and devices known in the art. Unlike the aspiration monitoring system 48 of FIG. 2A, the aspiration monitoring system 62 of FIG. 2B comprises a measurement device 64, memory module 66, and communication device 68 which are external to the pressure transducer 12. A power module 72, also external, may be used to power any of the measurement device 64, memory module 66, or communication device 68. The communication device 68 may be any of the communication device 58a, 58b, 58c described in relation to the aspiration monitoring system 48 of FIG. 2A, and are configured to product an alert via an alert signal 70. The communication device 68 may be portable so that it may be positioned close to the user.

In some embodiments, the communication device 68 may be wearable by the user. FIG. 3 illustrates an aspiration monitoring system 78 which includes an antenna 80 coupled to a measurement device 76. The measurement device 76 is similar to the measurement device 54 of prior embodiments, except that it wirelessly sends a communication signal 84 via the antenna 80 to a corresponding antenna 82 of a communication device 74. In some embodiments, the communication device 74 comprises a wristband which the user wears, and which may include a vibration generator or heat generator. In some embodiments, the communication device 74 comprises an audio speaker which may be attached to equipment or even to the patient or user. In some embodiments, the communication device 74 comprises an audio speaker on an earpiece or earbud that the user may wear. In some embodiments, Bluetooth® communication technology may be used. The real time feedback supplied by the aspiration monitoring system 62 may decrease the time that the aspiration system 2 is actively aspirating without being engaged with a thrombus, thus minimizing the amount of non-thrombotic blood lost by aspiration. This may be particularly beneficial in larger bore catheters, for example in catheters having a diameter of 7 French or larger. The real time feedback may also minimize the amount of total time that catheters are tracked back-and-forth through the blood vessels, minimizing potential damage to the intima of the blood vessels, dissection of the blood vessels, or distal embolization. By lowering the risk of the aspiration catheter tip getting caught (via suction) against the blood vessel wall, the distal end of the aspiration lumen may be more aggressively designed for optimized aspiration characteristics. The technique of using the aspiration catheter may additionally be able to be performed in a more sophisticated manner, with continual or continuous knowledge of the vacuum status. For example, a piece of thrombus may be aspirated, followed by a "chaser" of blood aspiration, followed by another piece of thrombus, etc.

Figure 4A:
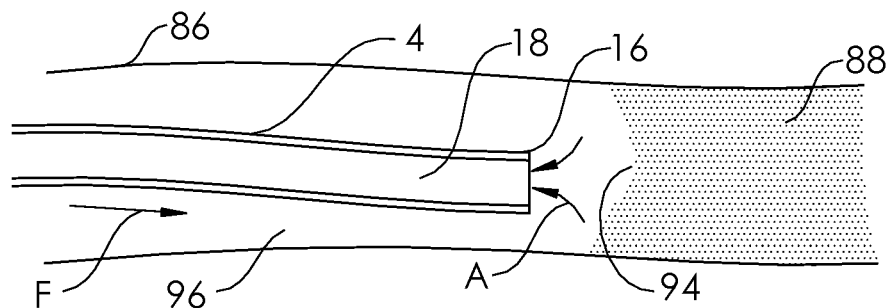
FIG. 4A is a sectional view of an aspiration catheter in a blood vessel prior to contact with a thrombus.
Figure 5A:
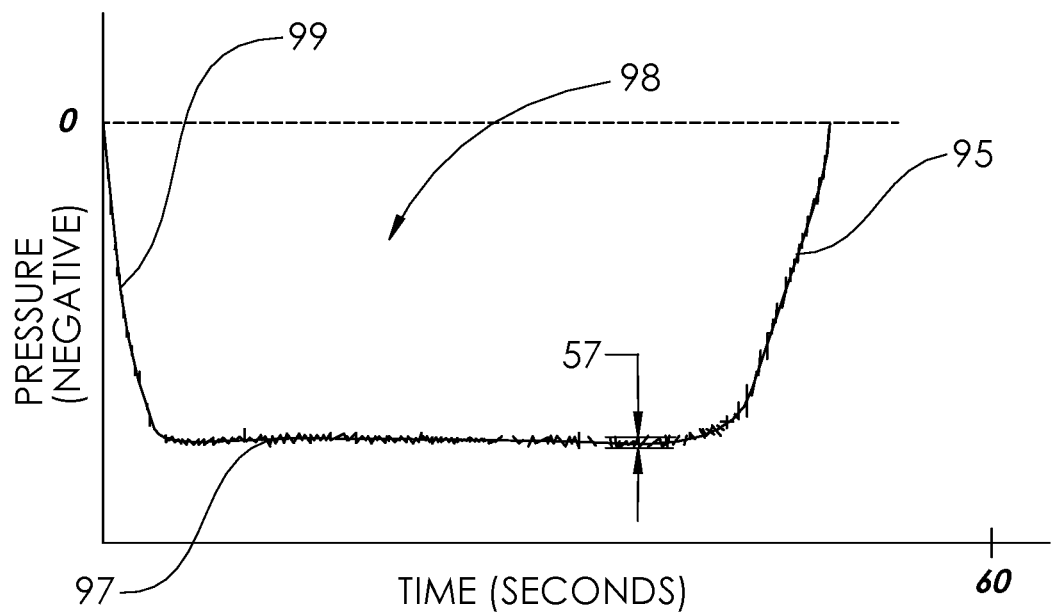
FIG. 5A is a graphic representation of pressure vs. time for the condition of FIG. 4A.

FIG. 4A illustrates the distal end 16 of an aspiration catheter 4 within a blood vessel 86 having at least one thrombus 88. The aspiration catheter 4 is being advanced in a forward direction F, but the distal end 16 of the aspiration catheter 4 has not yet reached the proximal extremity 94 of the thrombus 88. A vacuum source 6 (FIG. 1) has been coupled to the aspiration lumen 18 of the aspiration catheter 4 and activated (i.e. the valve 8 is open) causing blood 96 to be aspirated into the aspiration lumen 18 (arrows A). Turning to FIG. 5A, a corresponding curve 98 is represented for the normal fluid (e.g. blood) vacuum over time for the condition of FIG. 4A. The curve 98 represents vacuum pressure over time sensed by the vacuum sensor 50 of any of the embodiments presented. No leaks are present and no thrombus is being evacuated, and therefore the curve 98 includes a downward slope 99 when the vacuum source 6 increases the vacuum up (lowers the pressure) within the cavity 42 of the pressure transducer 12 to a relatively steady state. The steady pressure curve 97 continues while blood 96 is being aspirated. As the vacuum is decoupled from the aspiration lumen 18, for example by closing the valve 8 or by detaching any two of the ports (e.g. luers), or if the vacuum source 6 fills completely with blood 96, then an upward slope 95 is measured.

The measurement device 54, 64 is configured to compare the curve 97 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Thrombus encountered," or "No thrombus encountered." A different type of sound may be used for each of a plurality of "modes": "Thrombus encountered," "Actively flowing," and "No Vacuum." For example, a buzzing sound for "Thrombus encountered," a beep for "No vacuum," etc. The various characteristics of sound that may be varied include, but are not limited to timbre, or sound quality, spectrum, envelope, duration, phase, pitch (frequency), number of sounds (repetition). Communication device 58c may vibrate or heat in a characteristic pattern, for example, a certain number of repetitions or a certain frequency between repetitions. The user may determine that an additional fluoroscopic image (e.g. angiography) or other imaging modalities may be necessary to better identify the location of the thrombus 88.

Figure 4B:
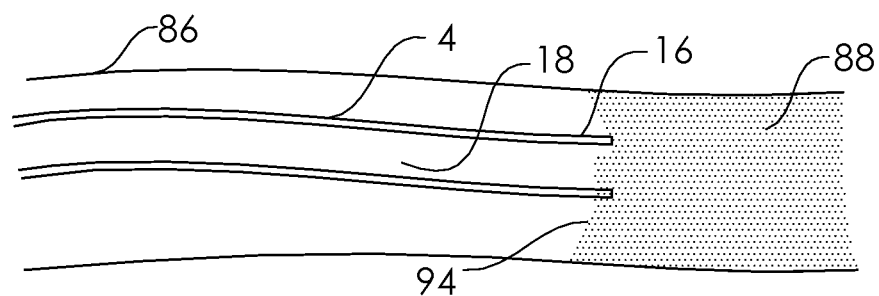
FIG. 4B is a sectional view of an aspiration catheter in a blood vessel upon contact with a thrombus.
Figure 5B:
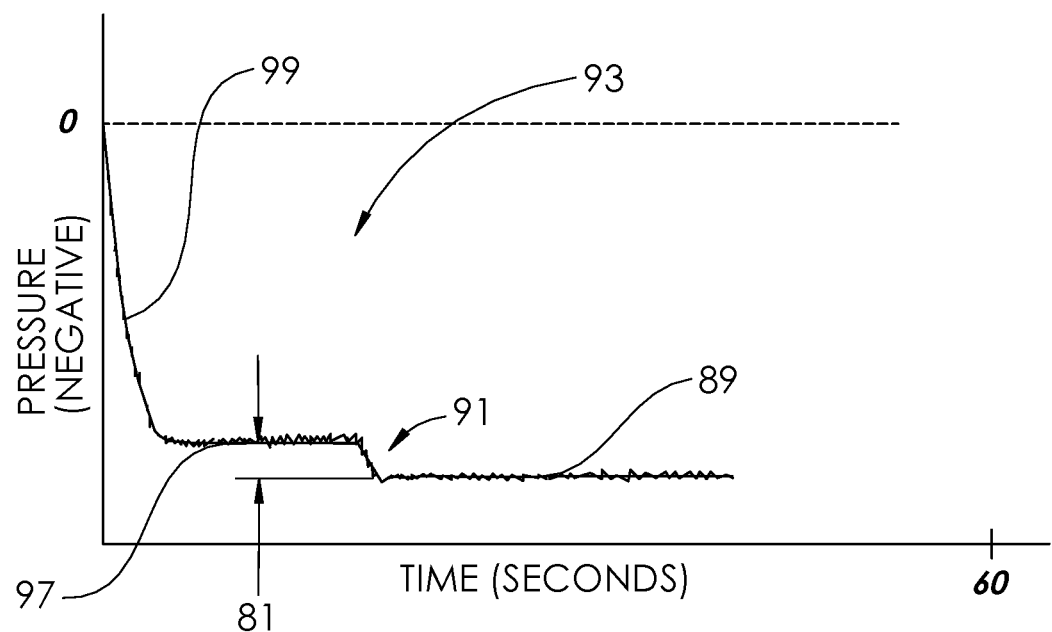
FIG. 5B is a graphic representation of pressure vs. time for the condition of FIG. 4B.
Figure 5C:
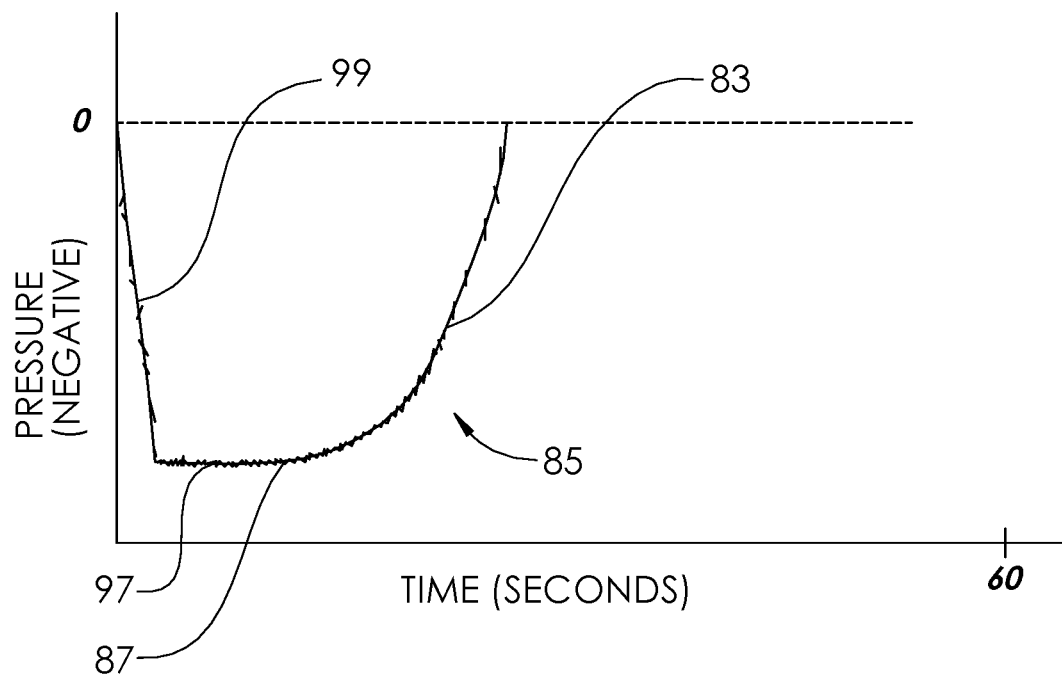
FIG. 5C is a graphic representation of pressure vs. time for the condition of FIG. 4C.

FIG. 4B illustrates the distal end 16 of an aspiration catheter 4 advanced to a position such that the distal end 16 of the aspiration catheter 4 contacts the proximal extremity 94 of the thrombus 88. The corresponding curve 93 in FIG. 5B represents vacuum pressure over time sensed by the vacuum sensor 50 of any of the embodiments presented. The curve 93 initially has a downward slope 99 followed by a steady pressure curve 97, as in the condition of FIG. 4A, graphed in FIG. 5A, however, when the distal end 16 of the aspiration catheter 4 contacts the proximal extremity 94 of the thrombus 88, if the aspiration causes a portion of the thrombus 88 (for example a large or relatively hard portion)

to enter and become trapped in the aspiration lumen 18, then a clog condition occurs. A similar condition occurs if the distal end 16 of the aspiration catheter 4 is caught on the thrombus 88 by the vacuum, with virtually nothing flowing through the aspiration lumen 18. In either condition, the curve 93 includes a deviation (or disturbance) in fluid pressure 91. If the clog (or stuck condition) continues, then a flat, depressed pressure 89 is measured.

The measurement device 54, 64 is configured to compare the curve 93 with information stored in the memory module 56, 66 to identify this condition. In some embodiments, the measurement device 54, 64 uses an algorithm to make the comparison. In some embodiments, a pre-set pressure differential $\Delta P_1$ may be stored in the memory module 56, 66 as a threshold, whereby the measurement of a pressure difference 81 less than this threshold does not result in the measurement device 54, 64 commanding the communication device 58a-c, 74 to send an alert signal 60a-c, 70. In some embodiments, when the pressure difference 81 is greater than (or greater than or equal to) the pre-set pressure differential $\Delta P_1$, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Clog Condition." Communication device 58c may vibrate or heat in a characteristic pattern, for example, a certain number of repetitions or a certain frequency between repetitions. When the user realizes that the clog condition is present, the user may pull on the aspiration catheter 4 and readvance it, in an attempt to contact a portion of the thrombus 88 that can be aspirated. If a portion of the thrombus is clogged in the aspiration lumen 18, and repositioning of the aspiration catheter 4 does not produce good results, the aspiration catheter 4 can be removed and the aspiration system 2 can be repurged, for example by a positive pressurization.

Figure 4C:
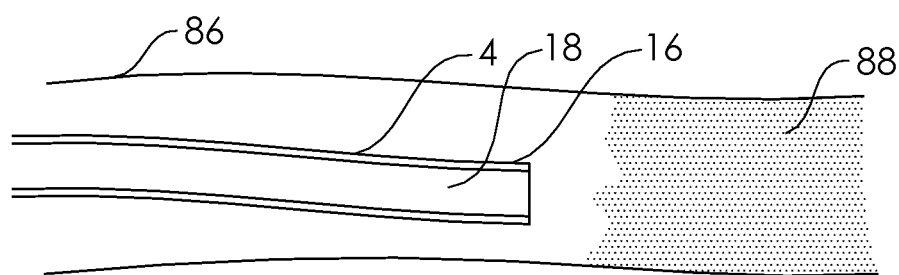
FIG. 4C is a sectional view of an aspiration catheter during a loss of vacuum.

FIG. 4C illustrates the distal end 16 of the aspiration catheter 4 in a general situation during which a breach in the aspiration system 2 has occurred. For example, a break, leak, puncture, pinhole, loosening, or disconnection may cause air to be pulled into the aspiration lumen 18 of the aspiration catheter 4, the cavity 42 of the pressure transducer 12, of the interior of the extension tubing 10, valve 8, or vacuum source 6. As graphed in the curve 85 of FIG. 5C, a downward slope 99 and a subsequent steady pressure curve 97 are measured, but at the point in time of the breach 87 an upward slope 83 begins.

The measurement device 54, 64 is configured to compare the curve 85 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "System Leak." Communication device 58c may vibrate or heat in a characteristic pattern, for example, a certain number of repetitions or a certain frequency between repetitions. Upon receiving the alert, the user will check the components of the aspiration system 2 and either fix the breach or replace one or more of the components of the aspiration system 2. For example, in some cases, the communication device 58a-c, 74 may alert the user when the measurement device 54, 64 confirms a loss of vacuum, allowing the user to change or recharge the vacuum source 6, which has become depleted (e.g. by filling with blood and/or thrombus).

Figure 4D:
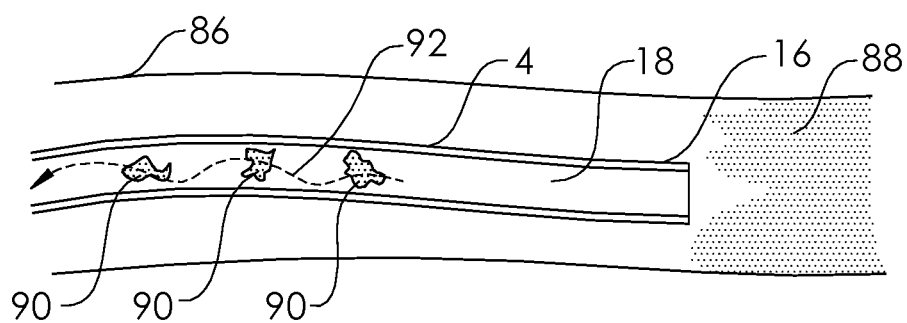
FIG. 4D is a sectional view of thrombi being aspirated through an aspiration catheter.

FIG. 4D illustrates the distal end 16 of the aspiration catheter 4 during the successful aspiration of pieces or portions 90 of the thrombus 88. In some cases, the pieces or portions 90 may follow a tortuous path 92, due to disturbances or collisions with the inner wall of the aspiration lumen 18 while being pulled through the aspiration lumen 18. In some cases, the pieces or portions 90 may catch and slip within the inner wall of the aspiration lumen 18, for example, do to variance of the inner diameter of the aspiration lumen 18 along the length. Either of these situations can cause a corresponding series of increases and decreases in the pressure being sensed by the pressure transducer 12, while the pieces or portions 90 are traveling through the aspiration lumen 18. As graphed in the curve 79 of FIG. 5D, a downward slope 99 and a subsequent steady pressure curve 97 are measured, but as the pieces or portions 90 of thrombus 88 travel down the aspiration lumen 18 of the aspiration catheter 4, a deviation 77 of fluid pressure comprising a one or more decreases and increases in pressure (increases and decreases in vacuum pressure) is measured. As the pieces or portions 90 of thrombus 88 exit the proximal end of the aspiration lumen 18 of the aspiration catheter 4, a second steady pressure curve 75 is measured. The duration 67 of the deviation 77 is the amount of transit of the particular significant pieces or portions 90 of thrombus 88. The duration 67 can range quite a bit, but in some cases may be less than a second or up to about 30 seconds. A single thrombus being aspirated may cause a single decrease in pressure (a blip) which is identified by the measurement device 54, 64. Subsequently, this occurrence may be communicated to the user by the communication device 58a-c, 74. When again additional pieces or portions 90 of thrombus 88 are aspirated into and travel down the aspiration lumen 18 of the aspiration catheter 4, another deviation 73 of fluid pressure comprising a one or more decreases and increases in pressure (increases and decreases in vacuum pressure) is measured. At the end of the curve 79, the vacuum source 6 is shown filling completely with blood 96 and the pieces or portions 90 of thrombus 88, and so an upward slope 95 is measured.

The measurement device 54, 64 is configured to compare the curve 79 with information stored in the memory module 56, 66 to identify when the pieces or portions 90 of thrombus 88 are actively being aspirated, as in deviation 77 and deviation 73, and when the pieces or portions of thrombus 88 are not being actively, or substantially, aspirated, as in steady pressure curve 97, the steady pressure curve 75, and the steady pressure curve 71. In some embodiments, the measurement device 54, 64 uses an algorithm to make the comparison. In some embodiments, a pre-set pressure differential $\Delta P_2$ may be stored in the memory module 56, 66 as a threshold, whereby the measurement of a pressure difference 69 less than this threshold does not result in the measurement device 54, 64 commanding the communication device 58a-c, 74 to send a first type of alert via an alert signal 60a-c, 70. In some embodiments, when the pressure difference 69 is greater than (or greater than or equal to) the pre-set pressure differential $\Delta P_2$, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. In some embodiments, the communication device 58a may comprise a light whose intensity increases proportionally with the pressure. Communication device 58b may create a characteristic sound, or may generate an audio message in a number of languages. For example, the audio message may state, "Thrombus being aspirated." In some embodiments, communication device 58b may comprise one or more noises or beeps. In some embodiments, the communication device 58b may comprise a particular series of beeps corresponding to each different condition. For example, three short beeps may correspond to no thrombus being aspirated, while five long, loud beeps may correspond to a system leak. In some embodiments, a plurality of different tones (pitches) may be used to alert a user about different conditions. As an example, a low pitch sound may be used for a first condition (e.g. no thrombus being aspirated) and a second, higher pitch sound may be used for a second condition (e.g. a system leak). In some embodiments, a plurality of different tones may be used to alert a user about a first condition and a second plurality (e.g. in a different combination, or with additional tones) may be used to alert a user about a second condition. Communication device 58c may vibrate or heat in a characteristic pattern, for example, a certain number of repetitions or a certain frequency between repetitions. When the user realizes that the thrombus is being aspirated, the user may choose to advance (or retract) the aspiration catheter 4, for example with fluoroscopic visualization, along the length of the thrombus 88, in an attempt to continue the aspiration of the thrombus 88. In some cases, the user may choose to stop the advancement or retraction of the aspiration catheter 4 at a certain amount of time after the alert is generated, in order to allow the pieces or portions 90 of thrombus 88 to completely exit the aspiration lumen 18. When the measurement device 54, 64 identifies a subsequent steady pressure curve 75, 71 that follows a deviation 77, 73, the measurement device 54, 64 in some embodiments sends a signal that causes the communication device 58a-c, 74 to generate a second type of alert via an alert signal 60a-c, 70. For example, in some embodiments, communication device 58b may send an audio message that states, "Thrombus no longer being aspirated." When the user realizes that the thrombus is no longer being aspirated, the user may advance or retract the aspiration catheter, in an attempt to contact another portion of the thrombus 88 that can be aspirated. In some embodiments, the deviation 77 may be positively identified as a true deviation indicating thrombus being actively aspirated, pressure difference 69 is between about 700 pascal and about 1700 pascal. In some embodiments, the deviation 77 may be positively identified as a true deviation indicating thrombus being actively aspirated, pressure difference 69 is between about 1000 pascal and about 1300 pascal. In some embodiments, the deviation 77 may be positively identified as a true deviation indicating thrombus being actively aspirated, pressure difference 69 is about 1138 pascal. The pressure difference 69 may be measured by determining a baseline pressure 63 and a peak pressure 61 and determining the absolute value difference. For example:

Absolute value difference (AVD)=|(−89,631 pascal)−(−90,769 pascal)|=1138 pascal

Or for example:

Absolute value difference (AVD)=|(−43,710 pascal)−(−45,102 pascal)|=1281 pascal

The pressure difference 81 (FIG. 5B) may also represent a deviation that may be identified in a similar manner, after which the communication device 58a-c, 74 generates an appropriate alert, such as, "Clog condition."

Figure 5D:
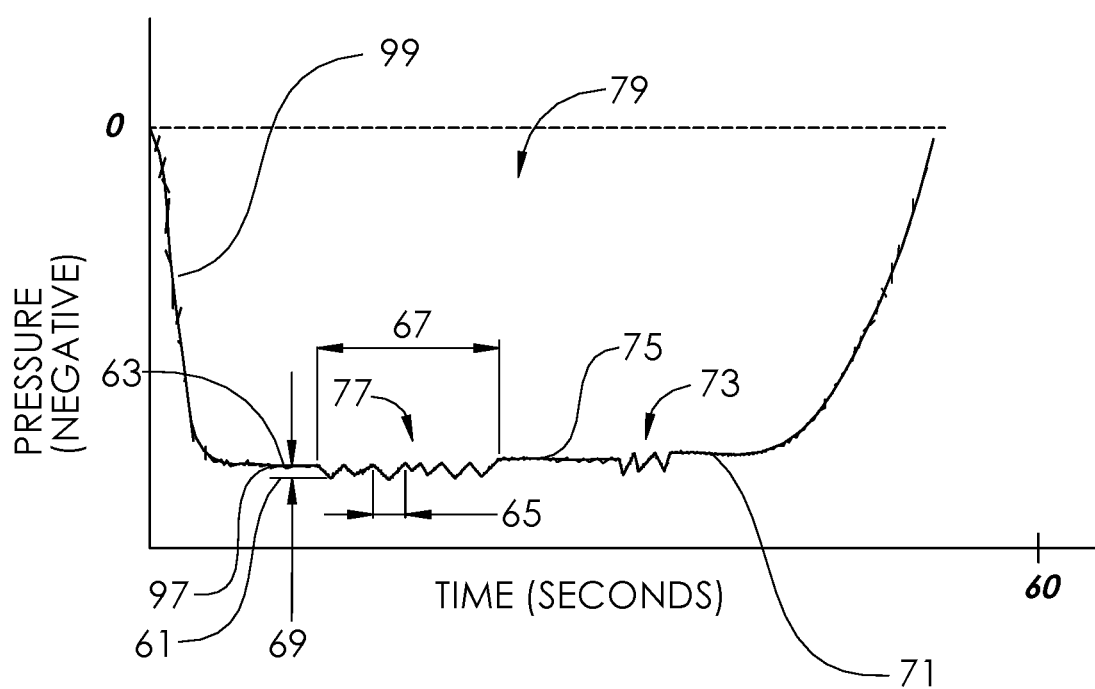
FIG. 5D is a graphic representation of pressure vs. time for the condition of FIG. 4D.

Because vacuum pressure is a negative pressure, the peak pressure 61, as shown in FIG. 5D, is actually a lower number than the baseline pressure 63. In some embodiments, the measurement device 54, 64 may also be configured to make a comparison, for example by using an algorithm, between a stored differential time ti and a duration 65 of a single one of the more or more decreases and increases in pressure in the deviation 77. For example, in some embodiments, the deviation may be positively identified as a true deviation indicating thrombus being actively aspirated, if the duration is between about 0.001 seconds and about 0.50 seconds. In some embodiments, the deviation may be positively identified as a true deviation indicating thrombus being actively aspirated, if the duration is between about 0.005 seconds and about 0.10 seconds. In some embodiments, the deviation may be positively identified as a true deviation indicating thrombus being actively aspirated if the duration is between about 0.05 seconds and about 0.20 seconds. In some embodiments, the measurement device 54, 64 is configured to recognize deviation 77 after two or more decreases and increases in pressure are measured. In some embodiments, the measurement device 54, 64 is configured to recognize deviation 77 after five or more decreases and increases in pressure are measured. In some embodiments, the measurement device 54, 64 is configured to recognize deviation 77 after ten or more decreases and increases in pressure are measured.

The baseline pressure 63 may in some embodiments be predetermined and may be stored in the memory module 56, 66. In some embodiments, the baseline pressure 63 may be stored in in the memory module 56, 66 during the manufacture of the aspiration monitoring system 48, 62, 78, but the baseline pressure 63 may also be input by the user prior to or during a particular procedure. In some embodiments, the baseline pressure 63 may be determined or otherwise defined by the measurement device 54, 64, 76 based on averaging of a particular number of samples of measured pressure. The baseline pressure 63 may be constructed as a moving average, such as a running average or rolling average. Several types of moving average may be used, including a simple moving average, a cumulative moving average, a weighted moving average, or an exponential moving average. In any of these cases, a threshold may be determined by the measurement device 54, 64, 76 based on the determined baseline pressure 63 and a known pressure differential $\Delta P$. In some case, a pressure differential $\Delta P$ may even be calculated by the measurement device 54, 64, 76 based on the determined baseline pressure 63 and a known threshold.

Insertion of the pressure transducer 12 in line in either the embodiment of FIG. 2A or the embodiment of FIG. 2B does not measurably change performance characteristics of the aspiration system 2, because the cavity 42 is relatively short and has a relatively large inner diameter, and thus is not a significant source of fluid flow resistance. In some embodiments, the inner diameter may be between about 2.2 mm (0.086 inches) and about 3.2 mm (0.125 inches). In some embodiments, the measurement device 54, 64, 76 need not include a microprocessor, as pre-defined set points (e.g. for certain thresholds) may be included in firmware, microcontroller, or other locations. In some embodiments, including but not limited to the embodiment of FIG. 2B, the pressure transducer 12 may be an off-the-shelf blood pressure monitor system, which is modified or augmented with other components. In some embodiments an off-the-shelf blood pressure monitor system may be used as the output of the aspiration monitoring system 48, 62, 78. In some embodiments, an aspiration catheter 4 may have a pressure transducer in the distal end 16. This pressure transducer may be used as the pressure transducer 12 of the aspiration monitoring system 48, 62, 78. In some embodiments, a pressure sensor may be located within a Tuohy-Borst valve, and introducer sheath, a guiding catheter, or another component of the system through which is in fluid communication with the aspiration lumen 18. In some embodiments, the pressure sensor may be located anywhere within the aspiration lumen of the aspiration catheter.

In some embodiments, instead of an LED, the visual alert is provided by a communication device 58a comprising a display which displays visual messages of text in a particular language, for example, "Thrombus encountered," "No thrombus encountered," "Clog condition," "System leak," "Loss of vacuum," "Thrombus being aspirated," or "Thrombus no longer being aspirated." The visual messages may be combined with any of the other alert signals 60a-c, 70 described herein. The aspiration monitoring system 48, 62, 78 described herein give real time awareness to users performing aspiration procedures, such as the removal of thrombus via an aspiration system 2. One skilled in the art will recognize that by knowing the real time condition of the aspiration system 2, the user is able to immediately make changes to the procedure in order to optimize results, increase safety for the patient and/or medical personnel, reduce costs (e.g. number of vacuum sources 6 required), and reduce procedure time (also a cost benefit). Because the user is typically performing multiple tasks during an aspiration procedure, the sensory aid provided by the aspiration monitoring system 48, 62, 78 allows the user to focus on these tasks without having to continually attempt to monitor conditions which are often difficult to visually monitor. The user may also modify and control the aspiration monitoring system 48, 62, 78 via an input 59 (FIG. 2B), which may comprise a data entry module, keyboard, or a series of buttons with a display. The input 59 may in some embodiments comprise an auditory input which accepts voice commands. Alternatively, the user may input information and control the aspiration monitoring system, 48, 62, 78 remotely. Some of the alerts which the user may select or deselect in the aspiration monitoring system 48, 62, 78 include, but are not limited to: whether the aspiration system 2 is potentially blocked or clogged, or is flowing normally; whether thrombus has been contacted or not; whether a clog has occurred; whether the vacuum source 6 is adequate, or whether it has been depleted and requires replacement; whether there is a leak in the aspiration system 2; whether setup or connection of the components of the aspiration system 2 was done correctly or incorrectly; whether to advance the catheter distally; whether to retract the catheter; whether to continue moving the catheter at the same speed; whether to increase or decrease the speed of catheter advancement; whether thrombus is actively being aspirated; and whether thrombus stops being actively aspirated. As the user becomes familiar with the aspiration monitoring system 48, 62, 78, the user may even begin to make certain responses to the system subconsciously. For example, a user may automatically pull back the catheter upon hearing a clot warning signal (e.g., three beeps), and may automatically begin advancing the catheter and/or start fluoroscopic visualization upon hearing a free blood flow signal (e.g., two beeps). By being "at one" with the aspiration monitoring system 48, 62, 78 and the catheter, the user optimizes reactions and actions. This may be helpful improving the skill of having the catheter take a small "bite" of thrombus, and following the "bite" with a "chaser" of some fast flowing blood, the clean/open the lumen. This would also help minimize the chance of clogging, and would in turn reduce maintenance or corrections of the system (removing the catheter, flushing the lumen outside of the patient, replacing the catheter). The overall experience for the user is improved, as the user receives instant gratification for good results, and is instantly notified of errors or instances for concern.

In some embodiments, alternate power sources may be used, for example, standard AC power with or without an AC/DC convertor; direct connection to existing equipment (e.g. vacuum pumps, etc.); solar power. The aspiration monitoring system 48, 62, 78 may be packaged sterile or may be resterilizable by techniques known by those skilled in the art. In some embodiments, flow or volume gauges may be used in conjunction with or instead of the pressure gauge 12, in order to determine, for example, a clog, or a change in the amount of vacuum. In some embodiments, the input 59, power module 72, measurement device 64, memory module 66, and communication device 68 (e.g., of FIG. 2B) may all be incorporated into a single external device, which may in some cases be sold separately. In some embodiments, the external device may also have other functions, such as providing aspiration and/or injection (negative pressure and/or positive pressure) to a catheter. In other embodiments, the external device may comprise some, but not all of the input 59, power module 72, measurement device 64, memory module 66, and communication device 68. For example, in some embodiments, a communication device 58 (FIG. 2A) may replace the external communication device 68, and may be carried on the aspiration monitoring system 48, while the input 59, power module 72, measurement device 64, memory module 66 (FIG. 2B) are incorporated into a single external device. A number of combinations are possible, as described in more detail herein.

Though aspiration of thrombus has been described in detail, the aspiration monitoring system 48, 62, 78 has utility in any aspiration application wherein heterogeneous media is being aspirated. This may include the aspiration of emboli (including not thrombotic emboli) from ducts, vessels, or cavities of the body, or even from solid or semi-solid portions of the body, including, but not limited to, portions of fat, breasts, and cancerous tissue.

In some embodiments, the aspiration system 2 is be provided to the user as a kit with all or several of the components described, while in other embodiments, only the aspiration monitoring system 48 is provided. Though discussion herein includes embodiments for aspiration of thrombus and blood, the definition of the word "fluid" should be understood throughout to comprise liquids and gases.

In some embodiments, an additional or alternate sensor may be used to monitor flow conditions for the notification of the user, including, but not limited to: a Doppler sensor, an infrared sensor, or a laser flow detection device. In some embodiments, an externally-attached Doppler sensor may be employed. In some embodiments, an infrared sensor or a laser flow detection device may be employed around the extension tubing 10.

Additional embodiments allow real time communication of the particular value of fluid pressure (for example the level of vacuum) measured by the sensor 50. For example, as the amount of vacuum increases, an audible sound may increase in sound intensity or in sound pressure level (dB) proportionally. Or, as the amount of vacuum increases, the pitch (frequency) of an audible sound may made to rise, and as the amount of vacuum decreases, the pitch may be made to fall (as does a siren). By controlling either the amplitude of a signal or the frequency of a signal by making them proportional to the fluid pressure, the system can give a user a real-time sense of whether the vacuum is increasing, decreasing, or staying the same, as well as whether the pressure is close to zero or quite different from zero. When an audible sound is used as the signal, the user's eyes can remain focused on the procedure, whether by viewing a monitor of fluoroscopic images, the patient, or a separate piece of equipment.

Figure 6:
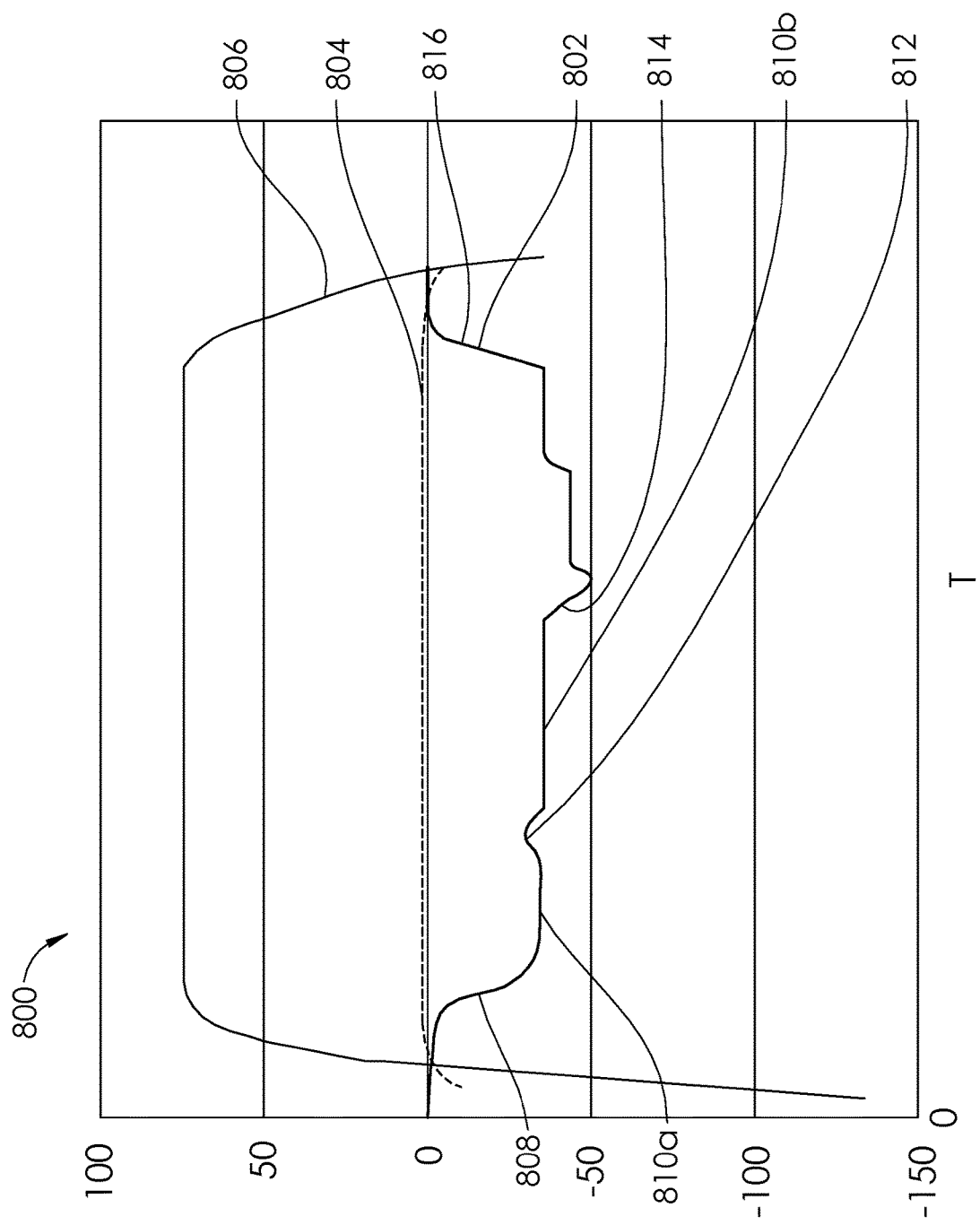
FIG. 6 is a graphic representation of pressure and an output sound amplitude vs. time for an embodiment of an aspiration monitoring system.

FIG. 6 illustrates a graph 800 of time (x-axis) and multiple variables (y-axis). A pressure curve 802 shows a vacuum being applied at a pressure drop 808, and a maintenance of vacuum 810a with a decrease in vacuum 812 and an increase in vacuum 814. A removal of vacuum 816 is shown at the end of the pressure curve 802. In some cases, the decrease in vacuum 812 may be caused by a temporary or permanent leak or detachment within the system or by filling of the vacuum source (e.g., syringe). In FIG. 6, the decrease in vacuum 812 is shown as temporary, as a subsequent maintenance of vacuum 810b is illustrated. The increase in vacuum 814 may in some cases be caused by thrombus being sucked through the system and may occur for a short or long amount of time, and may be steady or intermittent. Though the amount of vacuum applied in the pressure curve 802 varies, in some embodiments, it may only be desirable to show to a user only whether the vacuum is generally being applied or not being applied. The measurement device 54, 64, 76 may be configured to apply an algorithm to the signal from the vacuum sensor 50 (pressure sensor) that calculates an inverse value, represented by the dashed curve 804. The measurement device 54, 64, 76 further may apply an algorithm that increases, amplifies or otherwise augments the signal for ease of identification, for example within the human range of audible identification (hearing). For example, a modified signal curve 806 may be created that has the following general mathematical relationship with the signal from the vacuum sensor 50 represented by the pressure curve 802.

$$\text{Sound Pressure Level (dB)} = A + B \times (1/\text{fluid pressure})$$

where A is a first constant, and
B is a second constant

In one particular example, a modified signal curve 806 may be created that has the following mathematical relationship with the signal from the vacuum sensor 50 represented by the pressure curve 802.

$$\text{Sound Pressure Level (dB)} = 70 + 20 \times (1/\text{fluid pressure (kPa)})$$

where dB is units in decibels, and
kPa is units of kiloPascal

The modified signal curve 806 may be constructed of an algorithm such that the sound pressure level drops below the audible level of human hearing at relatively small amounts of vacuum, thus giving the user an "on/off" awareness of the vacuum being applied.

Figure 7:
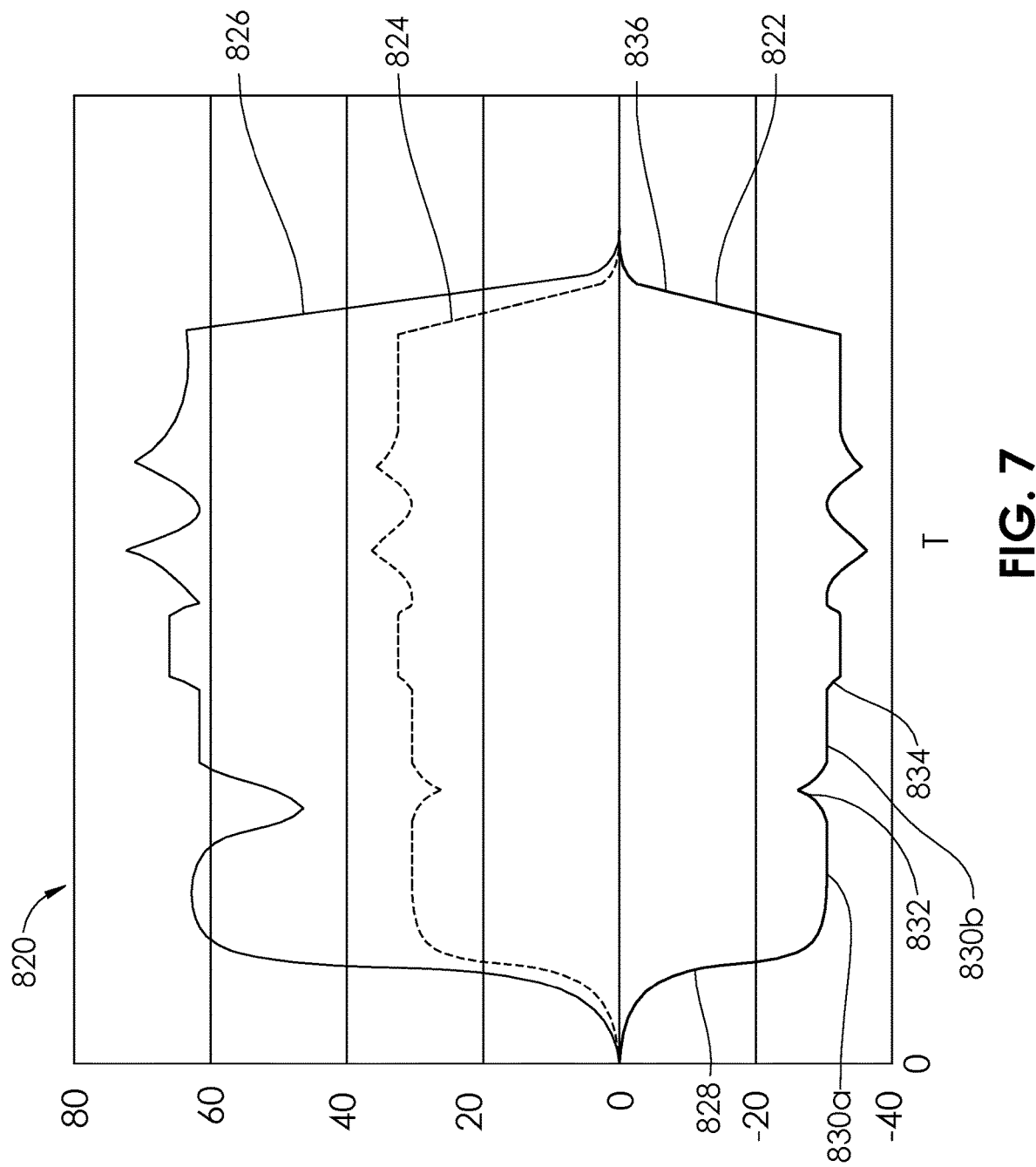
FIG. 7 is a graphic representation of pressure and an output sound amplitude vs. time for an embodiment of an aspiration monitoring system.

FIG. 7 illustrates a graph 820 of time (x-axis) and multiple variables (y-axis). A pressure curve 822 shows a vacuum being applied at a pressure drop 828, and a maintenance of vacuum 830a with a decrease in vacuum 832 and an increase in vacuum 834. A removal of vacuum 836 is shown at the end of the pressure curve 822. In some cases, the decrease in vacuum 832 may be caused by a temporary or permanent leak or detachment within the system or by filling of the vacuum source (e.g., syringe). In FIG. 7, the decrease in vacuum 832 is shown as temporary, as a subsequent maintenance of vacuum 830b is illustrated. The increase in vacuum 834 may in some cases be caused by thrombus being sucked through the system and may occur for a short or long amount of time, and may be steady or intermittent. In some cases or configurations, it may be desirable for the user to have a very specific real-time or close to real-time characterization of the amount or level of vacuum (or pressure in general) being applied. The measurement device 54, 64, 76 may be configured to apply an algorithm to the signal from the vacuum sensor 50 (pressure sensor) that calculates an absolute value, represented by the dashed curve 824. The measurement device 54, 64, 76 further may apply an algorithm that increases, amplifies or otherwise augments the signal for ease of identification, for example within the human range of audible identification (hearing). For example, a modified signal curve 826 may be created that has the following general mathematical relationship with the signal from the vacuum sensor 50 represented by the pressure curve 822.

$$\text{Sound Pressure Level (dB)} = A + B \times |(\text{fluid pressure})|$$

where A is a first constant, and
B is a second constant

In one particular example, a modified signal curve 826 may be created that has the following mathematical relationship with the signal from the vacuum sensor 50 represented by the pressure curve 822.

$$\text{Sound Pressure Level (dB)} = 2 \times |(\text{fluid pressure (kPa)})|$$

where dB is units in decibels and,
kPa is units of kiloPascal

The modified signal curve 826 may be constructed of an algorithm such that the sound pressure level seems to the user to follow the amount of vacuum being applied, thus becoming louder as the vacuum is increased.

Figure 8:
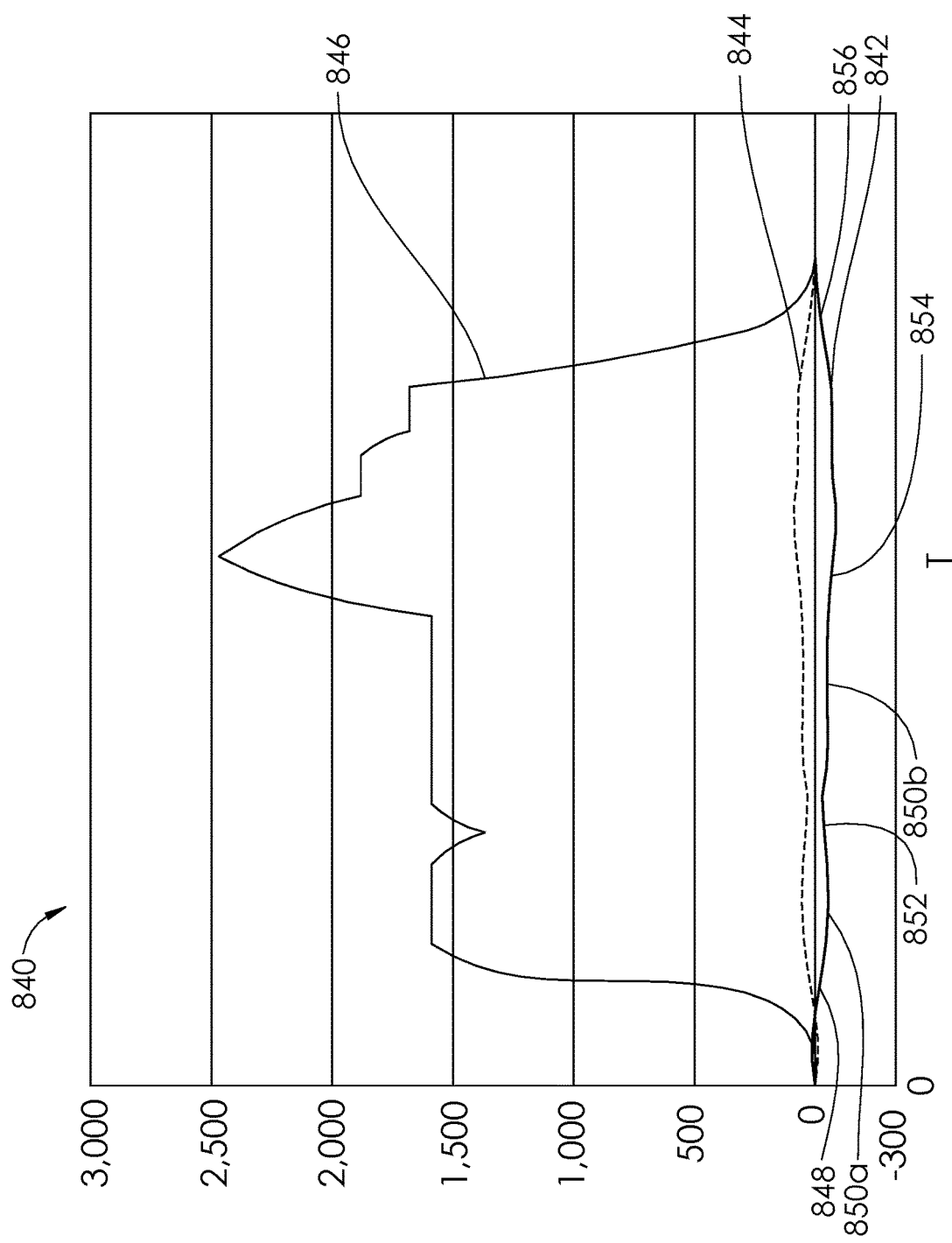
FIG. 8 is a graphic representation of pressure and an output sound frequency vs. time for an embodiment of an aspiration monitoring system.

FIG. 8 illustrates a graph 840 of time (x-axis) and multiple variables (y-axis).

A pressure curve 842 shows a vacuum being applied at a pressure drop 848, and a maintenance of vacuum 850a with a decrease in vacuum 852 and an increase in vacuum 854. A removal of vacuum 856 is shown at the end of the pressure curve 842. In some cases, the decrease in vacuum 852 may be caused by a temporary or permanent leak or detachment within the system or by filling of the vacuum source (e.g., syringe). In FIG. 8, the decrease in vacuum 852 is shown as temporary, as a subsequent maintenance of vacuum 850b is illustrated. The increase in vacuum 854 may in some cases be caused by thrombus being sucked through the system and may occur for a short or long amount of time, and may be steady or intermittent. As mentioned, in some cases or configurations, it may be desirable for the user to have a very specific real-time or close to real-time characterization of the amount or level of vacuum (or pressure in general) being applied. The measurement device 54, 64, 76 may be configured to apply an algorithm to the signal from the vacuum sensor 50 (pressure sensor) that calculates an absolute value, represented by the dashed curve 844. The measurement device 54, 64, 76 further may apply an algorithm that determines a frequency of an audible sound (or pitch), for example within the human range of audible identification (hearing), that varies within the human range of audible frequencies. For example, a modified signal curve 846 may be created that has the following general mathematical relationship with the signal from the vacuum sensor 50 represented by the pressure curve 842.

$$\text{Sound Frequency (Hz)} = A + B \times |(\text{pressure})|$$

where A is a first constant, and
B is a second constant

In one particular example, a modified signal curve 846 may be created that has the following mathematical relationship with the signal from the vacuum sensor 50 represented by the pressure curve 842.

$$\text{Sound Frequency (Hz)} = 50 \times |(\text{fluid pressure (kPa)})|$$

where Hz is Hertz (1/second), and
kPa is units of kiloPascal

The modified signal curve 846 may be constructed of an algorithm such that the sound frequency seems to the user to follow the amount of vacuum being applied. In this embodiment, the pitch of the sound becomes "higher" when vacuum is increased (fluid pressure decreases), and "lower" when the vacuum is decreased. Alternatively, the opposite may instead by chosen, wherein the pitch of the sound becomes lower when vacuum is increased.

Figure 9:
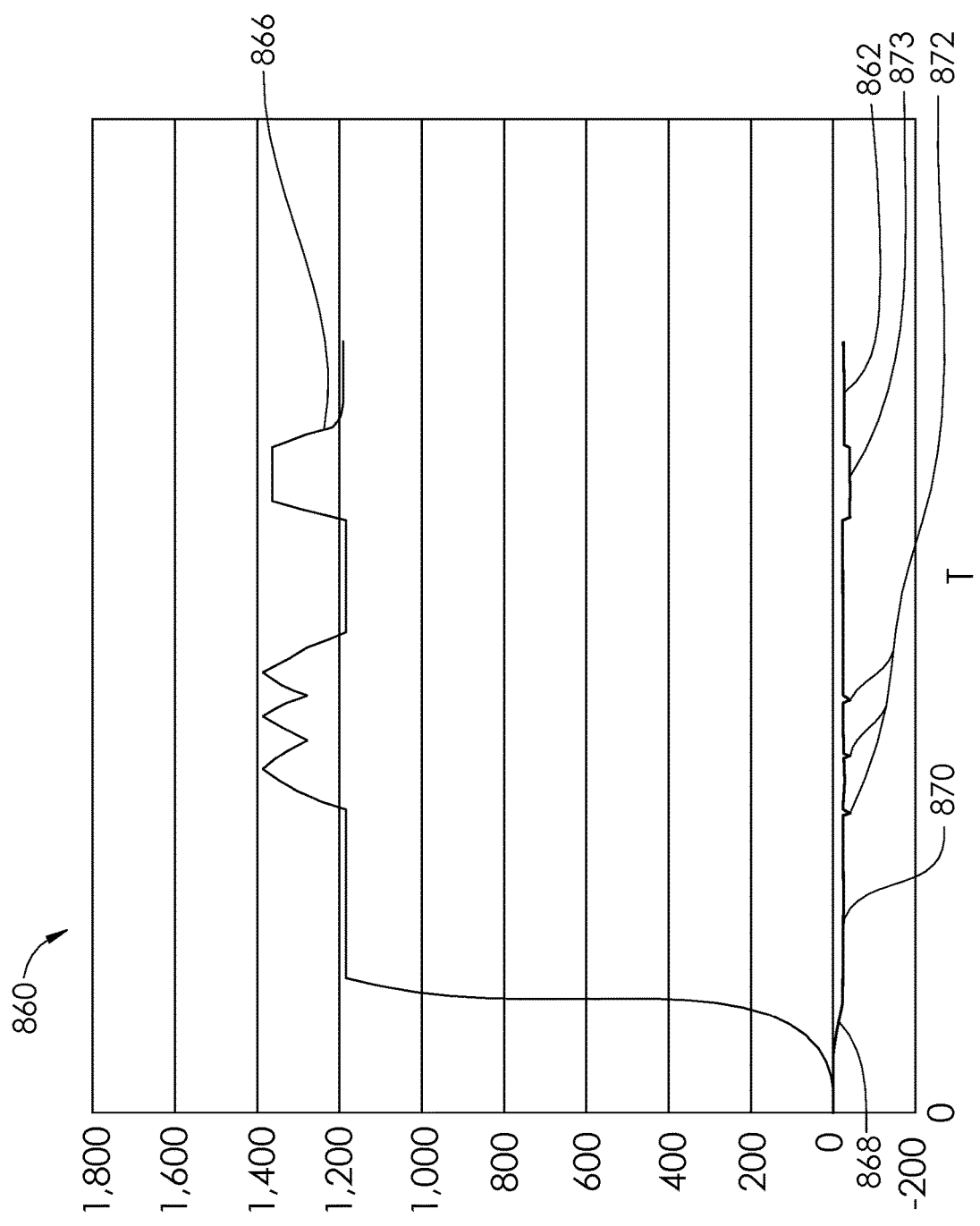
FIG. 9 is a graphic representation of pressure and an output of sound frequency vs. time for an embodiment of an aspiration monitoring system.

FIG. 9 illustrates a graph 860 of time (x-axis) and multiple variables (y-axis). A pressure curve 862 shows a vacuum being applied at a pressure drop 868, and a maintenance of vacuum 870 with a one or more decreases and increases in pressure 872. These one or more decreases and increases in pressure 872 (or increases and decreases in vacuum) may represent, in some instances, clot being sucked through aspiration lumen of an aspiration catheter. In some cases, a single decrease in pressure 873 (increase in vacuum) may occur. The single decrease in pressure 873 may in some cases be extended in duration, as shown in FIG. 9, as may any one of the one or more decreases and increases in pressure 872. In some cases or configurations, it may be desirable for the user to have a very specific real-time or close to real-time characterization of the instances when these small perturbations are occurring, as they may correspond to the catheter finding and aspirating a portion of thrombus. The measurement device 54, 64, 76 be configured to apply an algorithm that determines a frequency of an audible sound (or pitch), for example within the human range of audible identification (hearing), that varies within the human range of audible frequencies. For example, a modified signal curve 866 may be created that has the following general mathematical relationship with the signal from the vacuum sensor 50 represented by the pressure curve 862.

$$\text{Sound Frequency (Hz)} = A + B \times (\text{fluid pressure})$$

where A is a first constant, and
B is a second constant

In one particular example, a modified signal curve 866 may be created that has the following mathematical relationship with the signal from the vacuum sensor 50 represented by the pressure curve 862.

$$\text{Sound Frequency (Hz)} = 40 \times (\text{fluid pressure (kPa)})$$

where Hz is Hertz (1/second), and
kPa is units of kiloPascal

It should be noted that in this equation, no absolute value is used, but rather the actual value of fluid pressure. Or in some cases, an absolute (or negative) value may be used.

The modified signal curve 866 may be constructed of an algorithm such that the sound maintains a steady pitch until the clot is being sucked through the catheter, at which time the pitch changes slightly, but distinctly, away from a steady pitch. For example, in some embodiments, the pitch may change between about 20 Hz and about 2000 Hz to correspond to a pressure change of between about one kPa to about two kPa, or between about 40 Hz and about 80 Hz.

In any of the examples, the modification of signals may include any type of signal conditioning or signal modification that may be performed, including, but not limited to filtering, amplification, or isolation. The modified signal curve 806, 826, 846, 866 is used to determine the output signal to be generated by the communication device 58, 68, 74. As mentioned, if the output signal of the communication device 58, 68, 74 is configured to be an audible sound, the sound pressure level may be varied, or the sound frequency may be varied. In some embodiments, the output signal of the communication device 58, 68, 74 may have both its sound pressure level and sound frequency varied. In one embodiment, the sound frequency varies continuously in proportion to fluid pressure, but at one or more particular thresholds of fluid pressure, the sound pressure level may be caused to vary quite suddenly and strikingly. Thus there is a two-part communication occurring, a continuous real-time status indicator, with an intermittent, alert indicator (failure, danger, etc.). In some cases, the continuous real-time status indicator may represent a first continuous signal and the alert indicator may represent a second alert signal. In other cases, the continuous real-time status indicator and the alert indicator may be combined or integrated into the same signal. In some embodiments, other characteristics of psychoacoustics may be varied using variable sound generation devices. In some embodiments, the spectral envelope may be varied. In some embodiments, timbre may be changed to varies levels between light and dark, warm and harsh, or different noise "colors" (pink, white, blue, black, etc.).

Though an audible output from the communication device 58, 68, 74 has been described with the examples from FIGS. 6-9, other communication signals may be used, including visual or tactile signals. Tactile signals may also include vibration devices or heat generation devices, either of which could be varied (as described) in relation to the measured fluid pressure. Either the amplitude of the frequency could analogously be varied in communication signals that include signals other than the audible signals already described. For example, the intensity of a light can be varied, or the frequency (e.g., color) of a light can be varied. The amplitude of displacement of a vibration device can be varied (or other techniques that vary the vibration intensity) or the frequency of the vibration can be varied.

In some cases, a pseudo-continuous analog may be used in place of a truly variable output. For example, instead of a single light whose intensity is continuously varied, an array of multiple lights, for example and array comprising multiple LEDs, may be used, with an increased number of LEDs being lit when the level of vacuum is increased, and a decreased number of LEDs being lit when the level of vacuum is decreased. The same may be possible with an array comprising multiple vibrating elements, wherein more elements begin vibrating upon an increase or decrease, depending on the application, of fluid pressure.

In any of the embodiments described in relation to FIGS. 6-9, the equations for sound pressure level or for sound frequency which depend on fluid pressure as a variable, may depend on actual measured fluid pressure, or an absolute value of actual measured fluid pressure, but may also use measured fluid pressure in an alternative manner. For example, with a baseline pressure 63 either pre-set, predetermined, or determined or calculated by any other method (averaging, etc.), the differential between the measured pressure and the baseline pressure 63 may be used as the variable on which to base the particular dependency (e.g., proportionality).

Thus, a base mathematical relationship used with the proportionality described with respect to the embodiment of FIG. 6 may be represented as:

$$\text{Sound Pressure Level (dB)} = A + B \times (1/\Delta P)$$

where A is a first constant,
B is a second constant, and
ΔP is a difference or differential between a baseline pressure and a measured fluid pressure.

Likewise, a base mathematical relationship used with the proportionality described with respect to the embodiment of FIG. 7 may be represented as:

$$\text{Sound Pressure Level (dB)} = A + B \times |(\Delta P)|$$

where A is a first constant,
B is a second constant, and
ΔP is a difference or differential between a baseline pressure and a measured fluid pressure.

Likewise, a base mathematical relationship used with the proportionality described with respect to the embodiment of FIG. 8 may be represented as:

$$\text{Sound Frequency (Hz)} = A + B \times |(\Delta P)|$$

where A is a first constant,
B is a second constant, and
ΔP is a difference or differential between a baseline pressure and a measured fluid pressure.

Likewise, a base mathematical relationship used with the proportionality described with respect to the embodiment of FIG. 9 may be represented as:

$$\text{Sound Frequency (Hz)} = A + B \times (\Delta P)$$

where A is a first constant,
B is a second constant, and
ΔP is a difference or differential between a baseline pressure and a measured fluid pressure.

Figure 10:
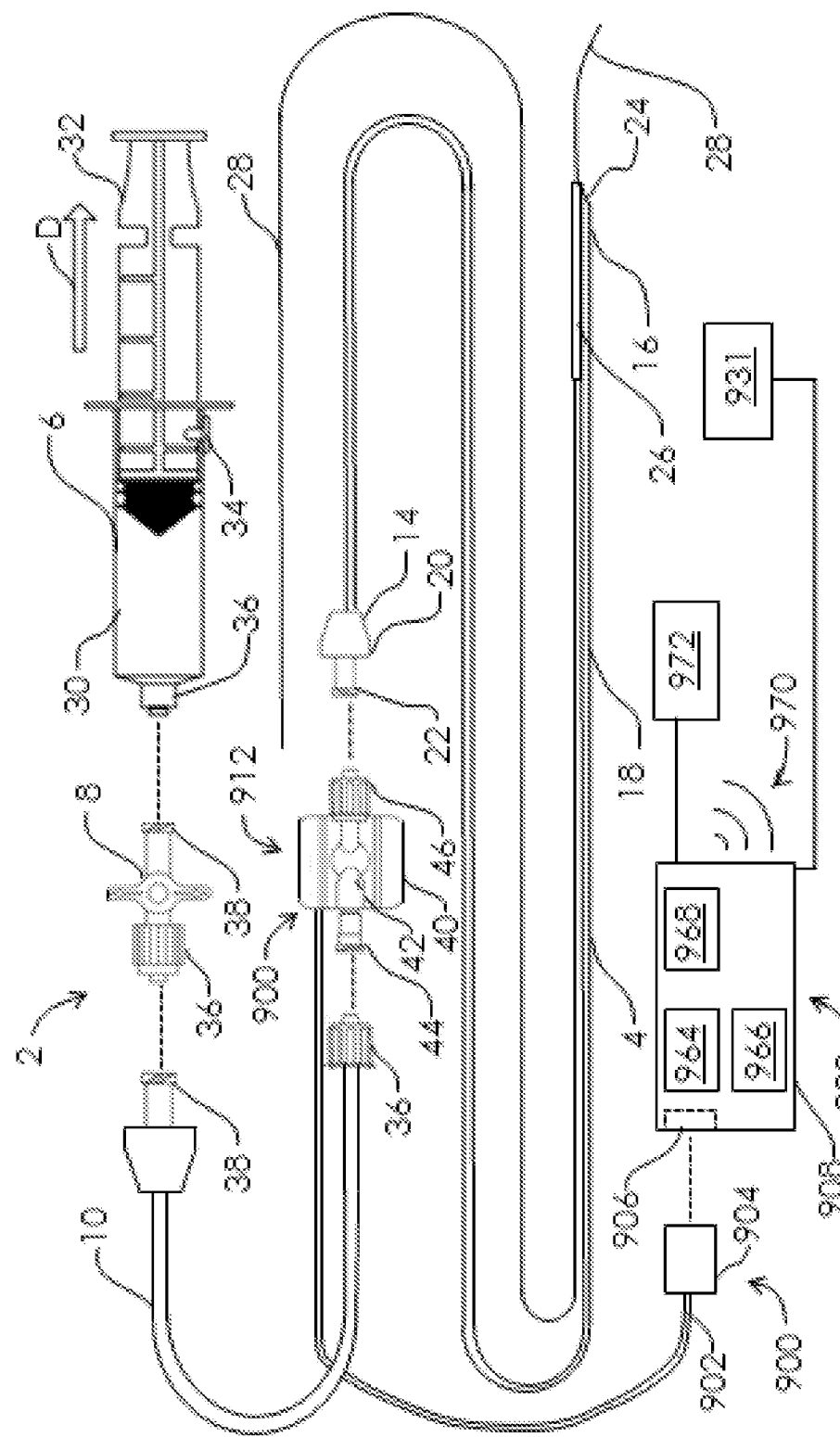
FIG. 10 is a plan view of a system for aspiration according to another embodiment of the present disclosure.

A pressure transducer 912 of an aspiration monitoring system 900 is illustrated in FIG. 10, for coupling to an aspiration system including an aspiration catheter 4. The pressure transducer 912 includes a housing 40, a first port 44, a second port 46 and a cable 902 for carrying a signal. The cable 902 includes an interface 904, or plug, which is configured to connect to a port 906 of a console 908 of the aspiration monitoring system 900. The housing 40 of the pressure transducer 912 includes a cavity 42 extending between the first port 44 and the second port 46. The console 908 is powered by a power module 972, which is connected to the console 908, and may comprise a source of AC or DC power. The console 908 may include a measurement device 964, a memory module 966 and a communication device 968, which may be coupled coupled to each other as described in the prior embodiments and configured such that the communication device 968 is capable of creating a signal 970, which may be an alert signal, a continuous signal, a combined signal, or other type of signal. The console 908 may also include wired or wireless connections to other interfaces or displays which may be found in health care sites, such as a monitor 931. In some embodiments, the monitor 931 may be a monitor which also displays fluoroscopy or angiogram images, or a monitor which also displays electrocardiography or blood pressure graphics or other information. The monitor 931 may have a portion that maintains the status of the aspiration. For example, it may read "Thrombus being aspirated" or "No thrombus detected." The pressure transducer 912 (housing 40, ports 44, 46, cable 902, interface 904) may be sold sterile, and may be configured to output a signal that is received by the console 908, for example the measurement device 964 of the console 908. The pressure transducer 912 may have its own internal source of power (e.g., the battery 52 in FIG. 2A), or may be powered by its connection to the console 908, or alternatively, by its connection to the aspiration catheter 4, or even the extension tubing 10. In some embodiments, the console 908 may be configured to identify and/or recognize the pressure transducer 912, for example, to recognize the particular model of the pressure transducer 912. In some embodiments, the console 908 may be configured to measure a resistance between two electrical contacts in the pressure transducer 912 in order to identify the type (e.g., model) of pressure transducer. In some embodiments, the console 908 may be configured to read an RFID chip on the pressure transducer 912. The console 908 may also be configured to connect to two or more different models of pressure transducer. The port 906, may comprise at least one port, which may comprise two or more ports, each port configured to allow connection of a different model of pressure transducer.

An aspiration system 1000 in FIG. 11 includes an aspiration console 1001 having a connector 1002, or hub, (e.g., male luer) for connecting to an aspiration catheter 4, for example, to a connector 22 (e.g., female luer) of the aspiration catheter 4. The aspiration console 1001 is powered by a power module 972, which is connected to the aspiration console 1001, and may comprise a source of AC or DC power. The aspiration console 1001 may include a canister 1006 for collecting the aspirated materials, and may include a vacuum pump 1004 for creating a vacuum with which to create the aspiration. Tubing 1008 may be connected between the canister 1006 and the connector 1002. In some embodiments, the canister 1006 is removable or replaceable. An aspiration monitoring system 900 includes a pressure sensor 1010 (e.g., a vacuum sensor) in fluid communication with the tubing 1008. The tubing 1008 may instead comprise a lumen formed inside fabricated parts. The aspiration monitoring system 900 is shown in more detail in FIG. 12, and may include some or all of the features described in relation to FIG. 10. The aspiration console 1001 may also include wired or wireless connections to other interfaces or displays which may be found in health care sites, such as a monitor 931. In some embodiments, the monitor 931 may be a monitor which also displays fluoroscopy or angiogram images, or a monitor which also displays electrocardiography or blood pressure graphics or other information. By combining all communication related to the procedure on or at a single monitor or single monitor location, uninterrupted focus can be achieved by the user, who may be freely dedicated to the safe advancement and placement of the aspiration catheter in proximity to the thrombus.

A system for forced (or assisted) aspiration 1100 in FIG. 13 includes an aspiration/injection console 1101 having a first connector 1016, or hub, (e.g., male luer) for connecting to an injection lumen 1020 of a forced aspiration catheter 1013, and a second connector 1012, or hub (e.g., male luer) for connecting to an aspiration lumen 1018 of the forced aspiration catheter 1013. The first connector 1016 is configured to connect to connector 1024 (e.g., female luer) of a y-connector 1022 and the second connector 1012 is configured to connect to connector 1026 of the y-connector 1022 at a proximal end 14 of the forced aspiration catheter 1013. The aspiration/injection console 1101 is powered by a power module 972, which is connected to the aspiration console 1101, and may comprise a source of AC or DC power. The aspiration console 1101 may include a canister 1106 for collecting the aspirated materials, and may include a vacuum pump 1104 for creating a vacuum with which to create the aspiration. Tubing 1108 may be connected between the canister 1106 and the connector 1012. A positive pressure pump 1014 is coupled to a fluid source 1032 (e.g., a saline bag) and is configured to inject infusate out the connector 1016 at a high pressure. An aspiration monitoring system 900 includes a pressure sensor 1110 (e.g., a vacuum sensor) in fluid communication with the tubing 1108. The tubing 1108 may instead comprise a lumen formed inside fabricated parts. The aspiration monitoring system 900 is shown in more detail in FIG. 14, and may include some or all of the features described in relation to FIG. 10. At a distal end 16 of the forced aspiration catheter 1013, the injection lumen 1020 terminates in an orifice 1028, which is configured to create a jet 1030 formed from the high pressure infusate exiting the orifice 1028. The jet 1030 enters the aspiration lumen 1018, thus creating suction at the distal end 16 of the forced aspiration catheter 1013, which forces materials (e.g., thrombus) into the aspiration lumen 1018, and into the canister 1106. The aspiration/injection console 1101 may also include wired or wireless connections to other interfaces or displays which may be found in health care sites, such as a monitor 931. In some embodiments, the monitor 931 may be a monitor which also displays fluoroscopy or angiogram images, or a monitor which also displays electrocardiography or blood pressure graphics or other information.

In an alternative embodiment, the forced aspiration catheter 1013 of the aspiration catheter 4 may have an additional lumen or guide channel for placement of an additional device or tool. In some embodiments, the guidewire lumen 26 may be used as this additional lumen, and may extend the entire length or most of the length of the catheter, so that the lumen is accessible from the proximal end 14. The additional device or tool may comprise a laser fiber, a mechanical screw, a vibrating wire or a variety of other modalities for disrupting thrombus or other material.

In any of the embodiments presented, the system may be configured so that most or all of the components are supplied together. For example, a catheter and an aspiration monitoring system that are permanently attached to each other. In some embodiments, the aspiration catheter and/or the aspiration monitoring system may include configurations that purposely make it difficult to reprocess (e.g., clean or resterilize) them, thus protecting from potential uses that are not recommended or warranted, and which may risk patient infection and/or device malfunction. For example, the sensor or the portion adjacent the sensor may be purposely difficult to access or clean. Alternatively, one or more batteries may be impossible to access or change.

In some embodiments, it may be desired to have other descriptive warnings that can be tied to pressure measurement or pressure measurement combined with another measured attribute. For example, if a sensor (accelerometer or temperature sensor) within the aspiration catheter is used to detect catheter movement, a change in this sensor may be tied to the pressure sensor. In this manner, a catheter that is engaged with a thrombus at its tip and is moved (e.g., begins to be pulled out of the patient) may then cause a warning: "Warning, do not move catheter; risk of thromboembolus."

Figure 15:
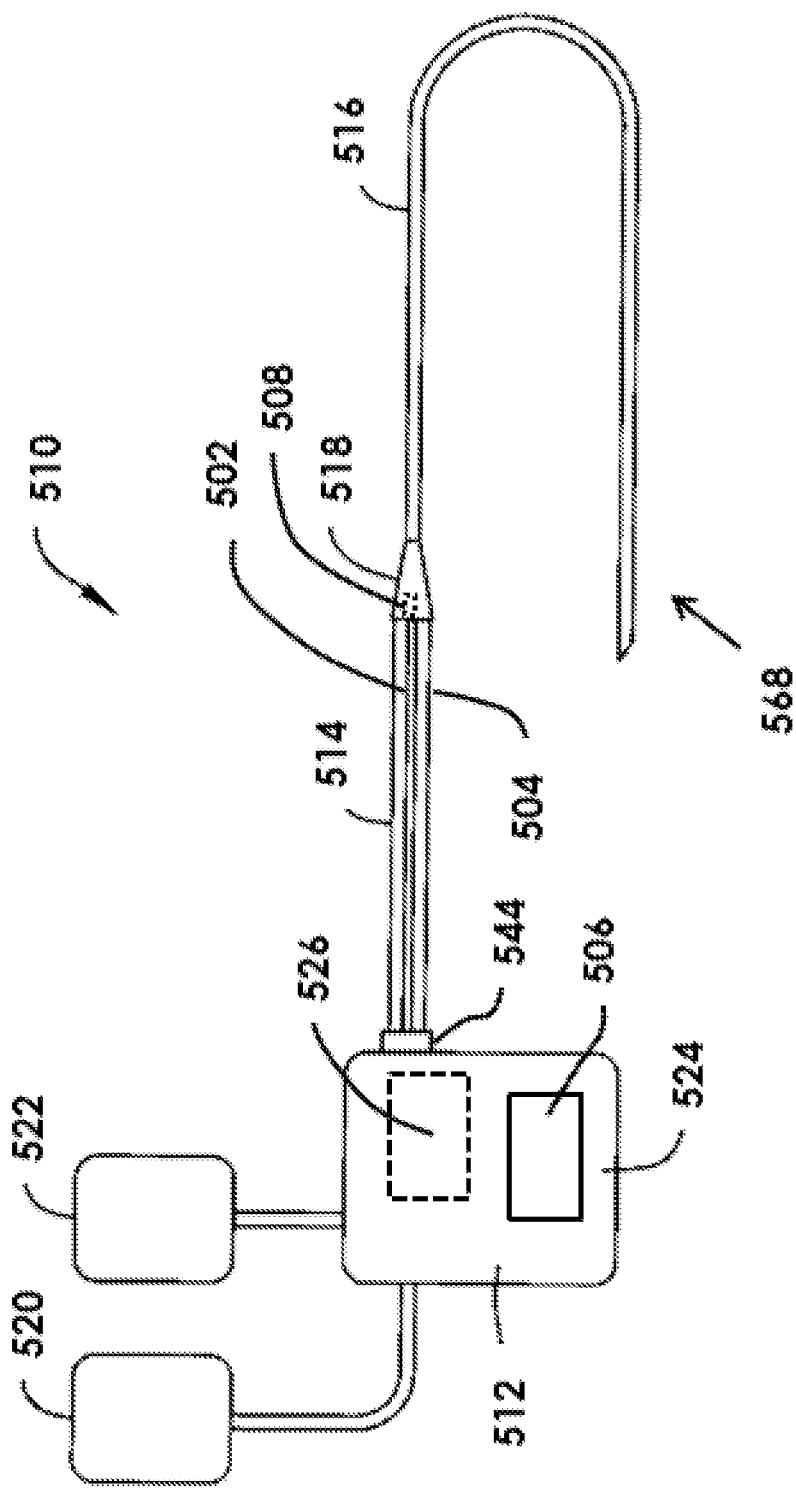
FIG. 15 is a diagrammatic view of a system for aspirating thrombus according to an embodiment of the present disclosure.

FIG. 15 is a diagrammatic figure depicting an assisted aspiration system 510. The aspiration system 510 includes a remote hand piece 512 that contains a fluid pump 526 and an operator control interface 506. In one contemplated embodiment, the system 510 is a single use disposable unit. The aspiration system 510 may also include extension tubing 514, which contains a fluid irrigation lumen 502 and an aspiration lumen 504, and which allows independent manipulation of a catheter 516 without requiring repositioning of the hand piece 512 during a procedure performed with the aspiration system 510. Extension tubing 514 may also act as a pressure accumulator. High pressure fluid flow from the pump 526, which may comprise a displacement pump, pulses with each stroke of the pump 526 creating a sinusoidal pressure map with distinct variations between the peaks and valleys of each sine wave. Extension tubing 514 may be matched to the pump 526 to expand and contract in unison with each pump pulse to reduce the variation in pressure caused by the pump pulses to produce a smooth or smoother fluid flow at tip of catheter 516. Any tubing having suitable compliance characteristics may be used. The extension tubing 514 may be permanently attached to the pump 526 or it may be attached to the pump 526 by a connector 544. The connector 544 is configured to ensure that the extension tubing 514 cannot be attached to the pump 526 incorrectly.

Figure 17:
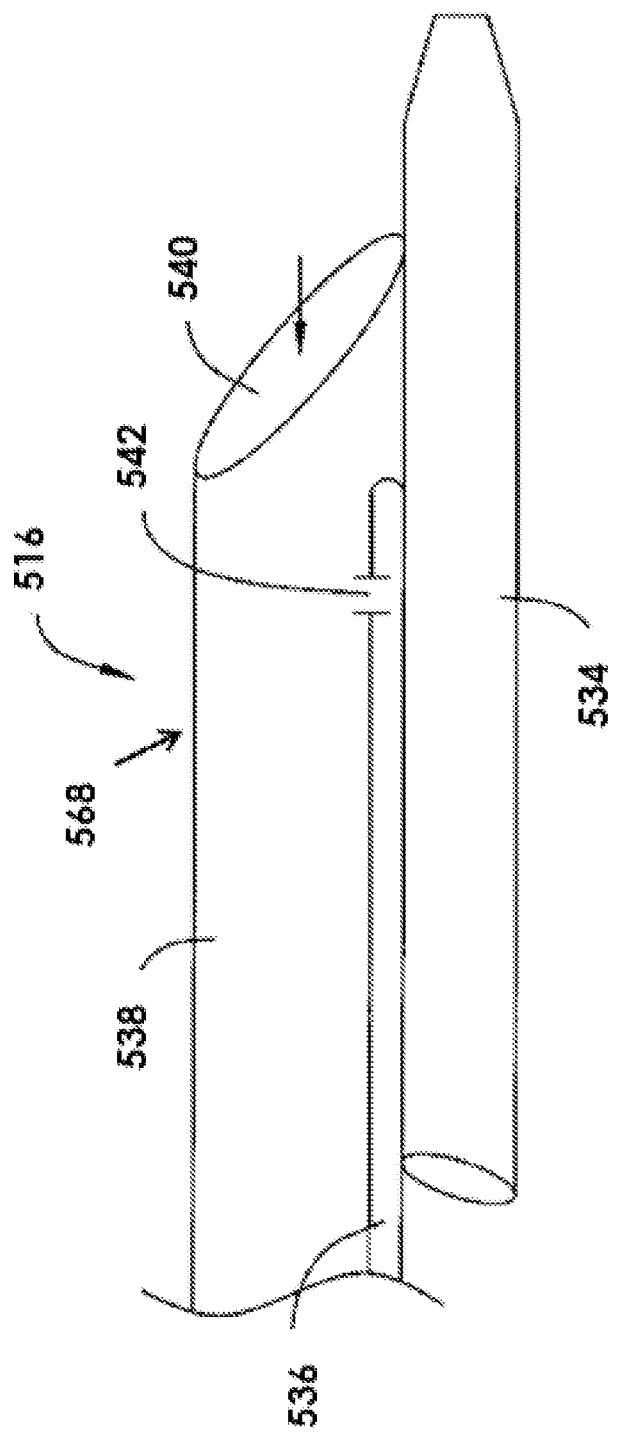
FIG. 17 is a diagrammatic view of the distal end portion of the system for aspirating thrombus of FIG. 15.

An interface connector 518 joins the extension tubing 514 and the catheter 516 together. In one contemplated embodiment, the interface connector 518 may contain a filter assembly 508 between high pressure fluid injection lumen 502 of the extension tubing 514 and a high pressure injection lumen 536 of the catheter 516 (FIG. 17). The catheter 516 and the extension tubing 514 may be permanently joined by the interface connector 518. Alternatively, the interface connector 518 may contain a standardized connection so that a selected catheter 516 may be attached to the extension tubing 514. In some embodiments, the filter assembly 508 may be removably coupled to the extension tubing 514 by a quick disconnect connection. A pressure transducer of an embodiment of the aspiration monitoring system presented herein may be located at a point along the aspiration lumen 504 or any extension of the aspiration lumen 504.

Attached to the hand piece 512 are a fluid source 520 and a vacuum source 522. A standard hospital saline bag may be used as fluid source 520; such bags are readily available to the physician and provide the necessary volume to perform the procedure. Vacuum bottles may provide the vacuum source 522 or the vacuum source 522 may be provided by a syringe, a vacuum pump or other suitable vacuum source. The filter assembly 508 serves to filter particulate from the fluid source 520 to avoid clogging of the high pressure injection lumen 536 and an orifice 542 (FIG. 17). As described herein, distal sections of the high pressure injection lumen 536 may be configured with small inner diameters, and to the filter assembly 508 serves to protect their continuing function. By incorporating one of a variety of catheters 516 into the assisted aspiration system 510, for example with varying lumen configurations (inner diameter, length, etc.), a variety of aspiration qualities (aspiration rate, jet velocity, jet pressure) may be applied in one or more patients. These aspiration qualities can be further achieved by adjustment of the pump 526, to modify pump characteristics (flow rate, pump pressure). In some embodiments, the catheter 516 may be used manually, for example, without the pump 526, and controlled by hand injection. The manual use of the catheter 516 may be appropriate for certain patient conditions, and may serve to reduce the cost of the procedure.

In one contemplated embodiment, the catheter 516 has a variable stiffness ranging from stiffer at the proximal end to more flexible at the distal end. The variation in the stiffness of the catheter 516 may be achieved with a single tube with no radial bonds between two adjacent tubing pieces. For example, the shaft of the catheter 516 may be made from a single length of metal tube that has a spiral cut down the length of the tube to provide shaft flexibility. Variable stiffness may be created by varying the pitch of the spiral cut through different lengths of the metal tube. For example, the pitch of the spiral cut may be greater (where the turns of the spiral cut are closer together) at the distal end of the device to provide greater flexibility. Conversely, the pitch of the spiral cut at the proximal end may be lower (where the turns of the spiral cut are further apart) to provide increased stiffness. A single jacket covers the length of the metal tube to provide for a vacuum tight catheter shaft. Other features of catheter 516 are described with reference to FIG. 17, below.

Figure 16:
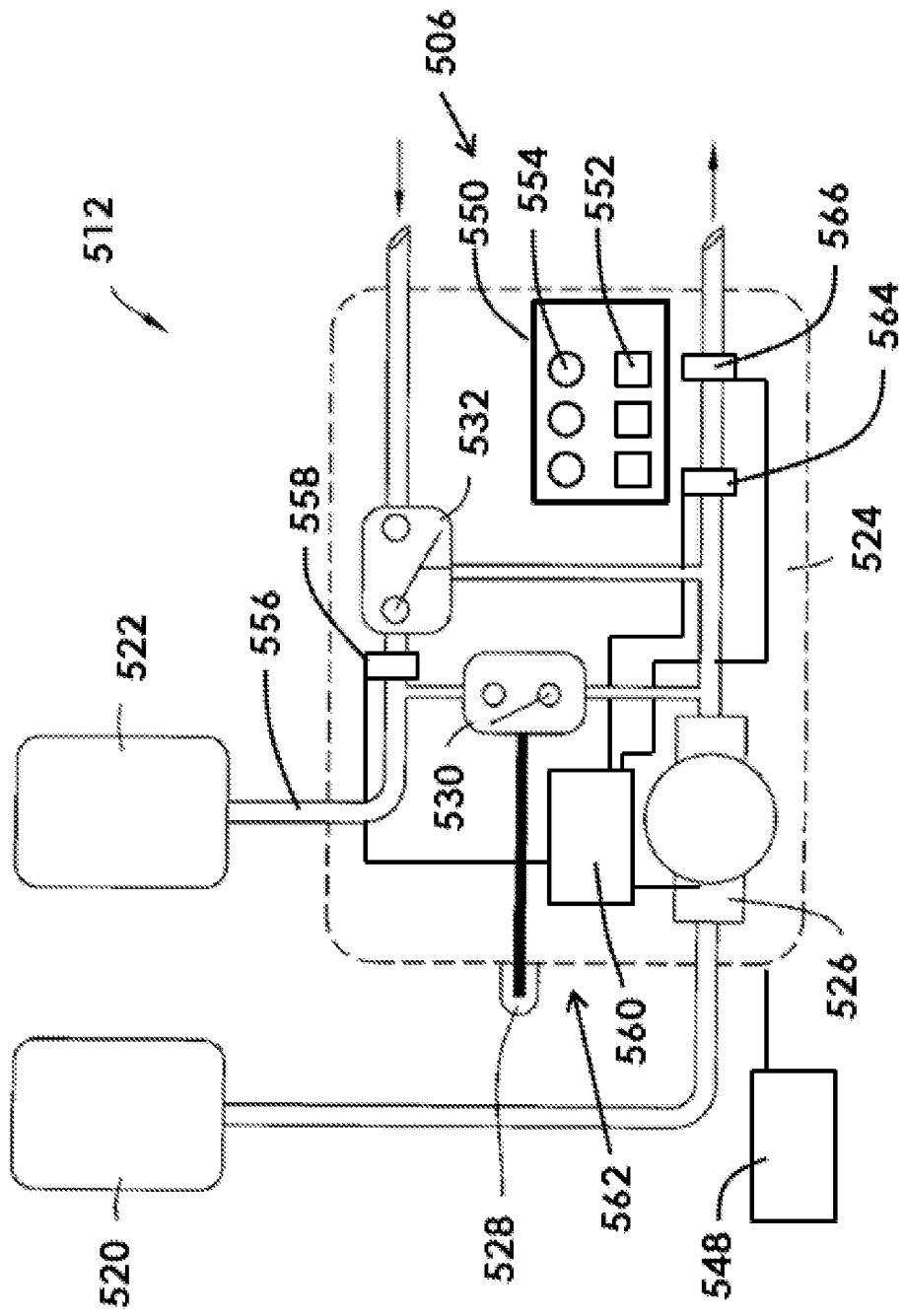
FIG. 16 is a diagrammatic view showing more detail of the proximal portion of the system for aspirating thrombus of FIG. 15.

FIG. 16 is a diagrammatic view showing more detail of the hand piece 512 and the proximal portion of assisted catheter aspiration system 510. The hand piece 512 includes a control box 524 where the power and control systems are disposed. The pump 526 may be a motor driven displacement pump that has a constant output. This pump displacement to catheter volume, along with the location of the orifice 542 (exit) of the catheter high pressure lumen 536 within the aspiration lumen 538 (FIG. 17), ensures that no energy is transferred to the patient from the saline pump as all pressurized fluid is evacuated by the aspiration lumen. A prime button 528 is mechanically connected to a prime valve 530. When preparing the device for use, it is advantageous to evacuate all air from the pressurized fluid system to reduce the possibility of air embolization. By depressing the prime button 528, the user connects the fluid source 520 to the vacuum source 522 via the pump 526. This forcefully pulls fluid (for example 0.9% NaCl solution, or "saline", no "normal saline", or heparinized saline) through the entire pump system, removing all air and positively priming the system for safe operation. A pressure/vacuum valve 532 is used to turn the vacuum on and off synchronously with the fluid pressure system. One contemplated valve 532 is a ported one way valve. Such a valve is advantageous with respect to manual or electronic valve systems because it acts as a tamper proof safety feature by mechanically and automatically combining the operations of the two primary systems. By having pressure/vacuum valve 532, the possibility of turning the vacuum on without activating the fluid system is eliminated.

The operator control interface 506 is powered by a power system 548 (such as a battery or an electrical line), and may comprise an electronic control board 550, which may be operated by a user by use of one or more switches 552 and one or more indicator lamps 554. The control board 550 also monitors and controls several device safety functions, which include over pressure and air bubble detection and vacuum charge. A pressure sensor 564 monitors pressure, and senses the presence of air bubbles. Alternatively, an optical device 566 may be used to sense air bubbles. In one contemplated embodiment, the pump pressure is proportional to the electric current needed to produce that pressure. Consequently, if the electric current required by pump 526 exceeds a preset limit, the control board will disable the pump by cutting power to it. Air bubble detection may also be monitored by monitoring the electrical current required to drive the pump at any particular moment. In order for a displacement pump 526 to reach high fluid pressures, there should be little or no air (which is highly compressible) present in the pump 526 or connecting system (including the catheter 516 and the extension tubing 514). The fluid volume is small enough that any air in the system will result in no pressure being generated at the pump head. The control board monitors the pump current for any abrupt downward change that may indicate that air has entered the system. If the rate of drop is faster than a preset limit, the control board will disable the pump by cutting power to it until the problem is corrected. Likewise, a block in the high pressure lumen 536, which may be due to the entry of organized or fibrous thrombus, or a solid embolus, may be detected by monitoring the electrical current running the pump 526. In normal use, the current fluxuations of the pump 526 are relatively high. For example, the pump may be configured so that there is a variation of 200 milliAmps or greater in the current during normal operation, so that when current fluxuations drop below 200 milliAmps, air is identified, and the system shuts down. Alternatively, current fluxuations in the range of, for example, 50 milliAmps to 75 milliAmps may be used to identify that air is in the system. Additionally, an increase in the current or current fluxuations may indicate the presence of clot or thrombus within the high pressure lumen 536. For example, a current of greater than 600 milliAmps may indicate that thrombus it partially or completely blocking the high pressure lumen 536, or even the aspiration lumen 538.

A vacuum line 556, connected to the vacuum source 522, may be connected to a negative pressure sensor 558. If the vacuum of the vacuum source 522 is low or if a leak is detected in the vacuum line 556, the control board 550 disables the pump 526 until the problem is corrected. The negative pressure sensor 558 may also be part of a safety circuit 560 that will not allow the pump 526 to run if a vacuum is not present. Thereby a comprehensive safety system 562, including the safety circuit 560, the pressure sensor 564 and/or the optical device 566, and the negative pressure sensor 558, requires both pump pressure and vacuum pressure for the system to run. If a problem exists (for example, if there is either a unacceptably low pump pressure or an absence of significant vacuum), the control board 550 will not allow the user to operate the aspiration system 510 until all problems are corrected. This will keep air from being injected into a patient, and will assure that the aspiration system 510 is not operated at incorrect parameters.

FIG. 17 is a diagrammatic view of the distal end portion 568 of the assisted catheter aspiration system 510, showing more details of the catheter 516. The catheter 516 is a single-operator exchange catheter and includes a short guidewire lumen 534 attached to the distal end of the device. The guidewire lumen 534 can be between about 1 and about 30 cm in length, or between about 5 and about 25 cm in length, or between about 5 and about 20 cm in length, or approximately 13.5 cm in length. An aspiration lumen 538 includes a distal opening 540 which allows a vacuum (for example, from vacuum source 522) to draw thrombotic material into the aspiration lumen 538. A high pressure lumen 536 includes a distal orifice 542 that is set proximally of distal opening 540 by a set amount. For example, distal orifice 42 can be set proximally of distal opening 540 by about 0.0508 cm (0.020 inches), or by 0.0508 cm±0.00762 cm (0.020 inches±0.003 inches) or by another desired amount. The orifice 542 is configured to spray across the aspiration lumen to macerate and/or dilute the thrombotic material for transport to vacuum source 522, for example, by lowering the effective viscosity of the thrombotic material. The axial placement of the fluid orifice 542 is such that the spray pattern interaction with the opposing lumen wall produces a spray mist and not a swirl pattern that could force embolic material out from the distal opening 540. The system may be configured so that the irrigation fluid leaves the pump at a pressure of between about 3,447,378 pascal (500 psi) and about 10,342,135 pascal (1500 psi). In some embodiments, after a pressure head loss along the high pressure lumen 536, the irrigation fluid leaves orifice 542 at between about 4,136,854 pascal (600 psi) and about 8,273,708 pascal (1200 psi), or between about 4,481,592 pascal (650 psi) and about 5,860,543 pascal (850 psi). In some cases, it may be possible (and even desired) to use the assisted catheter aspiration system 510 without operating the pump 526, and thus use the catheter 516 while providing, for example, a hand saline injection via a syringe. Or, in some cases, the assisted catheter aspiration system 510 may be used without the pump 526 attached, with the saline injections done by hand using a syringe through the high pressure lumen 536. If a clog occurs, the syringe may be removed and the pump 526 attached and initiated, for example, for the purpose of unclogging the high pressure lumen 536.

When normal blood flow is achieved after unblocking occlusions or blockages from atherosclerotic lesions and/or thrombosis, there is sometimes a risk of reperfusion injury. This may be particularly significant following thrombectomy of vessels feeding the brain for treatment of thromboembolic stroke, or following thrombectomy of coronary vessels feeding the myocardium. In the case of the revascularization of myocardium following a coronary intervention (e.g. thrombectomy). Reperfusion injury and microvascular dysfunction may be mechanisms that limit significant or full recovery of revascularized myocardium. The sudden reperfusion of a section of myocardium that had previously been underperfused may trigger a range of physiological processes that stun or damage the myocardium. Distal coronary emboli, such as small portions of thrombus, platelets and atheroma, may also play a part. Controlled preconditioning of the myocardium at risk has been proposed to limit the effect of reperfusion injury and microvascular dysfunction. The embodiments of the thrombectomy systems 100, 300 presented herein may be combined with additional features aimed at allowing flow control, in order to limit the potential dangers due to reperfusion following thrombectomy. Other contemplated embodiments of an assisted aspiration system 510 which may be utilized are disclosed in U.S. Patent Application Publication No. 2010/0094201 to Mallaby ("Mallaby") published Apr. 15, 2010, which is incorporated herein by reference in its entirety for all purposes. Other contemplated aspiration catheters are disclosed in U.S. Patent Application Publication No. 2008/0255596 to Jenson et al. ("Jenson") published Oct. 16, 2008, which is incorporated herein by reference in its entirety for all purposes.

FIG. 18 illustrates a multi-purpose system 1200 comprising a multi-purpose catheter 1202 having an infusion/injection port 1204 and an aspiration port 1206. The infusion/injection port 1204 and the aspiration port 1206 may each comprise luer connectors, such as female luer lock connectors. A tubing set 1208 and a pressure sensor 1210 are connected in line with a vacuum source 1212. A cable 1214 carries signals from the pressure sensor 1210 to an aspiration monitoring system 1216 (FIG. 19), and connects to the aspiration monitoring system 1216 via an interface 1218, or plug, which is configured to connect to a port 1220 of a console 1222 of the aspiration monitoring system 1216. Apparatus and methods described herein may be used to monitor aspiration using the aspiration monitoring system 1216. In one manner of use, a syringe 1224 (FIG. 18) may be used to manually inject through the injection port 1204 and injection lumen 1225 (e.g., high pressure lumen) of the multi-purpose catheter 1202. The syringe 1224 may have an injectable volume of about 5 ml or less, or in some embodiments about 1 ml or less. The injection lumen 1225 in some embodiments may be configured for injection of saline at a relatively high pressure, or at either high or low pressures. If the valve 1226 (e.g., stopcock) is closed, blocking the vacuum source 1212 from applying a vacuum to the aspiration lumen 1227 via the aspiration port 1206, then injection through the injection lumen 1225 causes injectate to be delivered to a site in the blood vessel near the distal exit of the injection lumen 1225 (at the distal end of the multi-purpose catheter 1202). Or, if the vacuum source 1212 is removed from, or simply not coupled to, the aspiration lumen 1227, then injection through the injection lumen 1225 may also cause injectate to be delivered to a site in the blood vessel near the distal exit of the injection lumen 1225. Either of these techniques may be utilized to apply a medicant to a blood vessel wall, or to an atherosclerotic plaque, or to a thrombus. In some cases, a clot busting drug (tissue plasminogen activator-tPA, thrombokinase, urokinase, thrombin, plasmin) is infused into a clot or thrombus, allowing it to act over a period of time. One purpose may be to soften the thrombus over time. Lytics, glycoprotein inhibitors (GPIs), vasodilators, and other drugs may be used to dilate the blood vessel, or treat disease in the area. The controlled, precision, local delivery allows an efficient use of the drug, with the desired amount delivered to the tissue to be treated with minimal runoff or waste. As many of these drugs are quite expensive, this efficiency reduces procedural costs. Because of the precision diameter of the injection lumen 1225, and its known length, the injection lumen 1225 contains a known volume, or dead space. This additionally allows a known, controlled, precision injection of medicant. A representative injection lumen 1225 may have a length of 150 cm and have an inner diameter of 0.038 cm (0.015 inches), and thus a total volume of only 0.17 ml. The injection lumen 1225 volume may be varied, by controlling the diameter of the inner diameter of the injection lumen 1225 and/or the length of the injection lumen 1225. For example, the injection lumen 1225 volume may be between about 0.08 ml and about 0.26 ml, or between about 0.14 ml and about 0.20 ml. By injecting through the injection lumen 1225 with a small bore syringe (e.g., 1 ml) or with a precision pump, an accurate measurement of the medicant delivered can be made. If, however, the valve 1226, or stopcock, is opened, connecting the vacuum source 1212 to the aspiration port 1206 and applying a vacuum on the aspiration lumen 1227, a forced aspiration is commenced, as described herein. As described, the injection lumen 1225 may serve either a closed system (aspiration) or an open system (injection of infusate). At the beginning of a procedure, it is not always known what different actions will be required, thus the use of the multi-purpose catheter 1202 and multi-purpose system 1200 may eliminate the need to use multiple catheters (e.g., both a microcatheter and a single function aspiration catheter).

Figure 20:
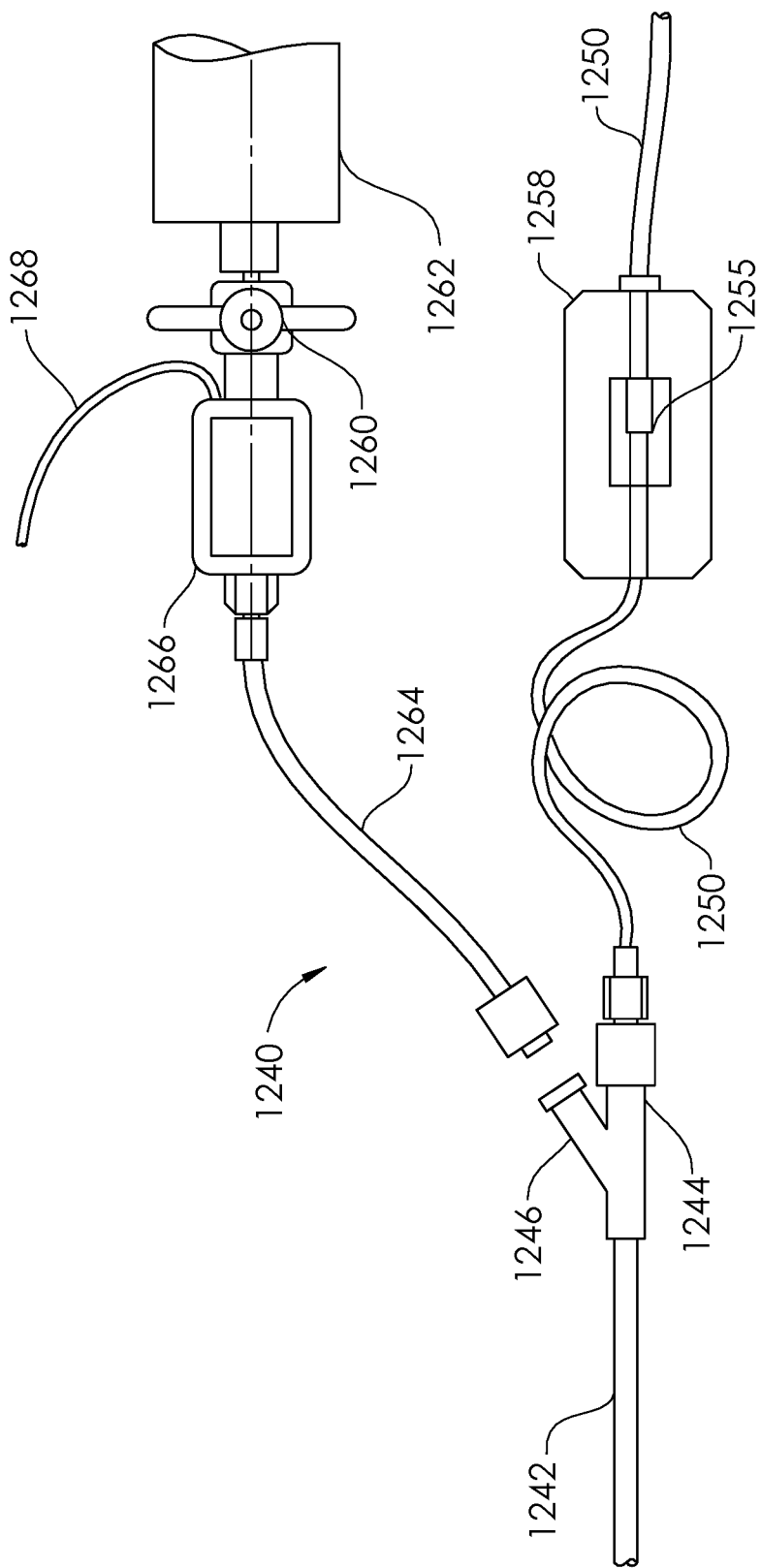
FIG. 20 is a plan view of a portion of a multi-purpose system according to an embodiment of the present disclosure.
Figure 21:
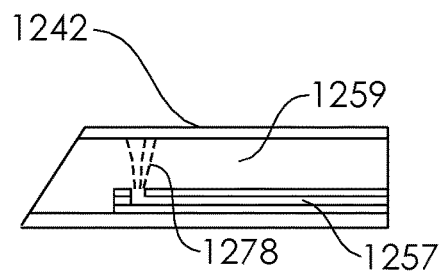
FIG. 21 is a detail view of the distal end of a multi-purpose catheter of the multi-purpose system of FIG. 20.
Figure 22:
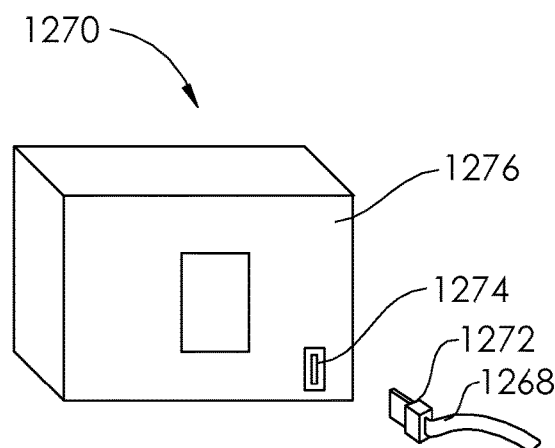
FIG. 22 is a perspective view of a proximal portion of the multi-purpose system of FIG. 20.
Figure 23:
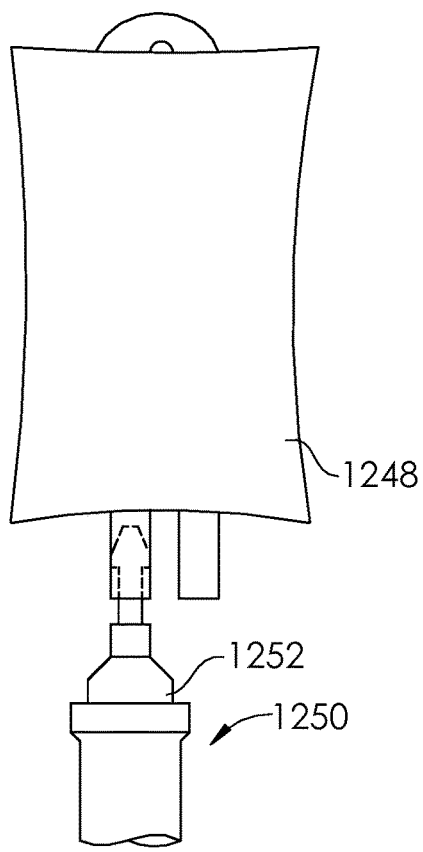
FIG. 23 is a plan view of a proximal portion of the multi-purpose system of FIG. 20.
Figure 24:
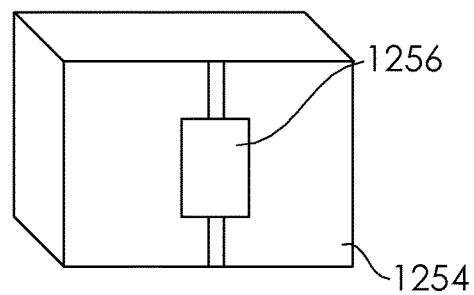
FIG. 24 is a perspective view of a portion of the multi-purpose system of FIG. 20.

FIGS. 20-24 illustrate a multi-purpose system 1240 comprising a multi-purpose catheter 1242 having an infusion/injection port 1244 and an aspiration port 1246. Cooled saline may be injected from a saline bag 1248 (FIG. 23) through a tubing set 1250, attached to the saline bag 1248 via a spike 1252. A pump 1254 (FIG. 24), which may include a displacement pump, such as a piston pump, includes an interface 1256 for attaching a cassette 1258 (FIG. 20). In some embodiments, the pump 1254 has moving portions that connect to a moving piston 1255 in the cassette 1258 to inject controlled amounts of fluid. As described in relation to the multi-purpose system 1200 of FIG. 18, the injection may serve either a closed system (aspiration) or an open system (injection of infusate), depending on whether a valve 1260 which couples a vacuum source 1262 to the aspiration port 1246 via extension tubing 1264 is open or closed, or simply whether the vacuum source 1262 is attached or not attached. A pressure sensor 1266 communicates with the interior of the extension tubing 1264, but may communicate with the interior of other parts of the flow path. A cable 1268 carries signals from the pressure sensor 1266 to an aspiration monitoring system 1270 (FIG. 22), and connects to the aspiration monitoring system 1270 via an interface 1272, or plug, which is configured to connect to a port 1274 of a console 1276 of the aspiration monitoring system 1270. The utility of the multi-purpose systems 1200, 1240 in multiple modes is facilitated by the sterile fluid path combined with precision volume control (either by small syringe 1224, or by the precision pump 1254). In addition, the aspiration monitoring system 1216, 1270 allows real-time feedback to the user, further facilitating controlled delivery and/or aspiration.

The multipurpose system 1200, 1240 optimizes interventional procedures, such as percutaneous coronary interventions (PCIs), for simplicity, case flow, and cost. Infusing drugs intracoronary prepares clot for aspiration by placing highly concentrated pharmaco agents directly at the lesion site, at a location which can be more distal (e.g., more superselective) than that which is typically accessible by the tip of a guiding catheter. This can minimize the volume of drug/medicant/agent used. By limiting the amount of certain medicants, systemic complications (bleeding, etc.) can be minimized or eliminated. The direct application of the medicant, for example at the thrombus itself, allows it to soften or disaggregate the thrombus. The maceration of the thrombus, for example by a saline jet 1278 (FIG. 21) injected through the injection lumen 1257 of the multi-purpose catheter 1242, keeps the catheter aspiration lumen 1259 patent at all times without interruption, and allows standardized catheter advancement technique, for example, moving the catheter slowly from a proximal location to a distal location in the vessel (in relation to the thrombus). The maceration also dilutes the proximally flowing aspirate for optimal suction function. In certain situation, aspiration may be performed until the normal blood flow is restored (at least to a significant level), and then the vacuum source 1262 may be closed off via the valve 1260 and cooled injectate may be infused into the blood vessel. The resultant selective cooling of this area serves to reduce reperfusion injury by potentially slowing ischemic cell metabolism. The injection of cooled infusate may be used any time post-aspiration, pre-stenting, without having to remove an aspiration device, advance a new injection device. Because the multi-purpose catheter 1202, 1242 is already in place, this critical operation may be started immediately. By having these functionalities all on one catheter, there is also a cost saving to the user.

In aspiration mode, the aspiration monitoring system 1216, 1270 is able to monitor proper function of the aspiration circuit at all times. The user knows when warnings are communicated or when the system (e.g., motor) shuts down, that a key event has occurred, an event that needs attending. This knowledge helps the user avoid plunging the catheter distally, potentially causing distal embolism. In infusion/infusate cooling mode, the pump 1254 pumps at a predetermined constant volume or speed to deliver constant temperature cooling infusate. Core temperature feedback (e.g., via rectal, esophageal, ear or other temperature probes) may be used to indicate to the system that further cooling must stop. For example, a core body temperature below 35° C. or below 34° C. The feedback of a temperature below the threshold may be used to shut down the pump and/or to send a warning. The infusate path, which is precision and direct to the catheter tip and/or ischemic area, results in concentrated cooling, causing the least systemic hypothermic potential. By bypassing the aspiration lumen (e.g., with the valve 1260 closed), unintentional embolic debris is less likely to be infused back into the blood vessel, and less likely to thus be sent downstream to critical areas. This eliminates the need to exchange devices after flow has been restored.

In some cases, in infusion mode, infusate is injected into the fluid injection lumen 1225, 1257 with a relatively low pressure. In some cases, maceration is performed at a relatively high pressure. In some cases, the multi-purpose system 1240 may be used without the pump 1254 attached, with the saline injections done by hand using a syringe attached to the infusion/injection port 1244. If a clog occurs, the syringe may be removed and the pump 1254 attached and initiated, for example, for the purpose of unclogging the injection lumen 1257. In an exemplary procedure, a user places a catheter similar to the multi-purpose catheter 1202 of FIG. 18 or multi-purpose catheter 1242 of FIGS. 20-21 in the vasculature. Initially, the user may choose to have neither a pump 1254, nor a syringe 1224 (FIG. 18) attached to the multi-purpose catheter 1202, 1242. The user may then commence aspiration through the aspiration lumen 1227, 1259 via a vacuum source 1212, 1262, thus utilizing the multi-purpose catheter 1202, 1242 as a simple (vacuum only) aspiration catheter. If at any time, the user determines that additional positive pressure injection of saline and/or medicant is needed, for example, to overcome clogging, overcome slow aspiration, or to increase maceration or dilution of the thrombus, the user can attach the pump 1254 or the syringe 1224 to the infusion/injection port 1204, 1244 and begin injecting the saline and/or medicant.

In one embodiment, an aspiration system includes an elongate catheter having a proximal end and a distal end, the catheter including an aspiration lumen having a proximal end and a distal end and a high pressure injection lumen having a proximal end and a distal end and extending from a proximal end of the catheter to a location adjacent a distal end of the aspiration lumen, and at least one orifice at or near the distal end of the high pressure injection lumen and configured to allow high pressure liquid injected through the high pressure injection lumen to be released into the aspiration lumen, wherein the proximal end of the high pressure injection lumen is configured to be repeatably coupled to and uncoupled from one or more injection modules. In some embodiments, the one or more injection modules include a first injection module and a second injection module. In some embodiments, the first injection module comprises a pump and the second injection module comprises a syringe. In some embodiments, the second injection module comprises a syringe having a volume of about 5 ml or less. In some embodiments, the second injection module comprises a syringe having a volume of about 1 ml or less. In some embodiments, the second injection module comprises a syringe containing a drug.

FIGS. 25 through 33 illustrate several different embodiments of devices having a pressure sensor 1300, which is configured to function as a component in an aspiration monitoring system sharing some or all of the functionality of any one of the aspiration monitoring systems 48, 62, 78, 900, 1216, 1270 presented herein. FIG. 25 illustrates an aspiration catheter 1302 having a distal end 1304 and a proximal end 1306, the proximal end 1306 comprising a female luer connector 1308. The pressure sensor 1300 is in fluid communication with (e.g., fluidly coupled to) a lumen of the aspiration catheter 1302. FIG. 26 illustrates a tubing set 1310 having a male luer 1312 and a female luer 1314, extension tubing 1316, and a stopcock 1318. The pressure sensor 1300 is in fluid communication with a lumen of the extension tubing 1316. FIG. 27 illustrates a stopcock 1320 having a male luer 1322, a female luer 1324, and a valve 1326, the valve 1326 located proximally of the pressure sensor 1300. The pressure sensor 1300 is in fluid communication with an internal cavity of the stopcock 1320. FIG. 28 illustrates a stopcock 1328 having a male luer 1330, a female luer 1332, and a valve 1334, the valve 1334 located distally of the pressure sensor 1300. The pressure sensor 1300 is in fluid communication with an internal cavity of the stopcock 1328. FIG. 29 illustrates a syringe 1336 having a male luer 1342, a barrel 1338, and a plunger 1340. The syringe 1336 may include a locking feature 1344, which allows the plunger 1340 to be locked in relation to the barrel 1338, such as a VacLok® syringe. The pressure sensor 1300 is located distally of the barrel 1338 and is in fluid communication with an internal cavity of the barrel 1338.

Figure 30:
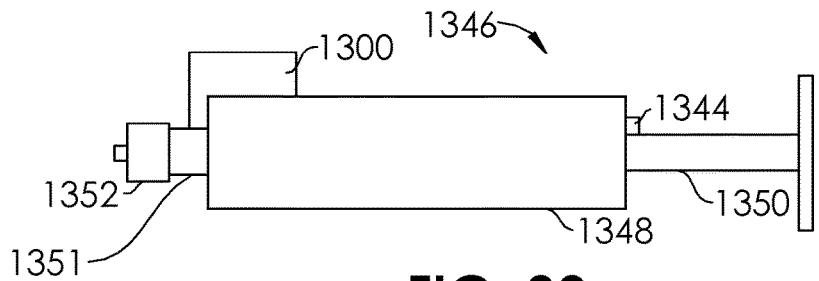
FIG. 30 is a plan view of an aspiration system according to an embodiment of the present disclosure.
Figure 31:
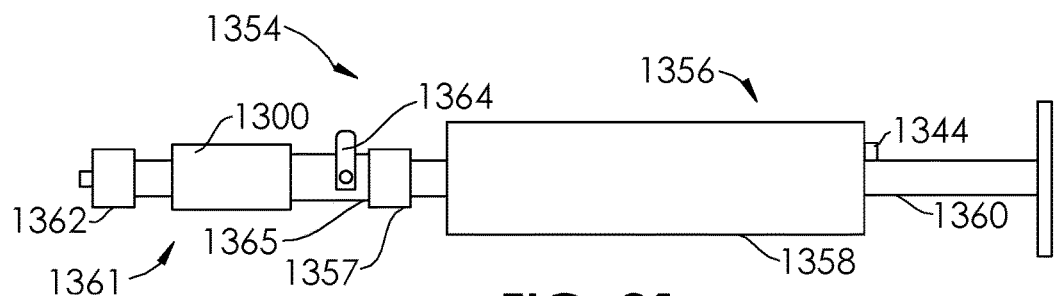
FIG. 31 is a plan view of an aspiration system according to an embodiment of the present disclosure.
Figure 32:
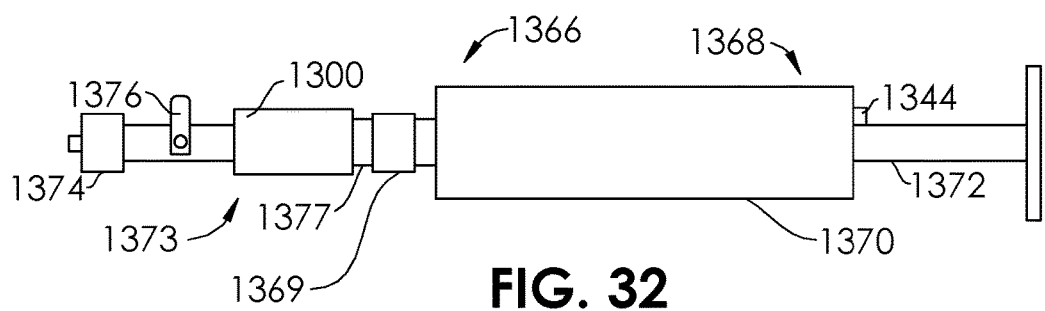
FIG. 32 is a plan view of an aspiration system according to an embodiment of the present disclosure.
Figure 33:
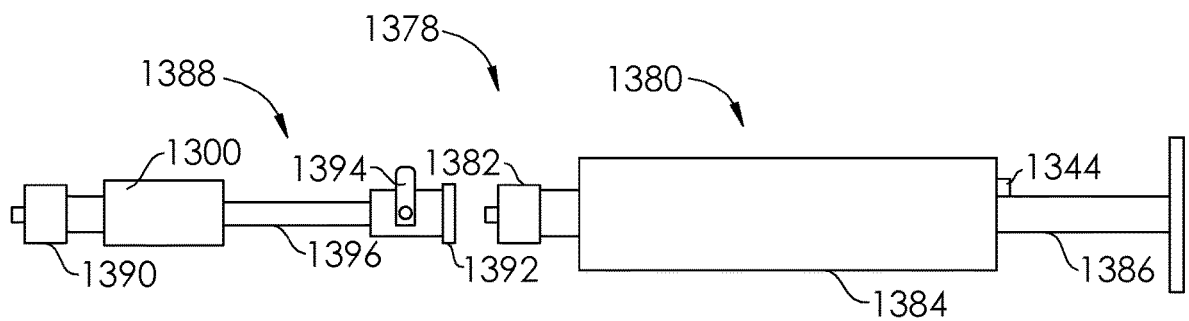
FIG. 33 is a plan view of an aspiration system according to an embodiment of the present disclosure.

FIG. 30 illustrates a syringe 1346 having a male luer 1352 (i.e., luer connector, luer lock), a barrel 1348, and a plunger 1350. The syringe 1346 may include a locking feature 1344. The pressure sensor 1300 is in fluid communication with an internal cavity of the barrel 1348, and may be directly connected to either the barrel 1348 or the male luer 1352, or a hollow transition 1351 between them. FIG. 31 illustrates an aspiration system 1354 comprising a syringe 1356 having a male luer 1357, a barrel 1358 and a plunger 1360. The syringe 1356 may include a locking feature 1344. The aspiration system 1354 also comprises a connector assembly 1361 comprising a male luer 1362, a valve 1364, and a female luer 1365 (connected under the male luer 1357 in FIG. 31). The pressure sensor 1300 is in fluid communication with an internal lumen or cavity between the barrel 1358 of the syringe 1356 and the male luer 1362 of the connector assembly 1361. FIG. 32 illustrates an aspiration system 1366 comprising a syringe 1368 having a male luer 1369, a barrel 1370 and a plunger 1372. The syringe 1368 may include a locking feature 1344. The aspiration system 1366 also comprises a connector assembly 1373 comprising a male luer 1374, a valve 1376, and a female luer 1377 (connected under the male luer 1369 in FIG. 32). The pressure sensor 1300 is in fluid communication with an internal lumen or cavity between the barrel 1370 of the syringe 1368 and the male luer 1374 of the connector assembly 1373. FIG. 33 illustrates an aspiration system 1378 comprising a syringe 1380 having a male luer 1382, a barrel 1384 and a plunger 1386. The syringe 1380 may include a locking feature 1344. The aspiration system 1378 further comprises a tubing set 1388 having a male luer 1390 and a female luer 1392. A valve 1394 is located either proximal or distal to the pressure sensor 1300. Extension tubing 1396 may be utilized to connect one or more of the components of the tubing set 1388, but in some cases, the components may be connected directly. The pressure sensor 1300 is in fluid communication with an internal lumen of the tubing set 1388. The stopcock or valve in any of these embodiments may be a one-way stopcock or a three-way stopcock or a one-way valve or a three-way valve. Other embodiments may exist which combine one or more elements of each of the embodiments presented herein. These embodiments are also included within the scope of this disclosure. In any of the embodiments in which a male luer is used, it may be replaced with a female luer or another liquid-tight connector. In any of the embodiments in which a female luer is used, it may be replaced with a male luer or another liquid-tight connector. As such, either of the connector assemblies 1361, 1373 may be connected in reverse manner to the syringes 1356, 1368, i.e., wherein the distal end becomes the proximal end and is thus connected to the syringe 1356, 1368, and wherein the proximal end becomes the distal end.

Figure 34:
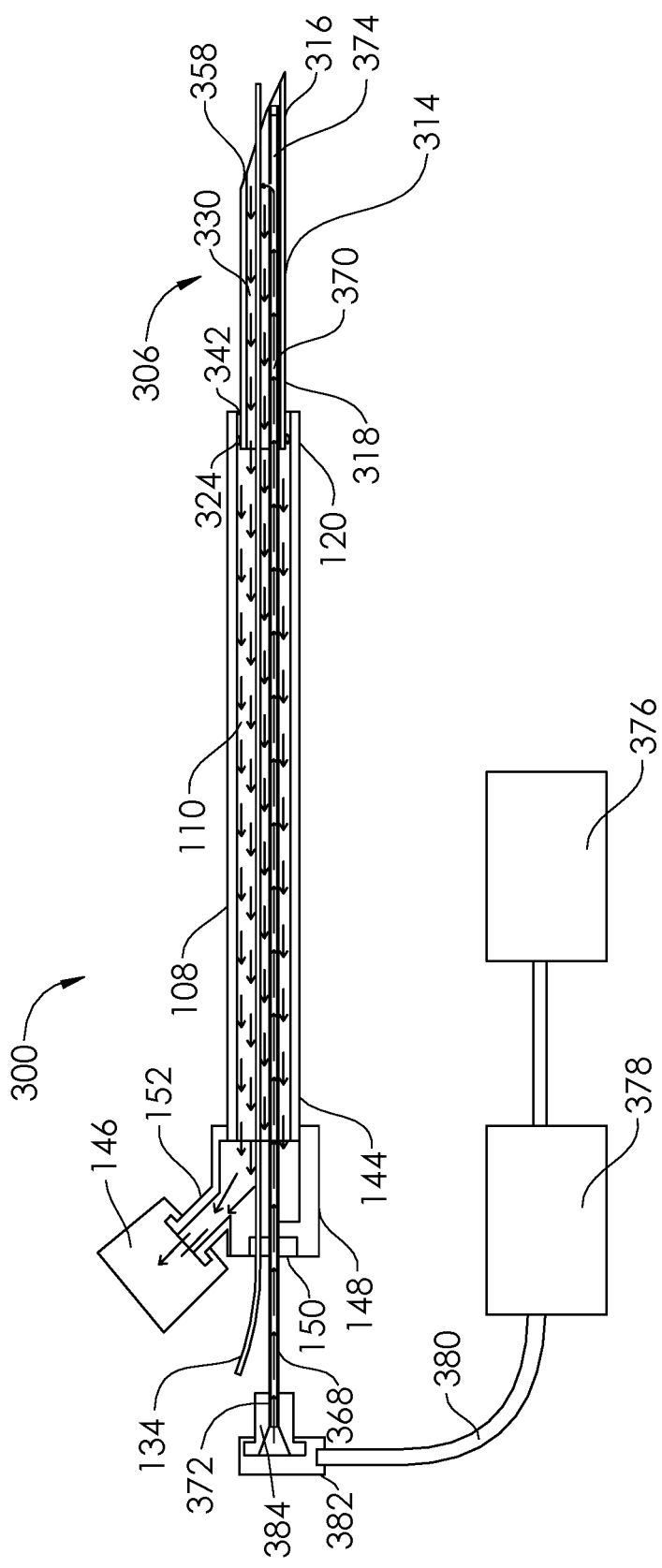
FIG. 34 is a partial sectional view of an embodiment of a saline injection aspiration (thrombectomy) catheter according to an embodiment of the present disclosure, with a guidewire in place.

FIG. 34 illustrates a thrombectomy system 300 which incorporates the high pressure injection of a liquid, for example sterile saline solution, in order to macerate and aspirate thrombus 104. A guiding catheter 108 has an inner lumen 110 extending between a proximal end 144 and a distal end 120. A y-connector 148, coupled to the proximal end 144 of the guiding catheter 108, includes a proximal seal 150 and a sideport 152 and is configured to couple the inner lumen 110 of the guiding catheter 108 to a vacuum source 146, as described in relation to the prior embodiments. A thrombectomy catheter 306 comprises a distal tube 314 having a distal end 316 and a proximal end 318, the proximal end 318 incorporating one or more sealing members 324 for sealing off an annulus 342 between the guiding catheter 108 and the distal tube 314, as described in relation to the prior embodiments. The distal tube 314 has an aspiration lumen 330. A support/supply tube 368, having a lumen 370, is coupled to the distal tube 314. The support/supply tube 368 serves as a support member for pushing and pulling the thrombectomy catheter 306, but is also a conduit (via the lumen 370) for high pressure saline, which is injected from the proximal end 372 to the distal end 374. The saline is supplied from a saline source 376 (e.g. saline bag, bottle) and pressurized by a pump 378, through a supply tube 380 and through a luer connector 382 which is connected to a luer hub 384 coupled to the support/supply tube 368. In some embodiments, the support/supply tube 368 comprises a hypo tube. In some embodiments, the support/supply tube 368 comprises stainless steel or nitinol. The distal end 316 of the distal tube 314 may include a skive 358, which aids in the trackability of the distal tube 314 through vasculature of a patient. In some embodiments, the inner diameter of the aspiration lumen 330 of the distal tube 314 may be approximately one French size smaller than the inner diameter of the inner lumen 110 of the guiding catheter 108.

Figure 35:
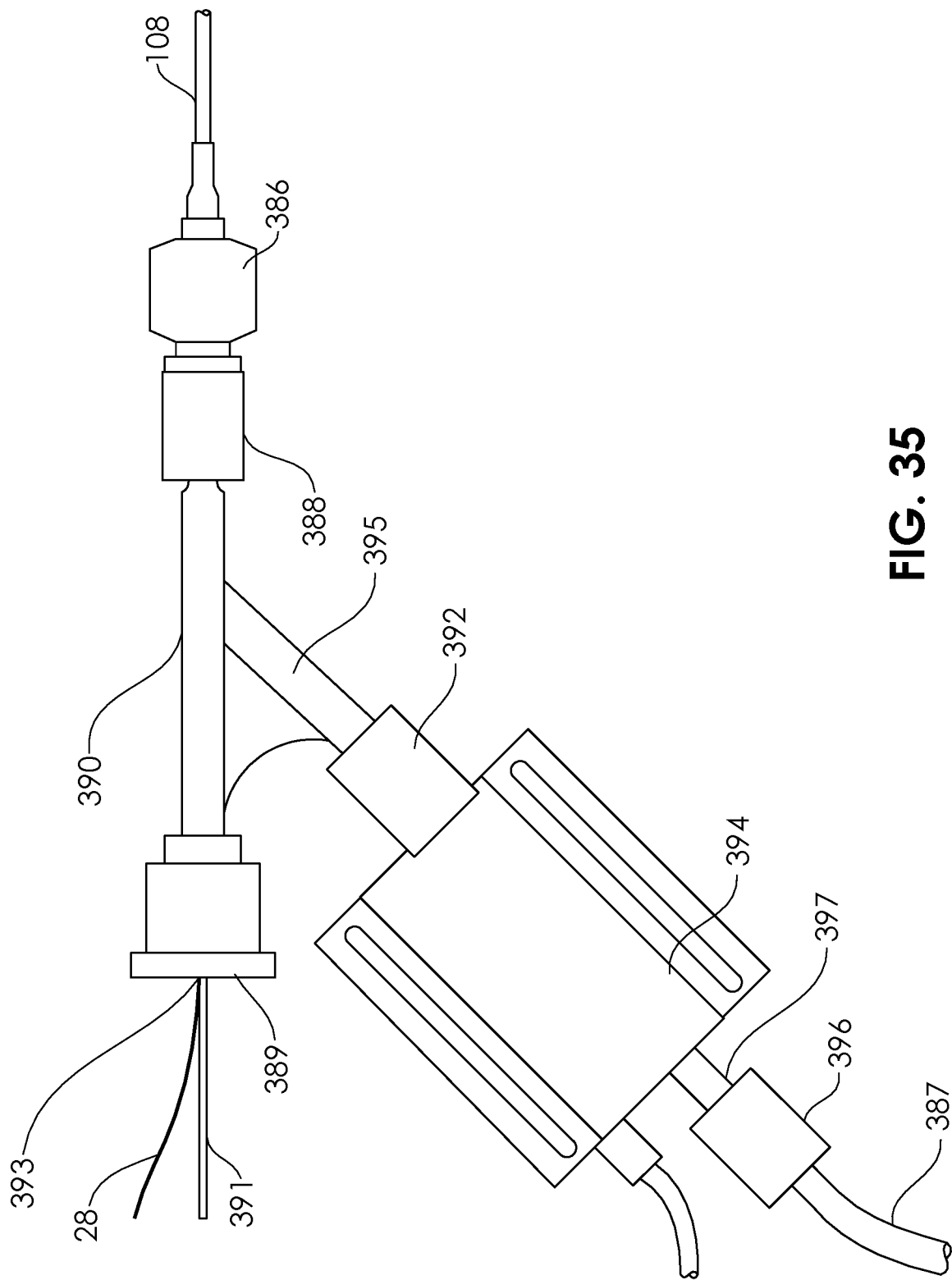
FIG. 35 is a plan view of the proximal end of a guiding catheter with an aspiration catheter placed therein.

FIG. 35 illustrates the proximal end of a guiding catheter 108 used with aspiration catheters, such as the thrombectomy catheter 306 of FIG. 34. A hemostasis valve 389 of y-connector 390 seals over both the support/supply tube 391 and the guidewire 28. The hemostasis valve 389 (e.g., Touhy-Borst, longitudinally spring-loaded seal, etc.) must be adjusted to allow catheter and/or guidewire 28 movement (translation, rotation), but must keep air from being pulled into the lumens during aspiration. Because of the continual adjustment often required to the hemostasis valve 389, for example, to aid movement of the catheter and/or guidewire, the hemostasis valve 389 may create significant variability in the amount of air that may leak. A leak (e.g., at location 393) may be fast, and may be unknown to the user. A pressure sensor 394 used in conjunction with any of the aspiration monitoring systems described herein allows the user to know immediately if the seal of the hemostasis valve 389 of the y-connector 390 is not correctly sealed. Additionally, any leaks between the distal luer 388 of the y-connector 390 and the luer hub 386 of the guiding catheter 108 can be detected by the aspiration monitoring system. Furthermore, any leaks between a luer 392 of the pressure sensor 394 and a sideport 395 of the y-connector 390 or between a luer connector 396 of the extension tube 387 and a luer fitting 397 of the pressure sensor 394 can be detected by the aspiration monitoring system. The aspiration monitoring system may be configured to be integral or attachable to any component of the aspiration circuit (e.g., aspiration catheter, syringe/vacuum source), or may be connected in series (at any point) between these components. In some embodiment, the aspiration monitoring system may comprise a flow or pressure sensor or detector that is in series or in parallel with the components, or is configured to be placed in series or in parallel with the components. In any of these configurations, a number of different leak locations may be assessed by the aspiration monitoring system of the embodiments disclosed herein. The aspiration monitoring system may be configured to detect: changes, relative changes, absolute changes, thresholds, absolute values, the presence of or the lack of pressure and/or flow. The aspiration monitoring system may be configured to determine the operation status of a system including a catheter having an aspiration lumen. In some cases, the aspiration monitoring system may be configured to provide information about the operation of the system that is not discernable from typical clues such as angiography, sound, feel, or other visual, auditory, tactile or other feedback from the system itself.

Figure 36:
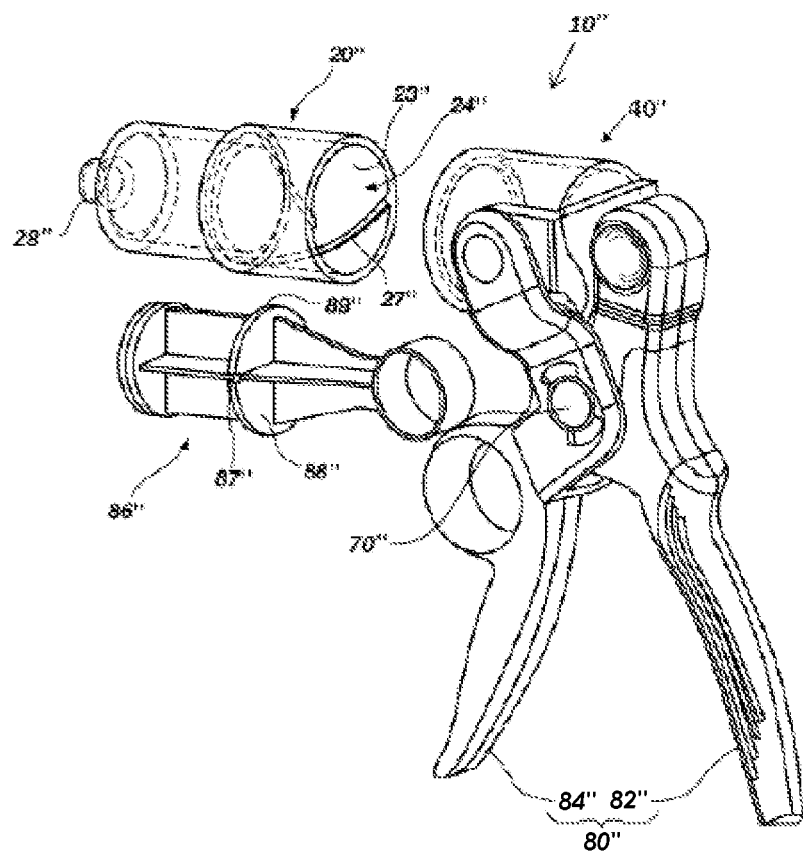
FIG. 36 is a perspective view of a syringe with a rotatable element according to an embodiment of the present disclosure.

FIG. 36 illustrates a syringe 10" having a barrel 20" that is configured to rotate as the plunger 86" of the syringe 10" is drawn from the barrel 20". In some embodiments, the barrel 20" and the corresponding plunger 86" may include cooperating rotation elements that cause the barrel 20" to rotate as the plunger 86" is moved axially along (i.e., forced into or withdrawn from) a receptacle 24" of the barrel 20".

In one specific embodiment, an interior surface 23" of the barrel 20" carries one or more threads 27" (two threads 27" are shown in the illustrated embodiment). The threads 27" are elongate, curved elements that may be at least partially helically oriented and configured to engage or to be engaged by cooperating features of the plunger 86" and to cause rotational movement of barrel 20" relative to the plunger 86". In one particular embodiment, the threads 27" protrude from the interior surface 23" into the receptacle 24" (e.g., as male threads). In another particular embodiment, the threads 27" extend into the interior surface 23" into the receptacle 24" (e.g., as female threads).

An embodiment of the plunger 86" that corresponds to the barrel 20" may include an engagement feature 87", such as the depicted notch, that receives and cooperates with a corresponding thread 27", for example a male thread. In some embodiments, the engagement feature 87" may be a protrusion which engages and cooperates with a corresponding thread 27", for example a female thread. In a more specific embodiment, each engagement feature 87" is formed in an alignment element 88" of the plunger 86". Even more specifically, each engagement feature 87" may be formed in an edge 89" of alignment the alignment element 88" (illustrated as an alignment disk) of the plunger 86". As shown, the alignment element 88" may be located at a proximal end of the plunger 86" (e.g., the end that will be located closest to an individual operating a syringe that includes the barrel 20" and the plunger 86"). Edge 89" of the alignment element 88" may abut the interior surface 23" of the barrel 20" to align the plunger 86" with the receptacle 24" of the barrel 20" as the plunger 86" is forced through the receptacle 24", along the length of the barrel 20". As the plunger 86" is inserted into the receptacle 24" of the barrel 20" and is driven axially along the length of the barrel 20", each engagement element 87" continues to engage its corresponding thread 27". Due to the helical orientation of threads 27", non-rotational movement of the plunger 86" along the length of the barrel 20" causes the barrel 20" to rotate relative to the plunger 86" as the plunger 86" is forced through (i.e., into or out of) the receptacle 24". In the depicted embodiment, movement of the plunger 86" out of the receptacle 24" (i.e., proximally, toward an individual using a syringe including the barrel 20" and the plunger 86") is effected as members 82" and 84" of handle 80" are forced together. Members 82" and 84" of the handle 80" may be rotationally joined to each other at a hinge joint 70". In one embodiment, the barrel 20" is rotationally and sealably held within a stationary cylindrical housing 40" which is secured to member 82" of the handle 80". The barrel 20" may be locked axially within the cylindrical housing 40" by a snap fit, or other locking means. In another embodiment, the barrel 20" is permanently and sealingly bonded within the cylindrical housing 40" such that the barrel 20" and the cylindrical housing 40" are configured to rotate in unison. In this particular embodiment, the cylindrical housing is rotatably held by the member 82" of the handle 80".

Embodiments of syringes with rotatable elements and barrels 20" that rotate relative to their plungers 86" may be used in a variety of procedures, including, but not limited to, processes in which material (e.g., biological samples, samples from the body of a subject, aspiration of blood or thrombus/clot, etc.) is removed and/or obtained.

In a biopsy embodiment, a biopsy needle may be rigidly secured to the barrel 20", for example at coupling element 28". The coupling element 28" may comprises a standard luer connector, such as a male luer lock connector. Movement of the plunger 86" along the length of the barrel 20" may cause the barrel 20" and the attached biopsy needle to rotate about axes extending along their lengths, enabling use of the biopsy needle in a coring and aspiration technique to manually obtain a sample. A hand held syringe incorporating teachings of the present disclosure may be advanced and operated manually, even with a single hand, which may free the operator's other hand for a variety of purposes, including, without limitation, stabilization of a patient, control of an imaging device, such as an ultrasound apparatus, or the like.

In embodiments wherein a catheter is rigidly coupled to a barrel 20"(e.g., at the coupling element 28") that rotates as its corresponding plunger 86" is driven along its length, actuation of the plunger 86" may rotate the catheter about an axis extending along its length, which may be useful in breaking up or dislodging obstructions, macerating and/or removing blood clots or thrombi, or in mixing fluids prior to or during their aspiration.

Figure 37:
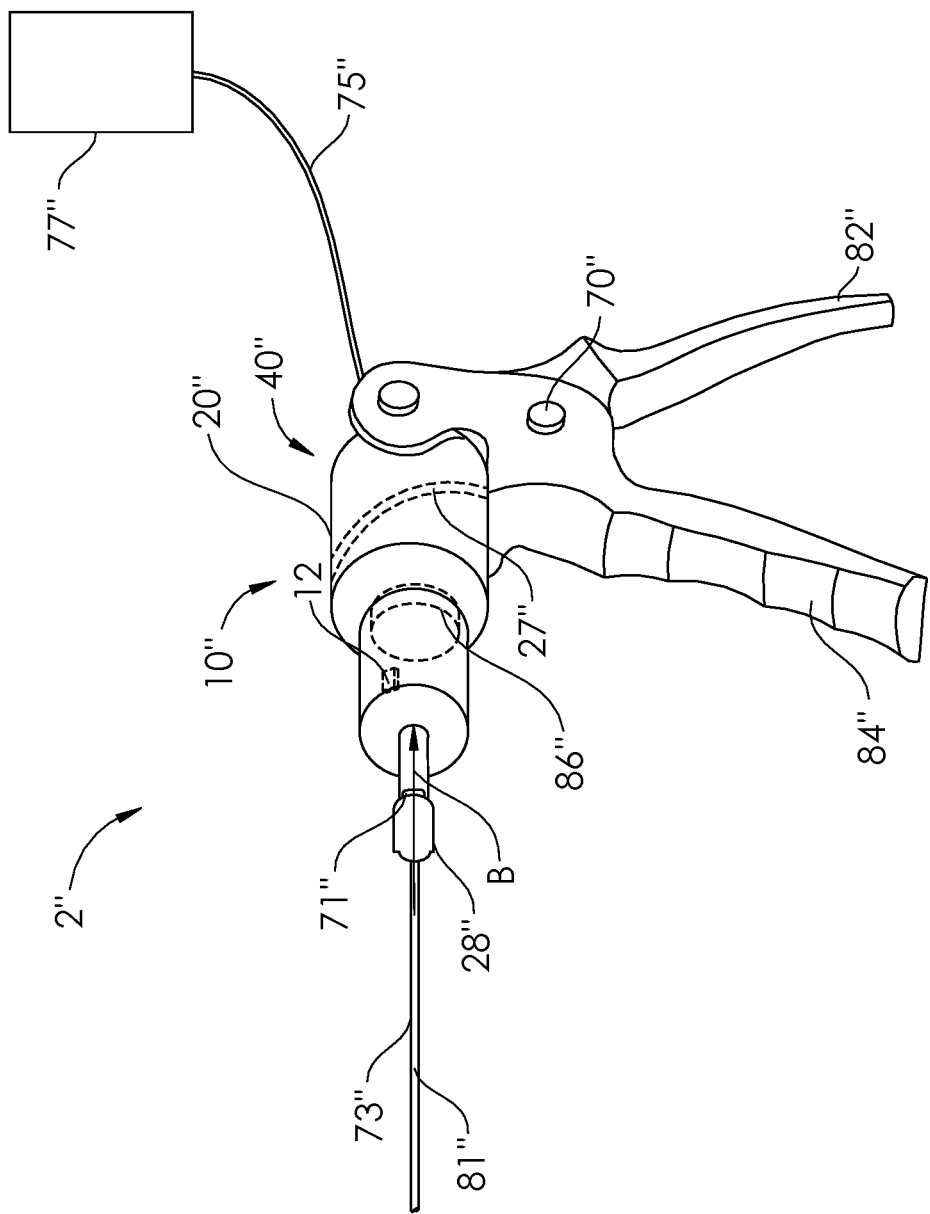
FIG. 37 is a perspective view of an aspiration system utilizing one modification of the syringe of FIG. 36 according to an embodiment of the present disclosure.
Figure 38:
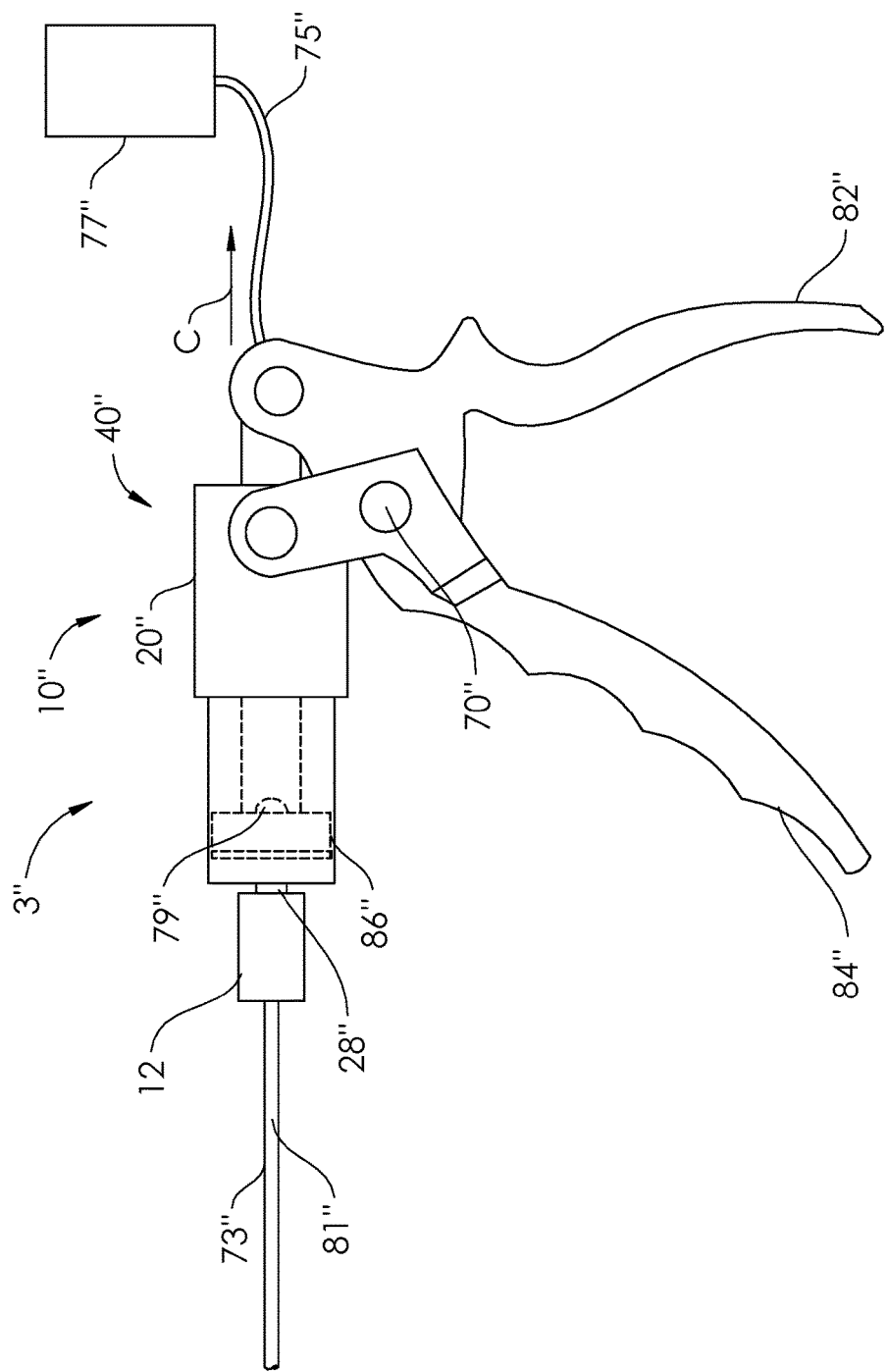
FIG. 38 is a side view of aspiration system utilizing another modification of the syringe of FIG. 36 according to an embodiment of the present disclosure.

FIG. 37 illustrates an aspiration system 2" utilizing an embodiment of the syringe 10" which includes a first one-way valve 71" between the aspiration catheter 73" and the barrel 20", which allows flow (for example of thrombus or blood) from the aspiration lumen 81" of the aspiration catheter 73" into the interior of the barrel 20", in the direction of arrow B, but does not allow flow in the opposite direction. The flow may travel, for example, into the interior of the barrel 20" during aspiration (e.g., when the members 82" and 84" are squeezed together). A vacuum source 77" may be used to collect aspirated material (thrombus, blood, etc.) via an extension tube 75". FIG. 38 illustrates a system 3" including a second one-way valve 79" within the plunger 86" which allows flow from the interior of the barrel 20" to the vacuum source 77", in the direction of arrow C, but does not allow flow in the opposite direction. The flow may travel, for example, towards the vacuum source 77" when the members 82" and 84" are released. Both the first one-way valve 71" and the second one-way valve 79" may be incorporated together in either the system 2" of FIG. 37 or the system 3" of FIG. 38. A pressure transducer 12 may be used as part of any of the aspiration monitoring systems described herein to determine the status of the aspiration utilizing the system 2" or the system 3". In system 2" of FIG. 37, the pressure transducer 12 is located within the interior of the barrel 20", while in system 3" of FIG. 38, the pressure transducer 12 is located in-line between the aspiration catheter 73" and the coupling element 28". In some embodiments, the pressure transducer 12 may be a separate component that is attached at one end to the aspiration catheter 73" and at the other end to the coupling element 28". For example, the pressure transducer 12 may be supplied separately, and may be configured for the user to couple to the aspiration catheter 73" and the coupling element 28" in order to perform a procedure. In some embodiments, the pressure transducer 12 may be supplied as part of the coupling element 28", and be configured to be attached to the aspiration catheter 73". In some embodiments, the pressure transducer 12 may be supplied as part of the aspiration catheter 73" and be configured to be attached to the coupling element 28". Feedback from the pressure transducer 12 via the aspiration monitoring system may alert the user when to squeeze the members 82" and 84", or when to release the members 82" and 84", or when to replace the vacuum source 77". For example, the aspiration monitoring system may be configured to alert the user when the vacuum has decreased below a threshold, and may send a message to the user, such as, "squeeze handle." Additionally, the aspiration monitoring system may be configured to alert the user when a no-flow condition is identified, indicating possible clogging, and may send a message to the user such as "release handle" or "replace syringe."

Any of the embodiments described herein may include some or all features of any of the embodiments described in U.S. Patent Application Publication No. 2014/0200483 to Fojtik, published Jul. 17, 2014, which is incorporated herein by reference in its entirety for all purposes; in addition, any of the features described herein may be incorporated into any of the embodiments described in Fojtik, U.S. Patent Application Publication No. 2014/0200483, while remaining within the scope of the present disclosure.

Any of the embodiments described herein may include some or all features of any of the embodiments described in U.S. Patent Application Publication No. 2004/0116873 to Fojtik, published Jun. 17, 2004, which is incorporated herein by reference in its entirety for all purposes; in addition, any of the features described herein may be incorporated into any of the embodiments described in Fojtik, U.S. Patent Application Publication No. 2004/0116873, while remaining within the scope of the present disclosure.

Any of the embodiments described herein may include some or all features of any of the embodiments described in U.S. Patent Application Publication No. 2012/0022404 to Fojtik, published Jan. 26, 2012, which is incorporated herein by reference in its entirety for all purposes; in addition, any of the features described herein may be incorporated into any of the embodiments described in Fojtik, U.S. Patent Application Publication No. 2012/0022404, while remaining within the scope of the present disclosure.

Any of the embodiments described herein may include some or all features of any of the embodiments described in U.S. Patent Application Publication No. 2014/0142594 to Fojtik, published May 22, 2014, which is incorporated herein by reference in its entirety for all purposes; in addition, any of the features described herein may be incorporated into any of the embodiments described in Fojtik, U.S. Patent Application Publication No. 2014/0142594, while remaining within the scope of the present disclosure.

Any of the embodiments described herein may be used conjunction with any model of the Aspire Aspiration Platform syringe (Control Medical Technology, LLC, Park City, Utah, USA), having either a rotating barrel or a non-rotating barrel.

In one embodiment, an aspiration system includes an elongate catheter having a proximal end and a distal end, the catheter including an aspiration lumen having a proximal end and a distal end, a manually-actuated syringe configured to aspirate liquid, the syringe including one or more actuation elements which control the amount of vacuum applied to the interior of the syringe and a connector configured for fluid connection, and a monitoring device including a housing having a first port adapted for detachable connection to the connector of the syringe and a second port adapted for detachable connection with the catheter, a pressure sensor in fluid communication with an interior of the housing, a measurement device coupled to the pressure sensor and configured for measuring one or more deviations in fluid pressure, and a communication device coupled to the measurement device and configured to generate a signal related to a deviation in fluid pressure measured by the measurement device.

In another embodiment, an aspiration system includes an elongate catheter having a proximal end and a distal end, the catheter including an aspiration lumen having a proximal end and a distal end, a manually-actuated syringe configured to aspirate liquid, the syringe including one or more actuation elements which control the amount of vacuum applied to the interior of the syringe and a connector configured for fluid connection, and a monitoring device including a pressure sensor in fluid communication with an interior of the syringe, a measurement device coupled to the pressure sensor and configured for measuring one or more deviations in fluid pressure, and a communication device coupled to the measurement device and configured to generate a signal related to a deviation in fluid pressure measured by the measurement device.

Figure 39:
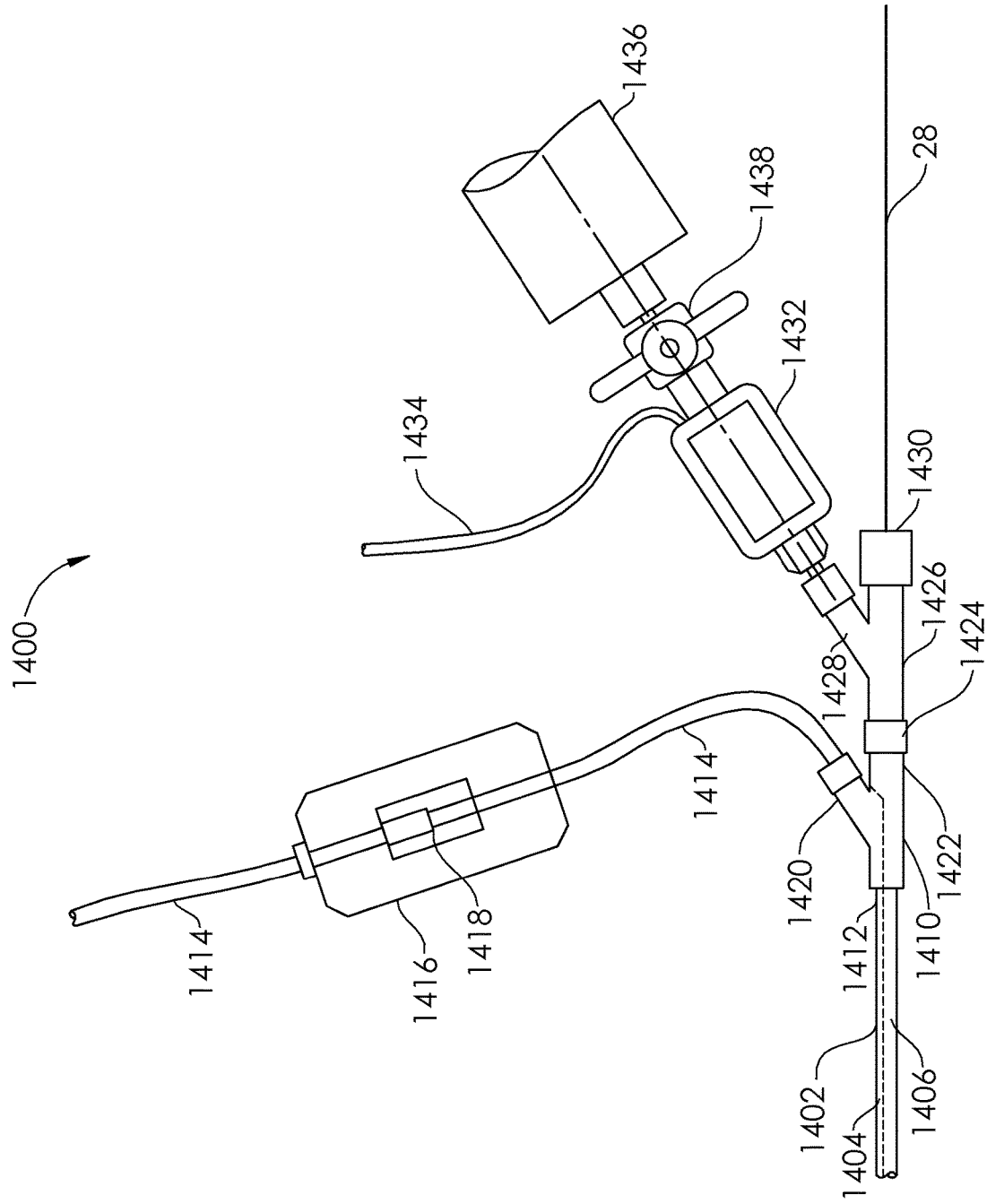
FIG. 39 is a plan view of an aspiration system according to another embodiment of the present disclosure.

An aspiration system 1400 is illustrated in FIG. 39 and comprises an aspiration catheter 1402 that is configured to be deliverable over a guidewire 28. The aspiration catheter 1402 includes a high pressure fluid injection lumen 1404 and an aspiration lumen 1406. The aspiration lumen 1406 extends from the proximal end 1412 of the aspiration catheter to a distal end and is configured to also serve as a guidewire lumen. A first y-connector 1410 is coupled to the proximal end 1412 of the aspiration catheter 1402 and communicates with for the high pressure fluid injection lumen 1404 and the aspiration lumen 1406. The high pressure fluid injection lumen 1404 may be configured in a similar manner to the high pressure fluid injection lumen 536 of the embodiment of FIG. 17, the injection lumen 1225 of the embodiment of FIG. 18 or the injection lumen 1257 of FIG. 21. A sideport 1420 of the first y-connector 1410 is in fluid communication with the high pressure injection lumen 1404 and a proximal port 1422 is in fluid communication with the aspiration lumen 1406. The first y-connector 1410 may be permanently attached to the proximal end 1412 of the aspiration catheter 1402, or may be connectable to the proximal end 1412, for example, by luer connections. A tubing set 1414 having a cassette 1416 with a piston 1418 is configured to be coupled to the sideport 1420 of the first y-connector 1410, and is also configured to be coupled to and used with the pump 1254 of FIG. 24, or other equivalent pumps. The proximal port 1422 of the first y-connector 1410 is configured to be coupled to a distal port 1424 of a second y-connector 1426. The proximal port 1422 of the first y-connector 1410 and the distal port 1424 of the second y-connector 1426 may be luer connectors, but alternatively, they may be permanently connected. Alternatively, the first y-connector 1410 and the second y-connector 1426 may be integrally formed, for example by injection molding or casting. The second y-connector 1426 includes a sideport 1428 and a hemostasis valve 1430 (Touhy-Borst, spring-loaded seal, etc.). The hemostasis valve 1430 is configured for sealing over the guidewire 28 and may be adjustable or actuatable in order to more easily move advance and retract the guidewire 28, distally and proximally. The sideport 1428 is configured to couple to a pressure sensor 1432 having a cable 1434 for carrying one or more signals. The pressure sensor 1432 is configured to interface with the console 1276 of FIG. 22 or other equivalent consoles. A vacuum source 1436 may be coupled to the sideport 1428/pressure sensor 1432 as described herein. In this particular embodiment, the vacuum source 1436 is syringe. A valve 1438 is placed in between the vacuum source 1436 and the pressure sensor 1432, in fluid communication with each, and allows the user to open or close the connection between the vacuum source 1436 and the pressure sensor 1432.

Any of the embodiments described herein may include some or all features of any of the embodiments described in U.S. Patent Application Publication No. 2007/0073233 to Thor et al. ("Thor") published Mar. 29, 2007, which is incorporated herein by reference in its entirety for all purposes; in addition, any of the features described herein may be incorporated into any of the embodiments described in Thor, while remaining within the scope of the present disclosure.

Any of the embodiments described herein may include some or all features of any of the embodiments described in U.S. Patent Application Publication No. 2001/0051811 to Bonnette et al. ("Bonnette") published Dec. 13, 2001, which is incorporated herein by reference in its entirety for all purposes; in addition, any of the features described herein may be incorporated into any of the embodiments described in Bonnette, while remaining within the scope of the present disclosure.

Any of the embodiments described herein may include some or all features of any of the embodiments described in U.S. Patent Application Publication No. 2014/0155931 to Bose et al. ("Bose") published Jun. 5, 2014, which is incorporated herein by reference in its entirety for all purposes; in addition, any of the features described herein may be incorporated into any of the embodiments described in Bose, while remaining within the scope of the present disclosure.

Any of the embodiments described herein may include some or all features of any of the embodiments described in U.S. Patent Application Publication No. 2010/0204672 to Lockhart et al. ("Lockhart") published Aug. 12, 2010, which is incorporated herein by reference in its entirety for all purposes; in addition, any of the features described herein may be incorporated into any of the embodiments described in Lockhart, while remaining within the scope of the present disclosure.

Any of the embodiments described herein may include some or all features of any of the embodiments described in U.S. Patent Application Publication No. 2007/0225739 to Pintor et al. ("Pintor") published Sep. 27, 2007, which is incorporated herein by reference in its entirety for all purposes; in addition, any of the features described herein may be incorporated into any of the embodiments described in Pintor, while remaining within the scope of the present disclosure.

While the foregoing is directed to embodiments of the present disclosure, other and further embodiments may be devised without departing from the basic scope thereof.

What is claimed is:

1. A system for real time monitoring of catheter aspiration, comprising:
    a pressure sensor configured for placement in fluid communication with a lumen which at least partially includes an aspiration lumen of a catheter, the aspiration lumen configured to couple to a negative pressure source, the pressure sensor configured to measure negative fluid pressure;
    a processor coupled to the pressure sensor and programmed to measure changes in the negative fluid pressure; and
    a communication device coupled to the processor and configured to generate a continuous signal which is characterized by an algorithm that depends on measured negative fluid pressure for communicating the changes in the negative fluid pressure to a user.

2. The system of claim 1, wherein the algorithm is configured such that the continuous signal is generally within a range such that the continuous signal can be sensed by the user throughout the range.

3. The system of claim 2, wherein the continuous signal within the range comprises pitch frequencies within the human audible range.

4. The system of claim 2, wherein the continuous signal within the range comprises sound pressures within the human tolerance range.

5. The system of claim 2, wherein the continuous signal within the range comprises visible light.

6. The system of claim 2, wherein the continuous signal within the range comprises tactilely sensed vibration.

7. The system of claim 1, wherein the continuous signal is proportional to the measured negative fluid pressure.

8. The system of claim 1, wherein the algorithm depends directly on the measured negative fluid pressure as a variable.

9. The system of claim 1, wherein the algorithm depends on a difference between a baseline pressure and the measured negative fluid pressure as a variable.

10. The system of claim 1, wherein the algorithm depends on an absolute value of the measured negative fluid pressure as a variable.

11. A system for real time monitoring of catheter aspiration, comprising:
    a pressure sensor configured for placement in fluid communication with a lumen which at least partially includes an aspiration lumen of a catheter, the aspiration lumen configured to couple to a negative pressure source;
    a processor coupled to the pressure sensor and programmed to measure changes in the fluid pressure; and
    a communication device coupled to the processor and configured to generate a continuous signal which is based on an algorithm that varies depending on the changes in the measured fluid pressure, wherein the continuous signal can be sensed real-time by a user for characterizing the changes in the measured fluid pressure to the user.

12. The system of claim 11, wherein the algorithm is configured such that the continuous signal is generally within a range such that the continuous signal can be sensed by the user throughout the range.

13. The system of claim 12, wherein the continuous signal within the range comprises pitch frequencies within the human audible range.

14. The system of claim 12, wherein the continuous signal within the range comprises sound pressures within the human tolerance range.

15. The system of claim 12, wherein the continuous signal within the range comprises visible light.

16. The system of claim 12, wherein the continuous signal within the range comprises tactilely sensed vibration.

17. The system of claim 11, wherein the continuous signal is proportional to the measured fluid pressure.

18. The system of claim 11, wherein the algorithm depends directly on the measured fluid pressure as a variable.

19. The system of claim 11, wherein the algorithm depends on a difference between a baseline pressure and the measured fluid pressure as a variable.

20. The system of claim 11, wherein the algorithm depends on an absolute value of the measured fluid pressure as a variable.

* * * * *